United States Patent [19]
Abrams et al.

[11] Patent Number: 5,518,995
[45] Date of Patent: * May 21, 1996

[54] USE OF COMPOUNDS TO ENHANCE SYNCHRONY OF GERMINATION AND EMERGENCE IN PLANTS

[75] Inventors: Suzanne R. Abrams; Lawrence V. Gusta; Martin J. T. Reaney; Bruce E. Ewan, all of Saskatoon, Canada

[73] Assignee: National Research Council of Canada, Ottawa, Canada

[*] Notice: The portion of the term of this patent subsequent to Apr. 13, 2010, has been disclaimed.

[21] Appl. No.: 41,238

[22] Filed: Mar. 31, 1993

Related U.S. Application Data

[63] Continuation-in-part of Ser. No. 1,723, Jan. 7, 1993, which is a continuation-in-part of Ser. No. 444,704, Dec. 1, 1989, Pat. No. 5,201,931, which is a continuation-in-part of Ser. No. 280,102, Dec. 1, 1988, abandoned.

[51] Int. Cl.$^6$ .......................... A01N 35/02; A01N 35/06
[52] U.S. Cl. .......................... 504/348; 504/193; 504/201; 504/207; 504/288; 504/291; 504/320; 504/325; 504/349; 504/350; 568/446; 568/447; 568/378
[58] Field of Search .................. 504/348, 193, 504/201, 207, 288, 291, 320, 325, 349, 350; 568/446, 447, 378

[56] References Cited

U.S. PATENT DOCUMENTS

| | | | |
|---|---|---|---|
| 4,581,057 | 4/1986 | Nooden | 504/384 |
| 5,201,931 | 4/1993 | Abrams et al. | 504/291 |

OTHER PUBLICATIONS

Oritani et al, "Synthesis and Biological Activity of (±)-2',3'-Dihydro-abscisic Acid", Agric. Biol. Chem., 46(3), 817, 818, 1982.

The Effects of Priming and Ageing on Resistance to Deterioration of Tomato Seeds; Journal of Experimental Botany, vol. 40, No. 214, pp. 593–598, May 1989 by Cosme A. Agerich, Kent J. Bradford and Ana M. Tarquis.

Manipulation of Seed Water Relations Via Osmotic Priming to Improve Germination Under Stress Conditions, HortScience vol. 21(5), Oct. 1986, Kent J. Bradford, Department of Vegetable Crops, University of California, Davis, CA 95616.

Osmotic Priming of Tomato Seeds: Effects on Germination, Field Emergence, Seedling Growth, and Fruit Yield, J. Amer. Soc. Hort. Sci. 112(3):427–432. 1987 by Ana Daniela Alvarado, Kent J. Bradford, and John D. Hewitt, Department of Vegetable Crops, University of California, Davis, CA 95616.

Abscisic acid: an agent to advance and synchronise germination for tomato (*Lycopersicon esculentum* Mill.) seeds, Finch–Savage, W. E. and McQuistan, C. I. (1991), Seed Sci. & Technol., 19, 537–544, Horticulture Research International, Wellesbourne, Warwick, CV359EF.UK.

Effects of combining priming and plant growth regulator treatments on the synchronisation of carrot seed germination, by W. G., Pill, and W. E. Finch–Savage, Delaware Agricultural Experiment Station, Department of Science, College of Agricultural Sciences, University of Delaware, Newark, and Institute of Horticultural Research, Wellesbourne, Warwick, UK, Ann. appl. Biol. (1988), 113, 383–389.

Effects of Pre–Sowing Seed Treatments and Temperatures on Tomato Seed Germination and Seedling Emergence, Scientia Horticultura, 5 (1976) 101–109, Elsevier Scientific Publishing Company, Amsterdam, by W. T. Bussell and D. Gray, National Vegetable Research Station, Wellesbourne, Warwick (Gt. Britain).

Field Emergence of Tomato, Carrot, and Onion Seeds Primed in an Aerated Salt Solution; J. Amer. Soc. Hort. Sci. 11(5): 660–665. 1986, by A. M. Haigh, E. W. R. Barlow and F. L. Milthorpe, School of Biological Sciences, Macquarie University, North Ryde, NSW 2113, Australia, and P. J. Sinclair, Agricultural Institute, Yanco, NSW 2703, Australia.

Salinity Effects on Asparagus Yield and Vegetative Growth, J. Amer. Soc. Hort. Sci. 112(3): 432–436 (1987), by L. E. Francois, U.S. Salinity Laboratory, Agricultural Research Service, U.S. Department of Agriculture, Riverside, CA 92501.

*Primary Examiner*—Allen J. Robinson
*Assistant Examiner*—B. Bembenick

[57] ABSTRACT

The present invention relates to a composition for enhancing synchrony of germination and emergence in plants and comprises an effective amount of a compound having the following general formula (I);

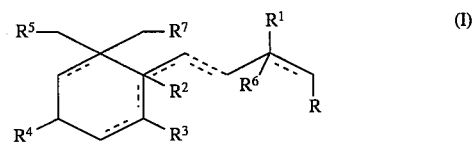

19 Claims, 5 Drawing Sheets

USE OF COMPOUNDS TO ENHANCE SYNCHRONY OF GERMINATION AND EMERGENCE IN PLANTS

This patent application is a continuation-in-part of copending patent application Ser. No. 08/001,723 filed Jan. 7, 1993, which is a continuation-in-part of patent application Ser. No. 444,704 filed Dec. 1, 1989 (U.S. Pat. No. 5,201,931), which is a continuation-in-part of patent application Ser. No. 280,102 filed Dec. 1, 1988 now abandoned. Each of these applications are hereby incorporated by reference.

FIELD OF THE INVENTION

The invention relates to enhancing synchrony of germination and emergence in plants. This is preferably accomplished by using compounds that do not delay germination itself. Particularly, the invention includes the use of compounds having germination enhancing properties in agricultural compositions to be applied to plant parts used in propagation to promote synchrony of germination and emergence in plants.

BACKGROUND OF THE INVENTION

Seed germination occurs over a period of time and this interval is dependent on the species, cultivar and environment. This interval can be as long as 7 to 14 days. This spread in time to emergence results in uneven maturity which presents problems for harvesting the crop. Certain horticultural crops such as tomatoes are harvested mechanically with the plants being sacrificed at the time of harvest. If the stand is not uniform, a large percent of the fruit is not marketable. In cereal crops, the producer must delay harvest until all of the crop is uniform or the crop must be swathed to promote ripening. There are distinct advantages to combining the crop directly. First, less energy is required as the swathing operation is negated. Under cool, wet conditions, it takes longer for the crop to dry down compared to a standing crop. Often a crop that is in a swath may undergo pre-harvest sprouting if conditions are wet. This results in a loss in grade and money. Also, some crops such as canola and wheat may shatter (seeds drop from the plant) while the producer is waiting for the crop to mature.

A period of controlled seed hydration in polyethylene glycol (PEG) or salt solutions (osmotic pruning) is currently used to enhance and synchronize seed germination of vegetable crops. Following treatment with PEG on salt solutions, the seeds must be dried to allow seeding with conventional seeders. In some cases priming of seeds may result in deterioration of seeds especially if the temperature is too warm. If the seeds are not planted immediately, they must be dried back to moisture contents for storage or they may rapidly deteriorate. If PEG is used to treat seeds it must be washed off the seeds prior to planting and storage.

Osmotic priming to enhance and synchronize seed germination is in many respects unsatisfactory. Generally speaking it is lengthy and inconvenient. Simpler, shorter and more efficient alternatives are required.

SUMMARY OF THE INVENTION

In accordance with the present invention, there is provided a class of compounds useful to enhance synchrony of germination and emergence in plants. This is done without delays in germination when comparing overall germination times of treated seeds to germination times of untreated seeds.

In general terms, the present invention first relates to a composition for enhancing synchrony of germination and emergence in plants which comprises an effective amount of a compound having the following formula (I):

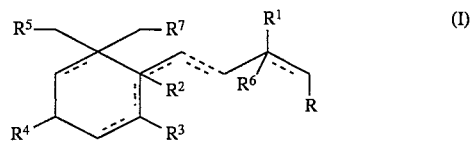

wherein

R is carboxyl, aldehyde, hydroxy, hydroxyloweralkyl, alkoxyloweralkyl, loweralkoxycarbonyl, loweracyloxyloweralkyl, acetylloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, thio, phosphate, sulfoxide, sulfone, deuterium or cycloalkyl or cycloalkoxy having from 4 to 6 carbon atoms which is optionally sbustituted by loweralkyl, halogen, oxygen, hydroxy or loweralkoxy;

$R^1$ is loweralkyl, hydrogen, oxo, hydroxyloweralkyl, loweralkoxy, halogen, thio, sulfoxide, sulfone, phosphate or deuterium;

$R^2$ is hydrogen, oxo, hydroxy, halogen, thio, phosphate, sulfoxide, sulfone or deuterium;

$R^3$ is oxo, thio, carboxyl, aldehyde, loweralkyl, hydroxyloweralkyl, alkoxyloweralkyl, loweralkoxycarbonyl, loweracyloxyloweralkyl, acetylloweralkyl, loweralkanoyl, loweralkylamino, diloweralkylamino, loweralkoxy, loweracyloxy, loweralkylthio, loweralkylhalide, loweralkyldeuterium, loweralkyl sulphonyl, loweralkyl sulphinyl, or carbonyl;

when $R^2$ is oxo or thio, $R^2$ may be linked to both $C_1$ and $C_2$ carbon atoms to form an epoxy or a thioepoxy ring;

and when $R^3$ is oxo or thio, $R^3$ may be linked to the carbon atom adjacent to $R^5$ to form an epoxy or thioepoxy ring;

$R^4$ is hydrogen, oxo, halogen, thio, phosphate, sulfoxide, sulfone, deuterium, hydroxy, loweralkylsiloxane, carboxyl, aldehyde, hydroxyloweralkyl, alkoxyloweralkyl, loweralkoxy carbonyl, loweracyloxyloweralkyl, acetylloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, cycloalkyl or cycloalkoxy having from 4 to 6 carbon atoms which is optionally substituted by loweralkyl, halogen, oxygen, hydroxy or loweralkoxy;

and when $R^4$ is oxo or thio, $R^4$ may be linked to the carbon atom adjacent to $R^5$ to form an epoxy or thioepoxy ring;

$R^5$ is carboxyl, hydroxy, aldehyde, hydroxyloweralkyl, alkoxyloweralkyl, loweralkoxycarbonyl, loweracyloxyloweralkyl, acetylloweralkyl, acetoxyloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, hydrogen, oxo, thio, phosphate, sulfoxide, sulfone or deuterium, and when $R^5$ is oxo, it may be linked to the carbon atom bearing $R^3$;

$R^6$ is loweralkyl, hydrogen, oxo, hydroxyloweralkyl, loweralkoxy, halogen, thio, sulfoxide, sulfone, phosphate or deuterium;

$R^7$ is carboxyl, hydroxy, aldehyde, hydroxyloweralkyl, alkoxyloweralkyl, loweralkoxycarbonyl, loweracyloxyloweralkyl, acetylloweralkyl, acetoxyloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, hydrogen, oxo, thio, phosphate, sulfoxide, sulfone or deuterium, and when $R^7$ is oxo, it may be linked to the carbon atom bearing $R^3$; and wherein the dotted lines may each represent a single bond and the double dotted line represents either a double bond or a triple bond, $R^1$ or $R^6$ is absent if the dotted line adjacent to $R^1$ and $R^6$ is a single bond, $R^2$ is absent if either of the dotted lines adjacent to $R^2$ is a single bond, the alkyl group bearing $R^7$ is absent if the dotted line adjacent to the alkyl group bearing $R^7$ is a single bond, and isomers and functional derivatives thereof, in admixture with an acceptable agricultural carrier comprising an agriculturally acceptable carrier cation when R, $R^1$, $R^2$, $R^4$, $R^5$, $R^6$ or $R^7$ are phosphate, sulfoxide or sulfone.

The compositions of the present invention can be applied in combination with other fungicides and/or other growth regulators such as auxins, ethylene, gibberellins, cytokinins and brassinolides to form agricultural solutions having germination enhancing properties and promoting synchrony of germination and emergence in plants.

Most of the compounds comprised in the compositions of the present invention can be synthesized in short efficient sequences from inexpensive starting materials. The structures and stereochemistry of the synthesized compounds can then be easily established.

Also within the scope of the present invention is a compound having the following formula (I):

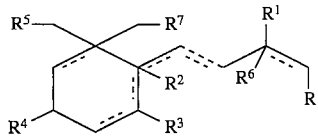

(I)

wherein

R is carboxyl, aldehyde, hydroxy, hydroxyloweralkyl, alkoxyloweralkyl, loweralkoxycarbonyl, loweracyloxyloweralkyl, acetylloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, thio, phosphate, sulfoxide, sulfone, deuterium or cycloalkyl or cycloalkoxy having from 4 to 6 carbon atoms which is optionally substituted by loweralkyl, halogen, oxygen, hydroxy or loweralkoxy;

$R^1$ is loweralkyl, hydrogen, oxo, hydroxyloweralkyl, loweralkoxy, halogen, thio, sulfoxide, sulfone, phosphate or deuterium;

$R^2$ is hydrogen, oxo, hydroxy, halogen, thio, phosphate, sulfoxide, sulfone or deuterium;

$R^3$ is oxo, thio, carboxyl, aldehyde, loweralkyl, hydroxyloweralkyl, alkoxyloweralkyl, loweralkoxycarbonyl, loweracyloxy- loweralkyl, acetylloweralkyl, loweralkanoyl, loweralkylamino, diloweralkylamino, loweralkoxy, loweracyloxy, loweralkylthio, loweralkylhalide, loweralkyldeuterium, loweralkyl sulphonyl, loweralkyl sulphinyl, or carbonyl;

when $R^2$ is oxo or thio, $R^2$ may be linked to both $C^1$ and $C^2$ carbon atoms to form an epoxy or a thioepoxy ring; and when $R^3$ is oxo or thio, $R^3$ may be linked to the carbon atom adjacent to $R^5$ to form an epoxy or thioepoxy ring;

$R^4$ is hydrogen, oxo, halogen, thio, phosphate, sulfoxide, sulfone, deuterium, hydroxy, loweralkylsiloxane, carboxyl, aldehyde, hydroxyloweralkyl, alkoxyloweralkyl, loweralkoxycarbonyl, loweracyloxyloweralkyl, acetylloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, cycloalkyl or cycloalkoxy having from 4 to 6 carbon atoms which is optionally substituted by loweralkyl, halogen, oxygen, hydroxy or loweralkoxy;

and when $R^4$ is oxo or thio, $R^4$ may be linked to the carbon atom adjacent to $R^5$ to form an epoxy or thioepoxy ring;

$R^5$ is carboxyl, hydroxy, aldehyde, hydroxyloweralkyl, alkoxyloweralkyl, loweralkoxycarbonyl, loweracyloxyloweralkyl, acetylloweralkyl, acetoxyloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, hydrogen, oxo, thio, phosphate, sulfoxide, sulfone or deuterium, and when $R^5$ is oxo, it may be linked to the carbon atom bearing $R^3$;

$R^6$ is loweralkyl, hydrogen, oxo, hydroxyloweralkyl, loweralkoxy, halogen, thio, sulfoxide, sulfone, phosphate or deuterium;

$R^7$ is carboxyl, hydroxy, aldehyde, hydroxyloweralkyl, alkoxyloweralkyl, loweralkoxycarbonyl, loweracyloxyloweralkyl, acetylloweralkyl, acetoxyloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, hydrogen, oxo, thio, phosphate, sulfoxide, sulfone or deuterium, and when $R^7$ is oxo, it may be linked to the carbon atom bearing $R^3$;

and wherein the dotted lines may each represent a single bond and the double dotted line represents either a double bond or a triple bond, $R^1$ or $R^6$ is absent if the dotted line adjacent to $R^1$ and $R^6$ is a single bond, $R^2$ is absent if either of the dotted lines adjacent to $R^2$ is a single bond, the alkyl group bearing $R^7$ is absent if the dotted line adjacent to the alkyl group bearing $R^7$ is a single bond, and isomers and functional derivatives thereof, with the proviso that when R is —CHO, —CH$_2$OH or —COOCH$_3$, $R^1$ is CH$^3$, $R^2$ is oxo or OH, $R^3$ is CH$_3$, $R^4$ is oxo or H and $R^5$ is H, the following compounds are excluded from formula (IA):

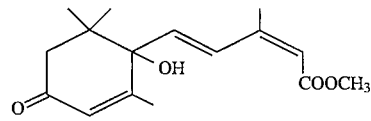

PBI-01

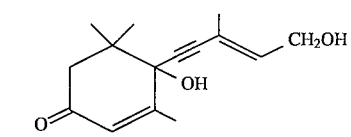

PBI-04

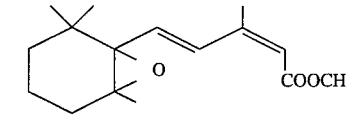

PBI-06

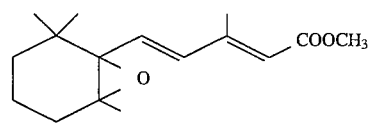

PBI-07

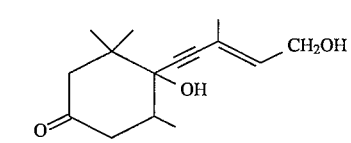

PBI-10

5
-continued

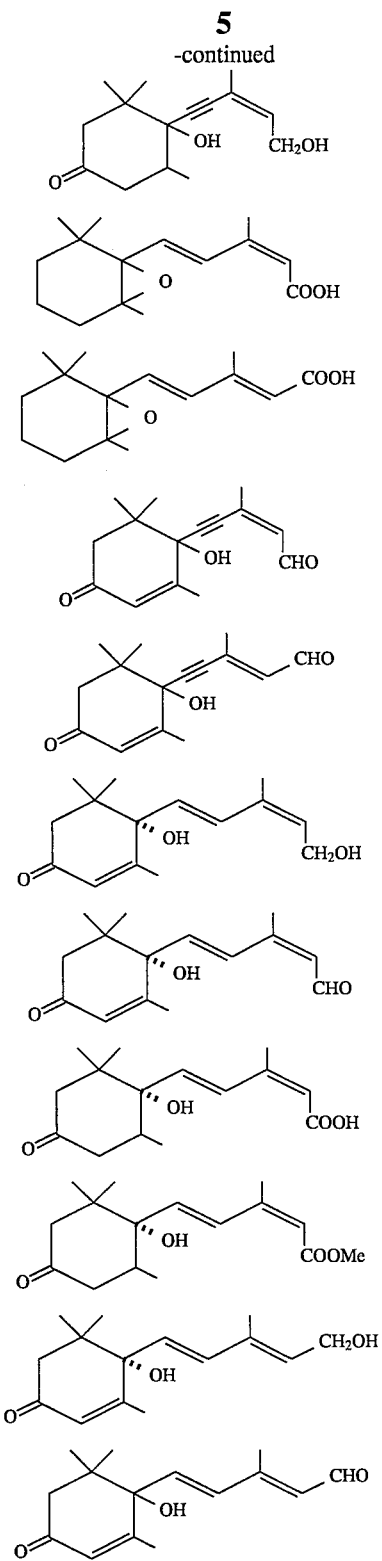

PBI-11

PBI-14

PBI-15

PBI-16

PBI-17

PBI-31

PBI-37

PBI-38

PBI-39

PBI-46

PBI-47

Furthermore, the present invention relates to a method for promoting synchrony of germination and emergence in plants. The method comprises treating plant seeds or plant parts used in propagation with an effective amount of a solution comprising a compound having the following formula (I):

6

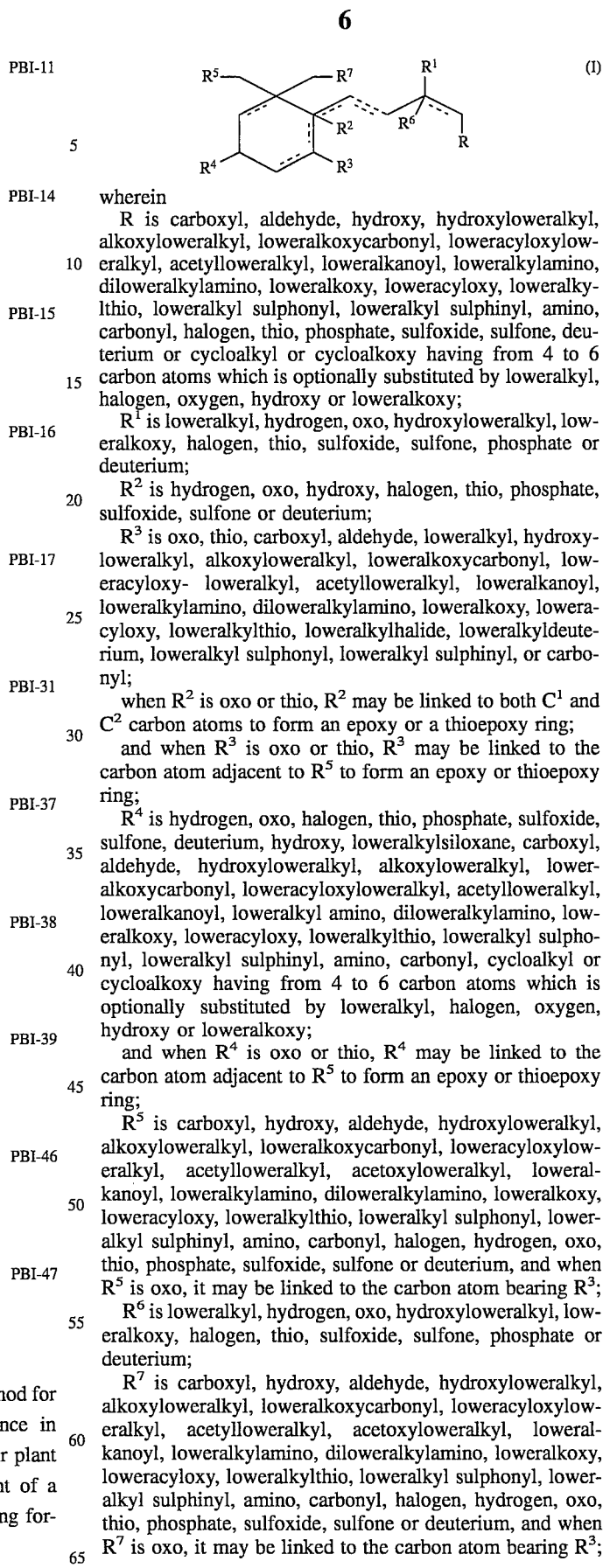

wherein

R is carboxyl, aldehyde, hydroxy, hydroxyloweralkyl, alkoxyloweralkyl, loweralkoxycarbonyl, loweracyloxyloweralkyl, acetylloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, thio, phosphate, sulfoxide, sulfone, deuterium or cycloalkyl or cycloalkoxy having from 4 to 6 carbon atoms which is optionally substituted by loweralkyl, halogen, oxygen, hydroxy or loweralkoxy;

$R^1$ is loweralkyl, hydrogen, oxo, hydroxyloweralkyl, loweralkoxy, halogen, thio, sulfoxide, sulfone, phosphate or deuterium;

$R^2$ is hydrogen, oxo, hydroxy, halogen, thio, phosphate, sulfoxide, sulfone or deuterium;

$R^3$ is oxo, thio, carboxyl, aldehyde, loweralkyl, hydroxyloweralkyl, alkoxyloweralkyl, loweralkoxycarbonyl, loweracyloxy- loweralkyl, acetylloweralkyl, loweralkanoyl, loweralkylamino, diloweralkylamino, loweralkoxy, loweracyloxy, loweralkylthio, loweralkylhalide, loweralkyldeuterium, loweralkyl sulphonyl, loweralkyl sulphinyl, or carbonyl;

when $R^2$ is oxo or thio, $R^2$ may be linked to both $C^1$ and $C^2$ carbon atoms to form an epoxy or a thioepoxy ring;

and when $R^3$ is oxo or thio, $R^3$ may be linked to the carbon atom adjacent to $R^5$ to form an epoxy or thioepoxy ring;

$R^4$ is hydrogen, oxo, halogen, thio, phosphate, sulfoxide, sulfone, deuterium, hydroxy, loweralkylsiloxane, carboxyl, aldehyde, hydroxyloweralkyl, alkoxyloweralkyl, loweralkoxycarbonyl, loweracyloxyloweralkyl, acetylloweralkyl, loweralkanoyl, loweralkyl amino, diloweralkylamino, loweralkoxy, loweracyloxy, loweralkylthio, loweralkyl sulphonyl, loweralkyl sulphinyl, amino, carbonyl, cycloalkyl or cycloalkoxy having from 4 to 6 carbon atoms which is optionally substituted by loweralkyl, halogen, oxygen, hydroxy or loweralkoxy;

and when $R^4$ is oxo or thio, $R^4$ may be linked to the carbon atom adjacent to $R^5$ to form an epoxy or thioepoxy ring;

$R^5$ is carboxyl, hydroxy, aldehyde, hydroxyloweralkyl, alkoxyloweralkyl, loweralkoxycarbonyl, loweracyloxyloweralkyl, acetylloweralkyl, acetoxyloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, hydrogen, oxo, thio, phosphate, sulfoxide, sulfone or deuterium, and when $R^5$ is oxo, it may be linked to the carbon atom bearing $R^3$;

$R^6$ is loweralkyl, hydrogen, oxo, hydroxyloweralkyl, loweralkoxy, halogen, thio, sulfoxide, sulfone, phosphate or deuterium;

$R^7$ is carboxyl, hydroxy, aldehyde, hydroxyloweralkyl, alkoxyloweralkyl, loweralkoxycarbonyl, loweracyloxyloweralkyl, acetylloweralkyl, acetoxyloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, hydrogen, oxo, thio, phosphate, sulfoxide, sulfone or deuterium, and when $R^7$ is oxo, it may be linked to the carbon atom bearing $R^3$;

and wherein the dotted lines may each represent a single bond and the double dotted line represents either a double bond or a triple bond, $R^1$ or $R^6$ is absent if the dotted line adjacent to $R^1$ and $R^6$ is a single bond, $R^2$ is absent if either of the dotted lines adjacent to $R^2$ is a single bond, the alkyl group bearing $R^7$ is absent if the dotted line adjacent to the alkyl group bearing $R^7$ is a single bond, and isomers and functional derivatives thereof, in admixture with an acceptable agricultural carrier comprising an agriculturally acceptable carrier cation when R, $R^1$, $R^2$, $R^4$, $R^5$, $R^6$ or $R^7$ are phosphate, sulfoxide or sulfone, for the purpose of enhancing synchrony of germination and emergence in plants.

Also within the scope of the present invention is a plant seed treated with the agricultural composition referred to above. A plant treated with the agricultural composition referred to above also falls within the scope of the present invention.

IN THE DRAWINGS

Figure 1:
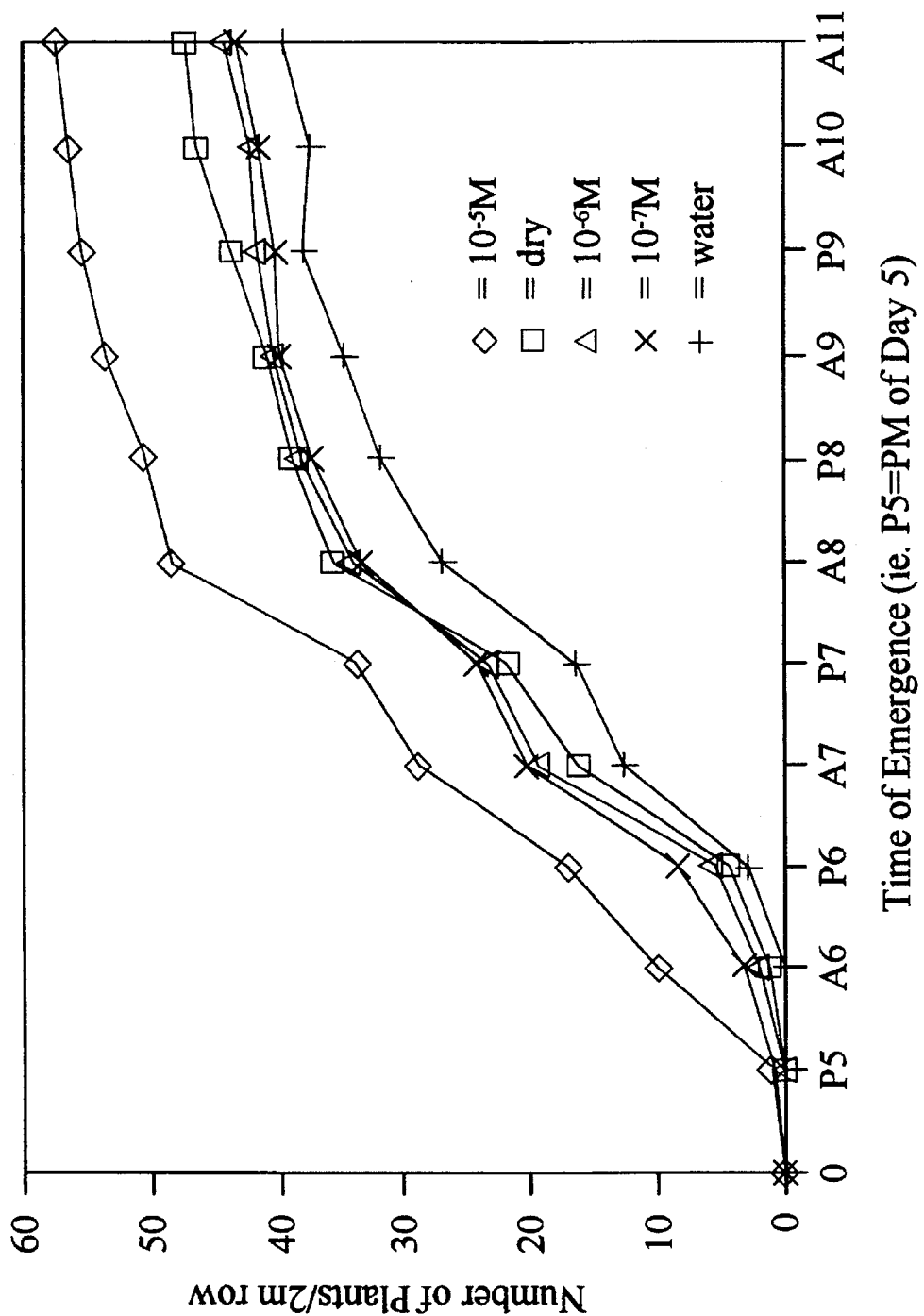
FIG. 1 represents the influence of various concentrations of compound PBI-11 on the synchrony of germination and emergence of Tobin canola.

As used herein, the term halogen includes chlorine, bromine, iodine and fluorine. The terms loweralkyl, loweracyloxyloweralkyl, loweralkanoyl, loweralkoxycarbonyl, loweralkoxy and loweracyloxy, wherever employed, include straight and branched alkyl, acyloxyloweralkyl, alkanoyl, alkoxy and acyloxy groups having 1 to 10 carbon atoms in the alkyl, acyloxyloweralkyl, alkanoyl, alkoxycarbonyl, alkoxy or acyloxy moiety.

DETAILED DESCRIPTION OF THE INVENTION

The invention relates to compounds which, when applied to seeds or plant parts used in propagation, are useful to promote synchrony of germination and emergence in plants. As the compounds used in the context of the present invention also have the ability to promote germination, synchrony of germination and emergence can be achieved without delaying germination.

Agricultural compositions comprising compounds promoting synchrony of germination and emergence The composition useful to promote synchrony of germination and emergence in plants comprises a compound having the following formula (I):

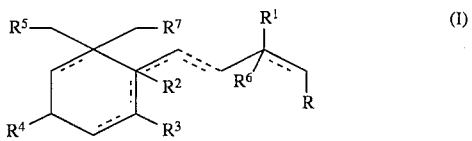

wherein

R is carboxyl, aldehyde, hydroxy, hydroxyloweralkyl, alkoxyloweralkyl, loweralkoxycarbonyl, loweracyloxyloweralkyl, acetylloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, thio, phosphate, sulfoxide, sulfone, deuterium or cycloalkyl or cycloalkoxy having from 4 to 6 carbon atoms which is optionally substituted by loweralkyl, halogen, oxygen, hydroxy or loweralkoxy;

$R^1$ is loweralkyl, hydrogen, oxo, hydroxyloweralkyl, loweralkoxy, halogen, thio, sulfoxide, sulfone, phosphate or deuterium;

$R^2$ is hydrogen, oxo, hydroxy, halogen, thio, phosphate, sulfoxide, sulfone or deuterium;

$R^3$ is oxo, thio, carboxyl, aldehyde, loweralkyl, hydroxyloweralkyl, alkoxyloweralkyl, loweralkoxycarbonyl, loweracyloxyloweralkyl, acetylloweralkyl, loweralkanoyl, loweralkylamino, diloweralkylamino, loweralkoxy, loweracyloxy, loweralkylthio, loweralkylhalide, loweralkyldeuterium, loweralkyl sulphonyl, loweralkyl sulphinyl, or carbonyl;

when $R^2$ is oxo or thio, $R^2$ may be linked to both $C^1$ and $C^2$ carbon atoms to form an epoxy or a thioepoxy ring;

and when $R^3$ is oxo or thio, $R^3$ may be linked to the carbon atom adjacent to $R^5$ to form an epoxy or thioepoxy ring;

$R^4$ is hydrogen, oxo, halogen, thio, phosphate, sulfoxide, sulfone, deuterium, hydroxy, loweralkylsiloxane, carboxyl, aldehyde, hydroxyloweralkyl, alkoxyloweralkyl, loweralkoxycarbonyl, loweracyloxyloweralkyl, acetylloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, cycloalkyl or cycloalkoxy having from 4 to 6 carbon atoms which is optionally substituted by loweralkyl, halogen, oxygen, hydroxy or loweralkoxy;

and when $R^4$ is oxo or thio, $R^4$ may be linked to the carbon atom adjacent $R^5$ to form an epoxy or thioepoxy ring;

$R^5$ is carboxyl, hydroxy, aldehyde, hydroxyloweralkyl, alkoxyloweralkyl, loweralkoxycarbonyl, loweracyloxyloweralkyl, acetylloweralkyl, acetoxyloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, hydrogen, oxo, thio, phosphate, sulfoxide, sulfone or deuterium, and when $R^5$ is oxo, it may be linked to the carbon atom bearing $R^3$;

$R^6$ is loweralkyl, hydrogen, oxo, hydroxyloweralkyl, loweralkoxy, halogen, thio, sulfoxide, sulfone, phosphate or deuterium;

$R^7$ is carboxyl, hydroxy, aldehyde, hydroxyloweralkyl, alkoxyloweralkyl, loweralkoxycarbonyl, loweracyloxyloweralkyl, acetylloweralkyl, acetoxyloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, hydrogen, oxo, thio, phosphate, sulfoxide, sulfone or deuterium, and when $R^7$ is oxo, it may be linked to the carbon atom bearing $R^3$;

and wherein the dotted lines may each represent a single bond and the double dotted line represents either a double bond or a triple bond, $R^1$ or $R^6$ is absent if the dotted line adjacent to $R^1$ and $R^6$ is a single bond, $R^2$ is absent if either of the dotted lines adjacent to $R^2$ is a single bond, the alkyl group bearing $R^7$ is absent if the dotted line adjacent to the alkyl group bearing $R^7$ is a single bond, and isomers and functional derivatives thereof, in admixture with an acceptable agricultural carrier comprising an agriculturally acceptable carrier cation when R, $R^1$, $R^2$, $R^4$, $R^5$, $R^6$ or $R^7$ are phosphate, sulfoxide or sulfone.

The composition is used to enhance synchrony of germination and emergence in plants by being applied to seeds or plant parts used in propagation in concentrations sufficient to achieve the desired effect.

Preferred embodiments falling within this generic class include the following compounds:

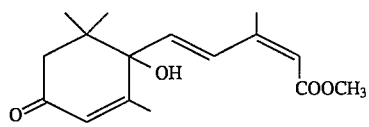
PBI-01

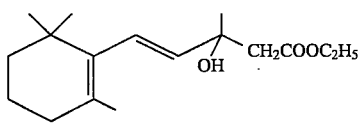
PBI-02

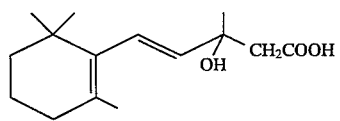
PBI-03

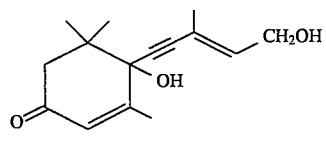
PBI-04

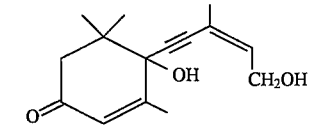
PBI-05

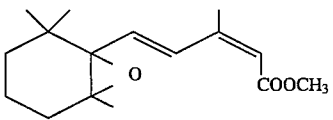
PBI-06

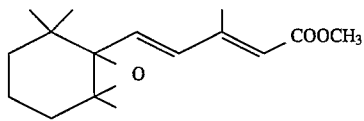
PBI-07

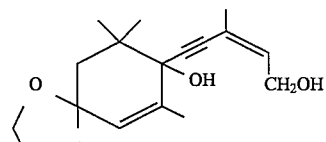
PBI-08

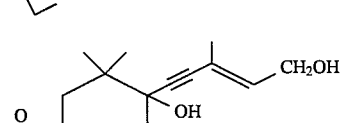
PBI-09

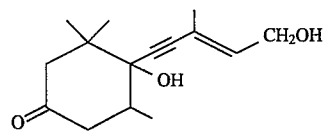
PBI-10

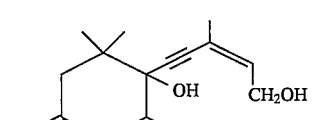
PBI-11

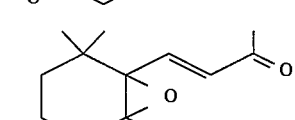
PBI-12

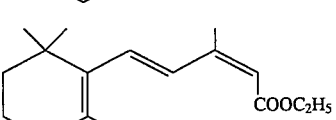
PBI-13

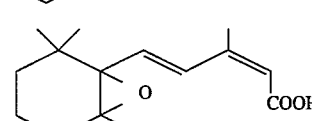
PBI-14

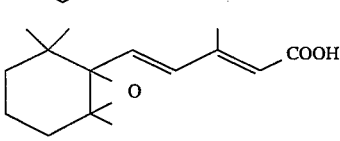
PBI-15

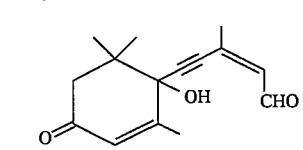
PBI-16

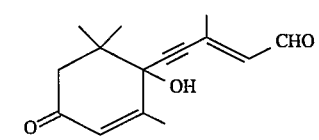
PBI-17

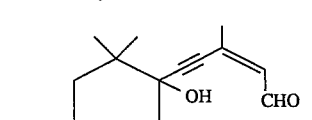
PBI-18

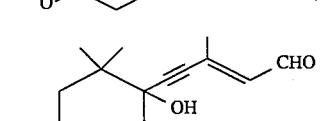
PBI-19

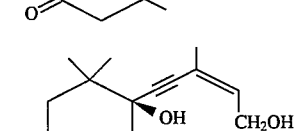
PBI-20

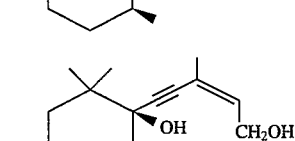
PBI-21

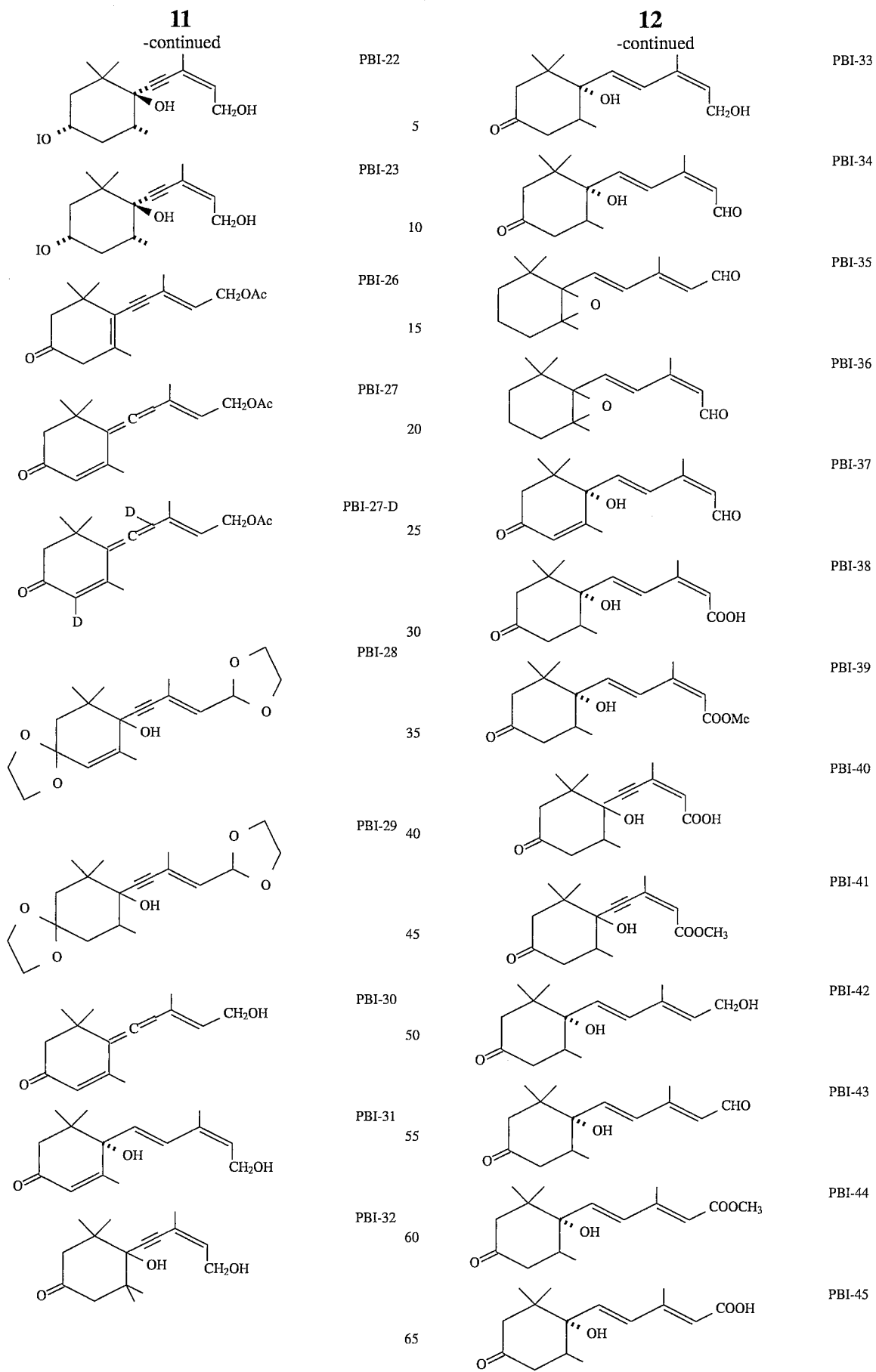

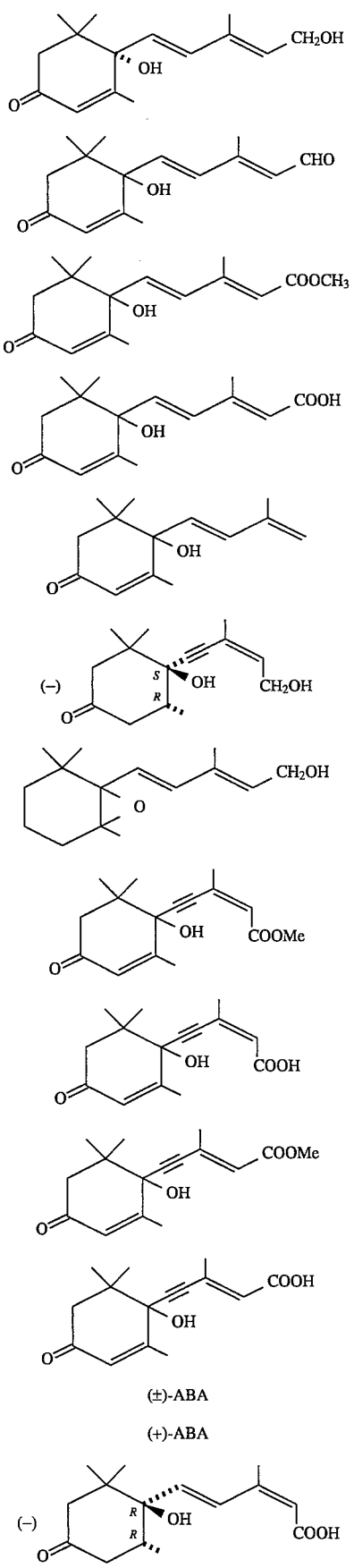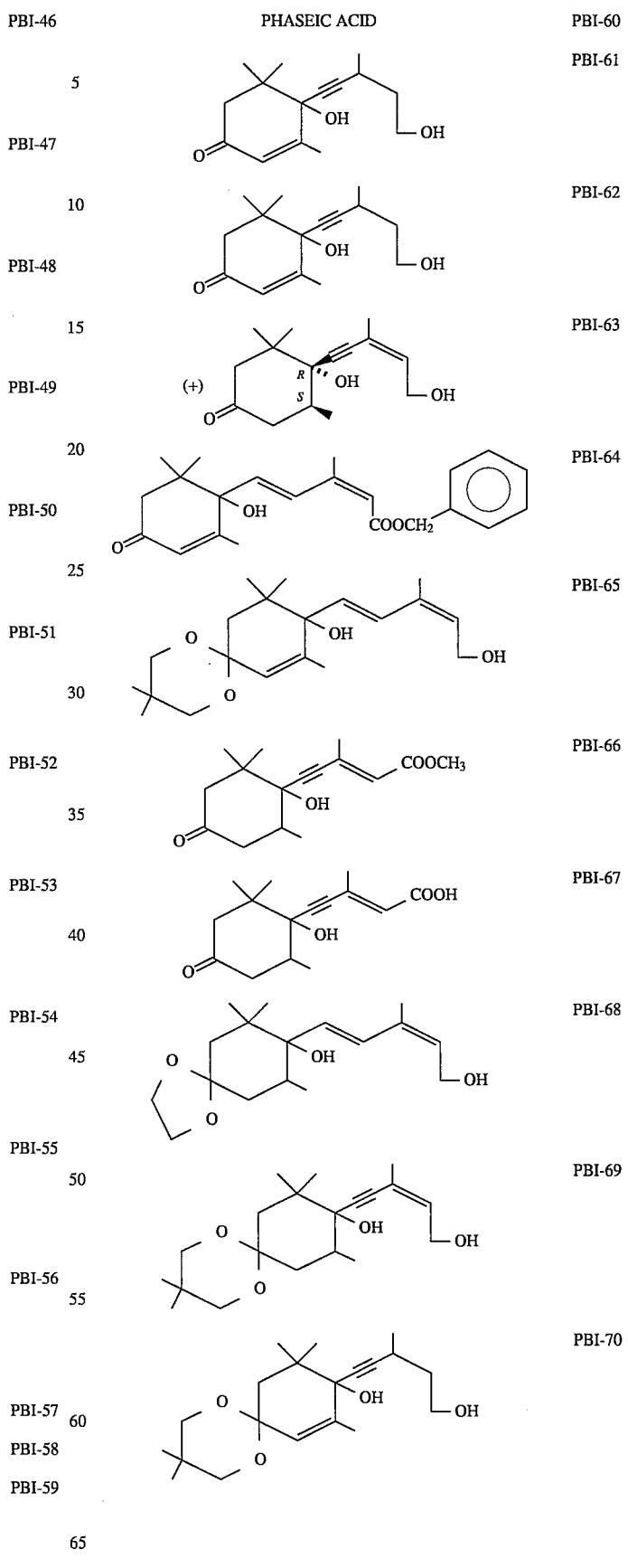

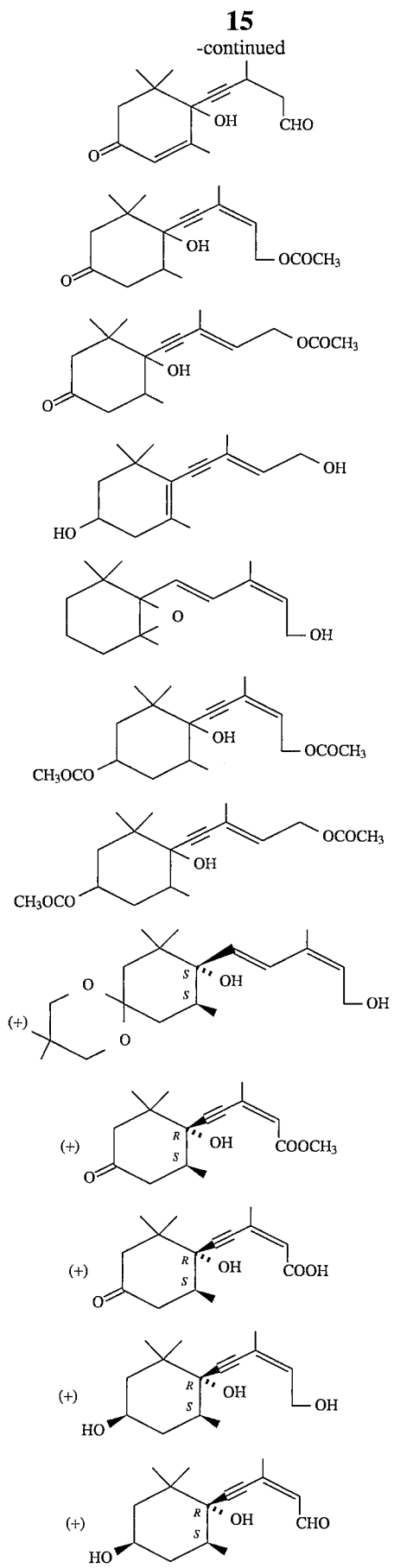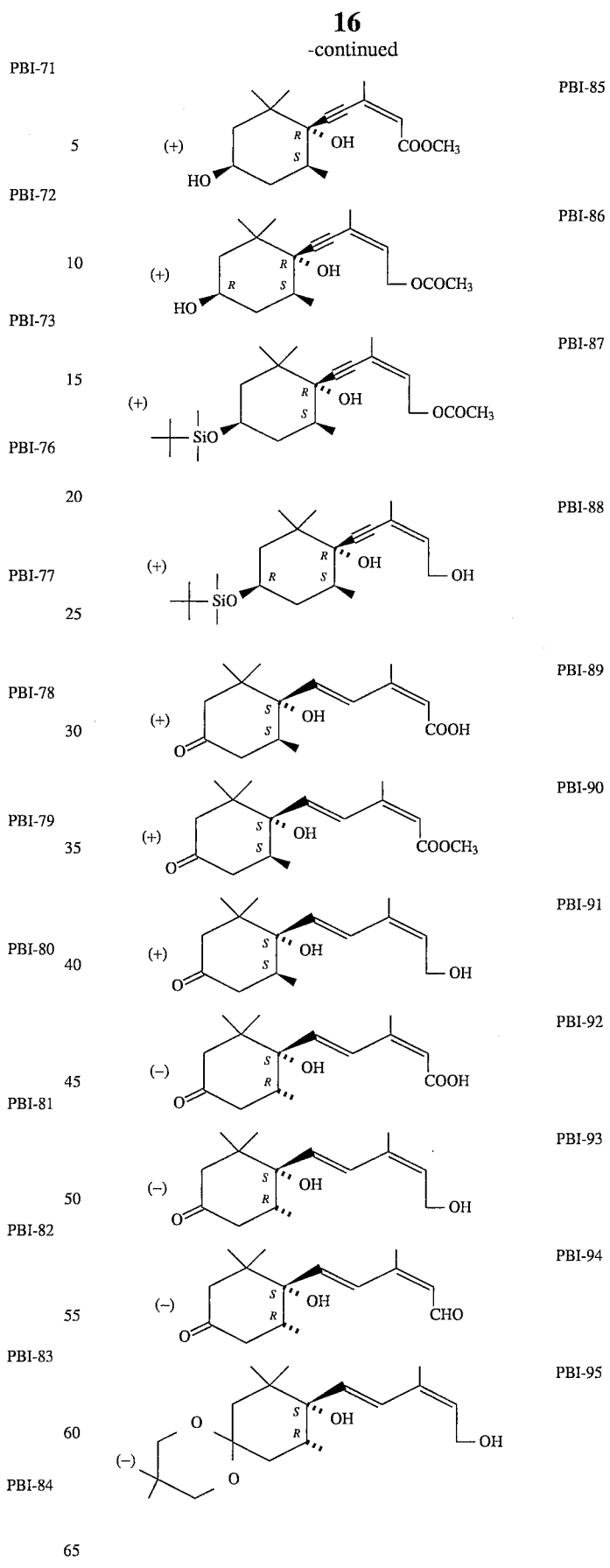

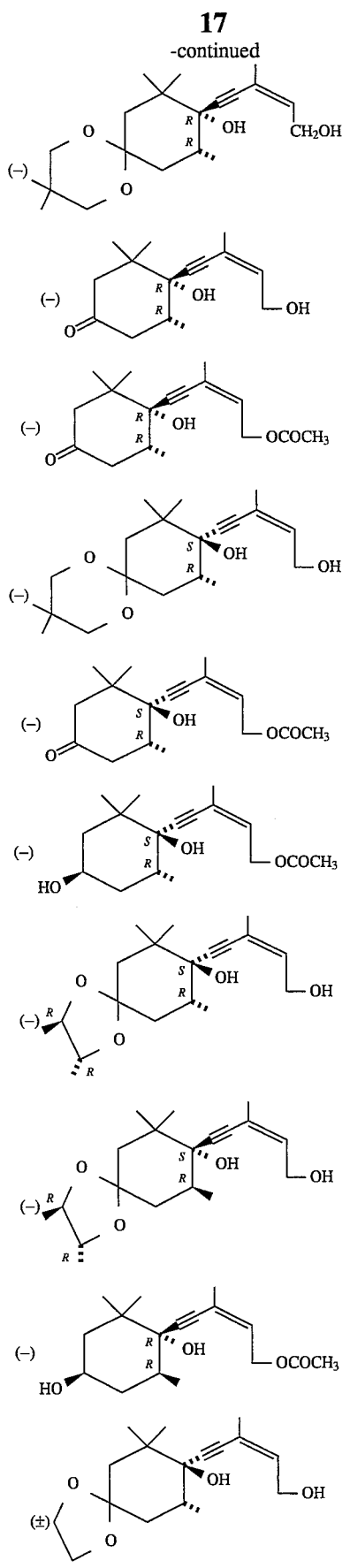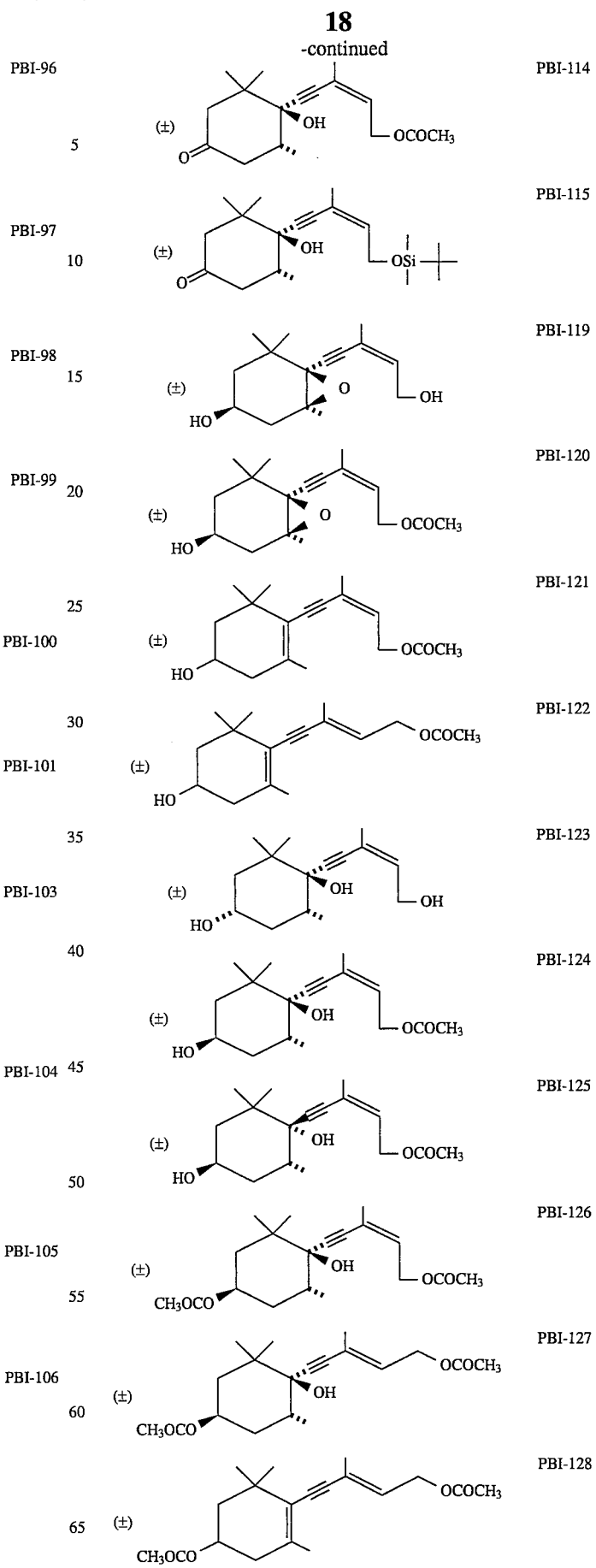

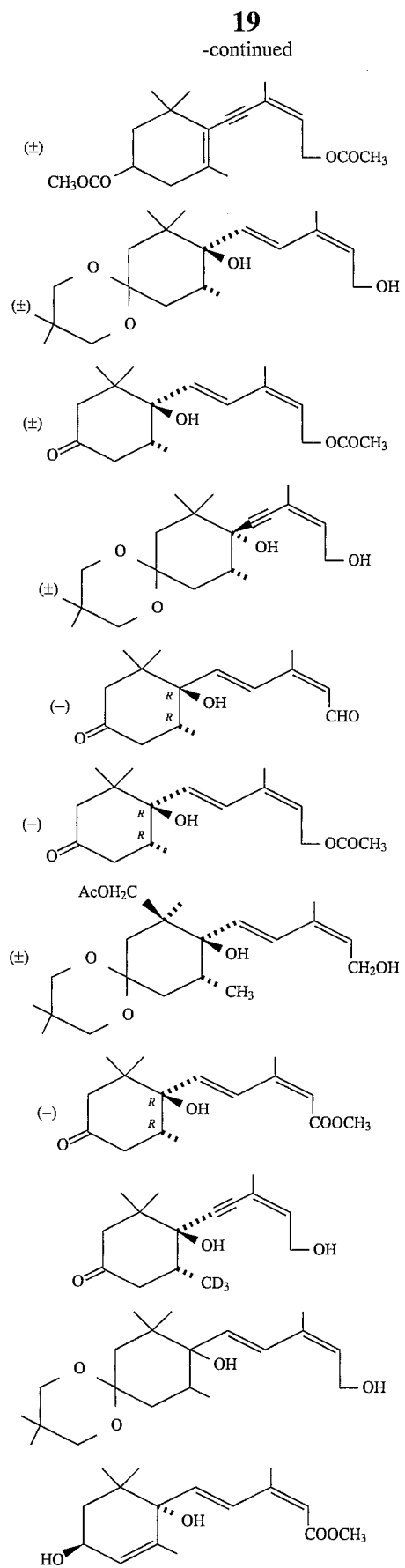
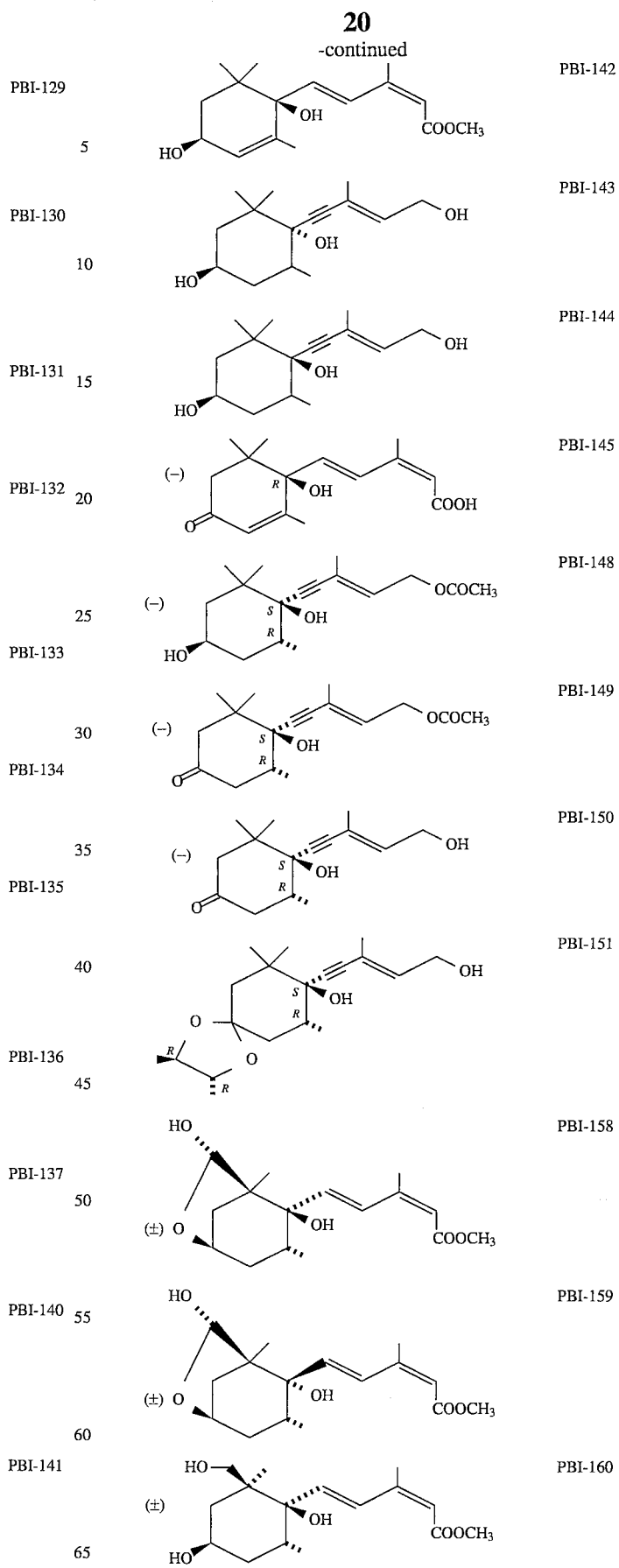

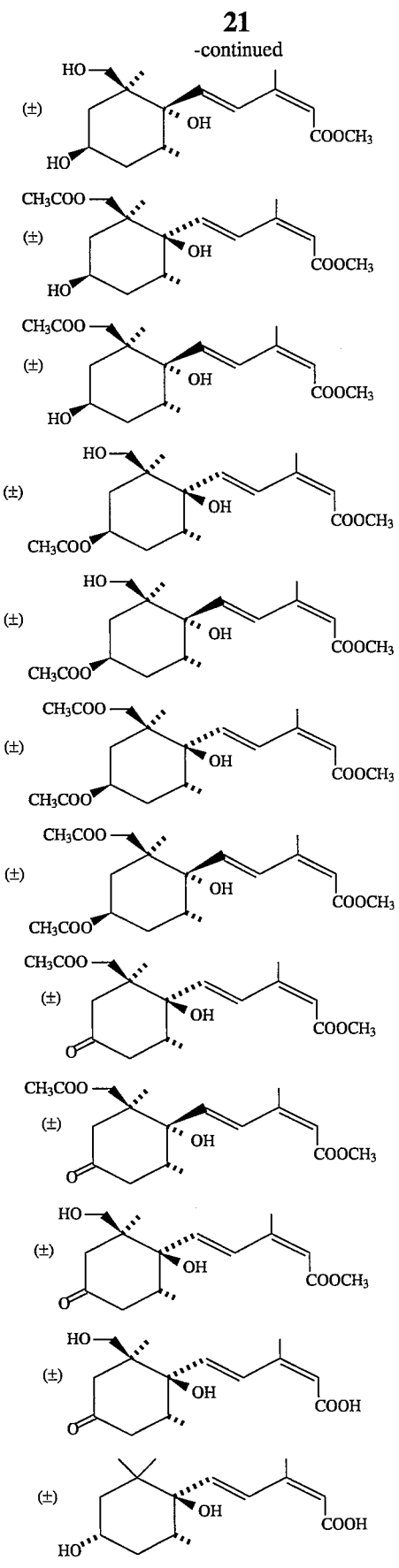

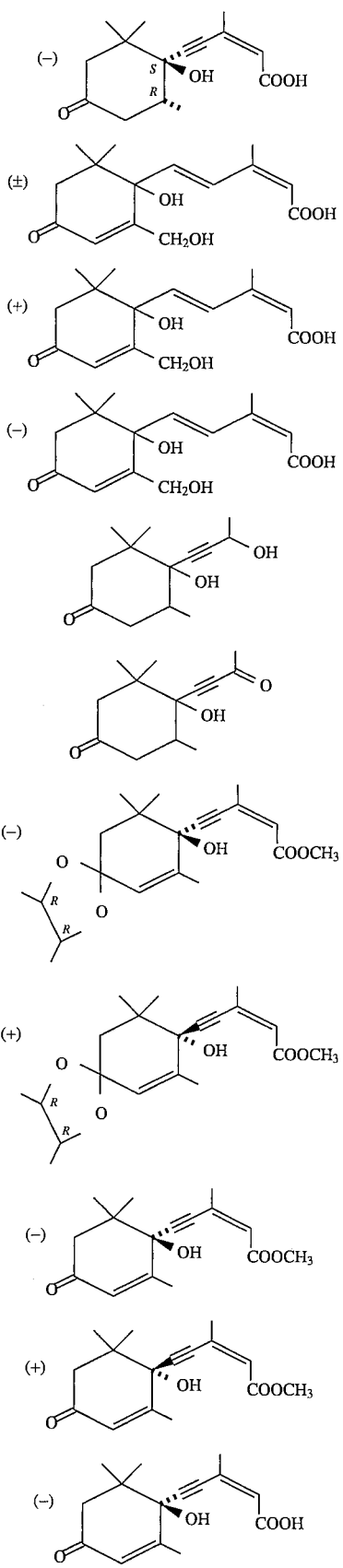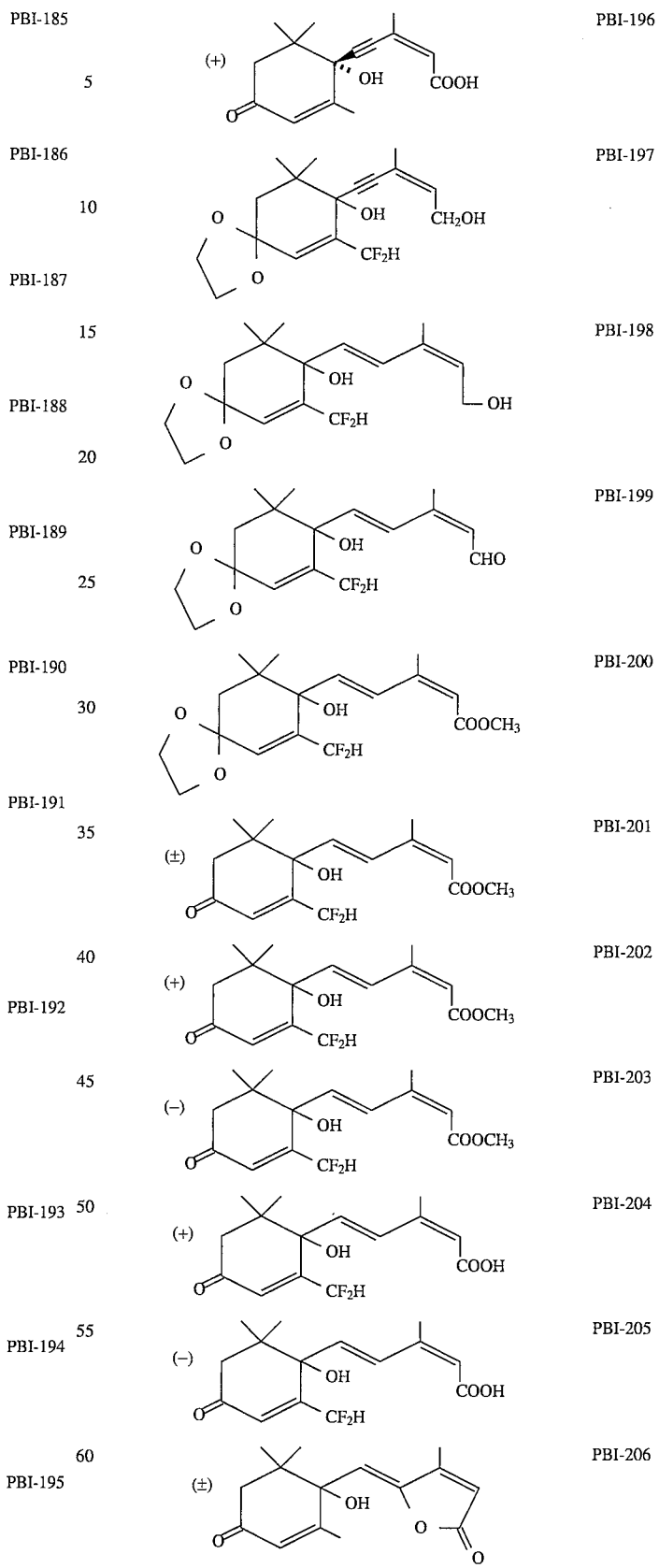

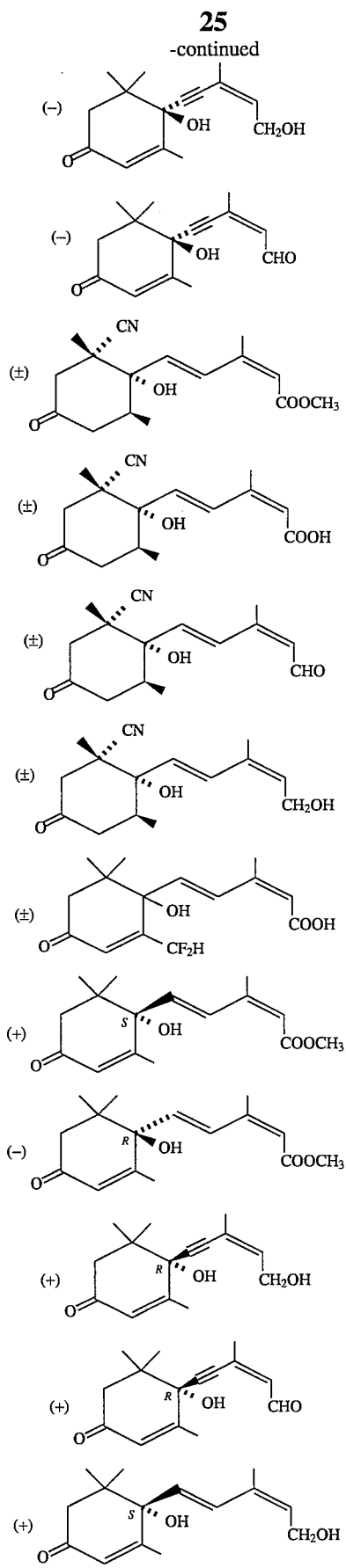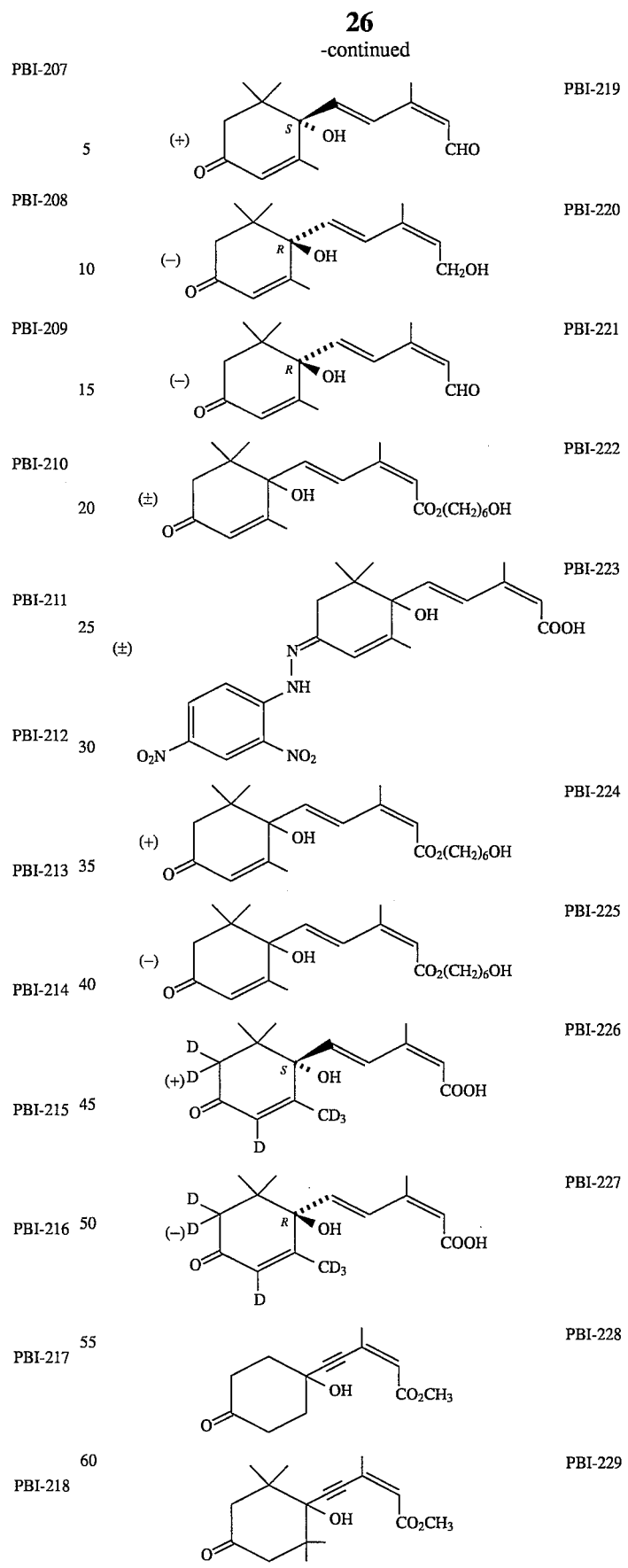

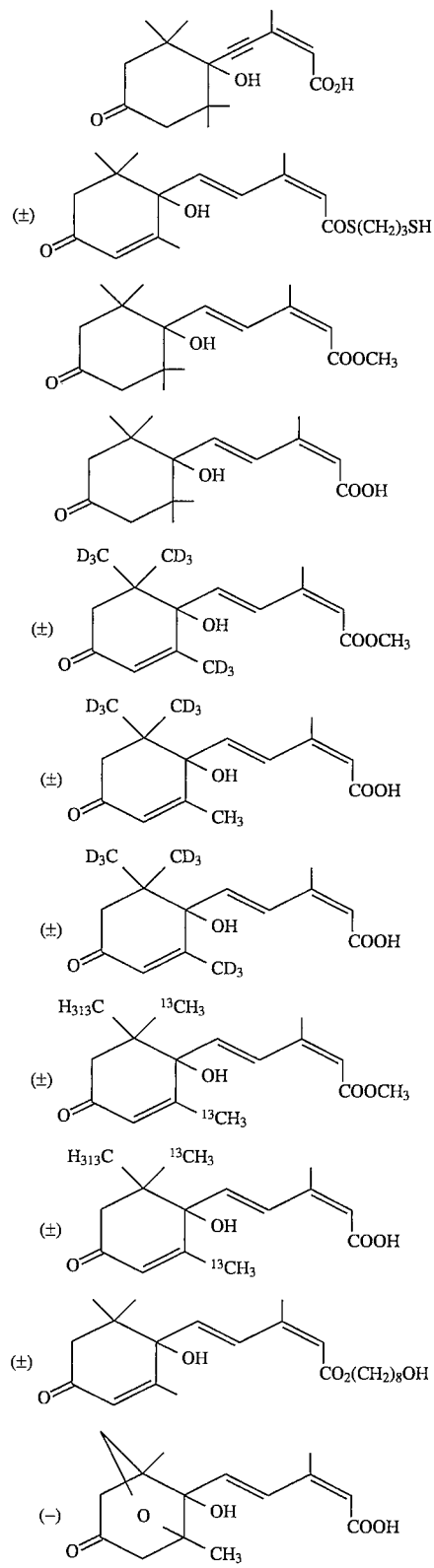
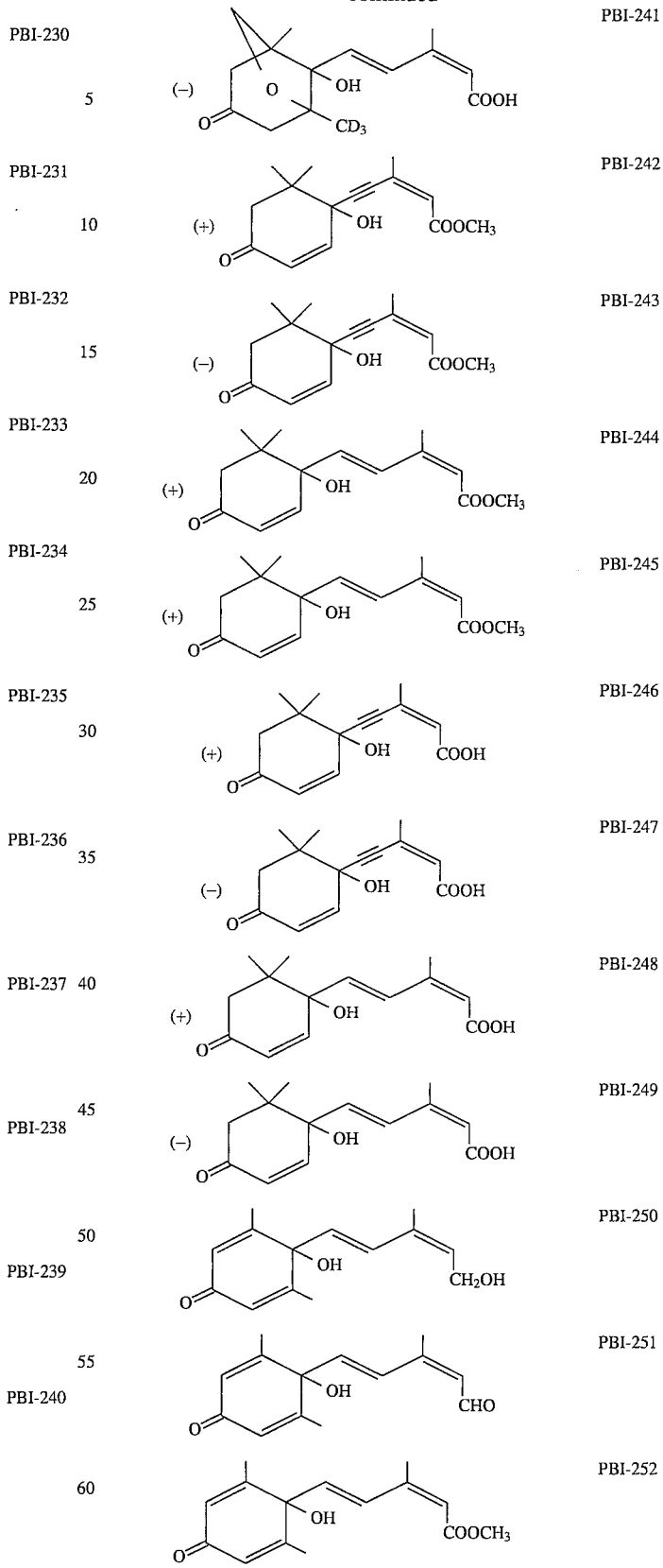

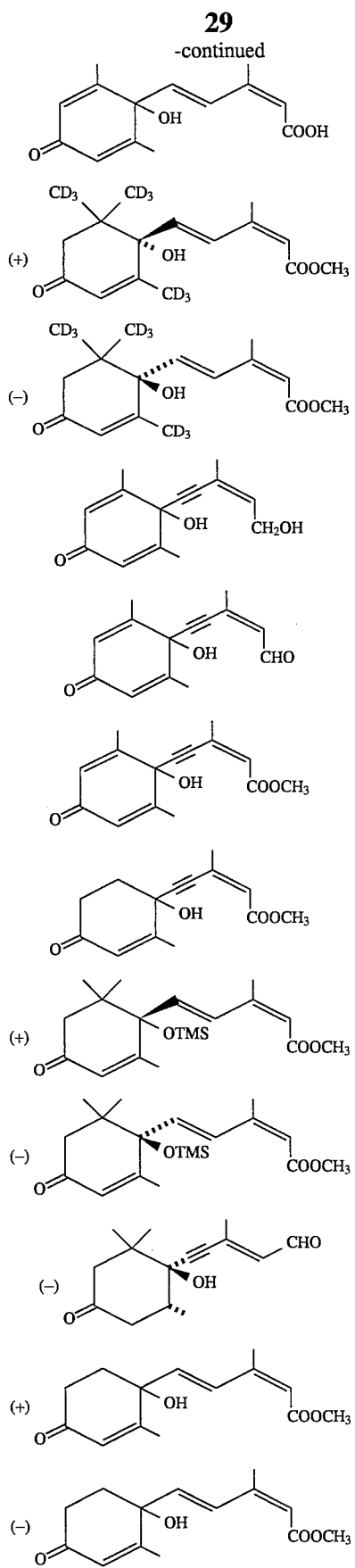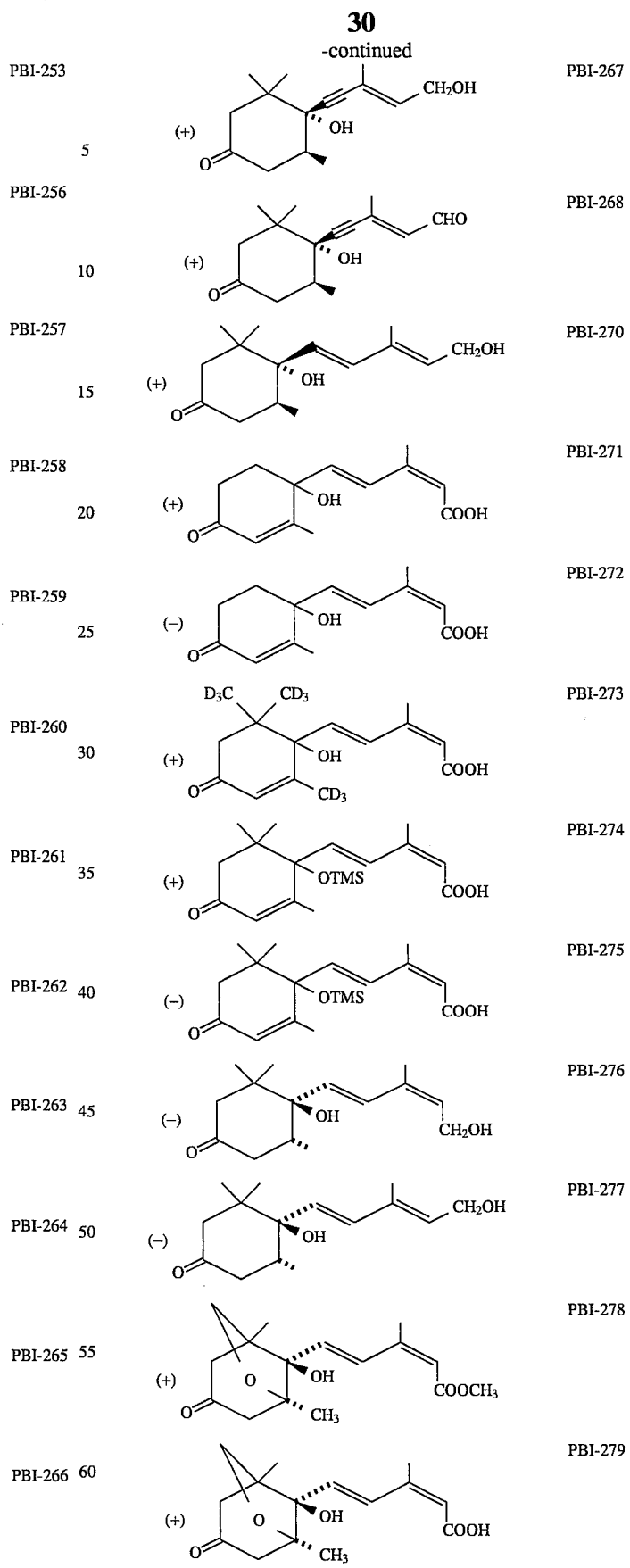

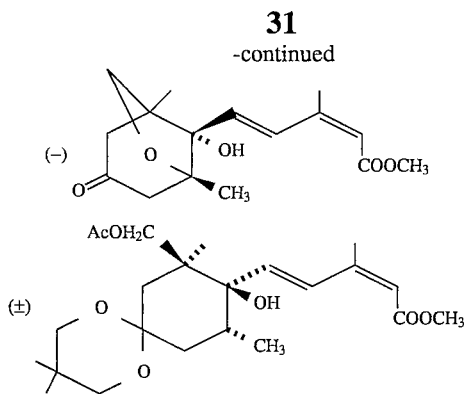

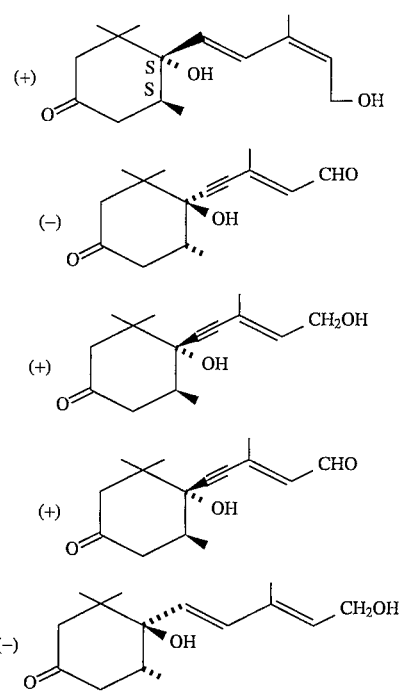

A preferred group of the formula I compounds are those in which

R is carboxyl, aldehyde, hydroxy, hydroxyloweralkyl, alkoxyloweralkyl, loweralkoxycarbonyl, loweracyloxyloweralkyl, acetylloweralkyl, loweralkanoyl, cycloalkyxo having from 4 to 6 carbon atoms, amino, carbonyl, halogen or thio;

$R^1$ is loweralkyl, hydrogen, oxo, hydroxyloweralkyl, loweralkoxy, halogen, thio, sulfoxide, sulfone, phosphate or deuterium;

$R^2$ is hydrogen, hydroxy, halogen or thio;

$R^3$ is carboxyl, aldehyde, loweralkyl, hydroxyloweralkyl, alkoxyloweralkyl, loweralkoxycarbonyl, loweracyloxyloweralkyl, acetylloweralkyl, loweralkanoyl, loweralkylamino, diloweralkylamino, loweralkoxy, loweralkylhalide, loweracyloxy, loweralkylthio, loweralkyl sulphonyl, loweralkyl sulphinyl or carbonyl;

and when $R^2$ is thio, $R^2$ may be linked to both $C_1$ and $C_2$ carbon atoms to form a thioepoxy ring;

$R^4$ is hydrogen, oxo, halogen, thio or amino;

$R^5$ is hydrogen, oxo or nitrogen;

$R^6$ is hydrogen;

$R^7$ is hydrogen, oxo or nitrogen.

A more preferred group of compounds to be used in the composition of the present invention include those having the following formula IA:

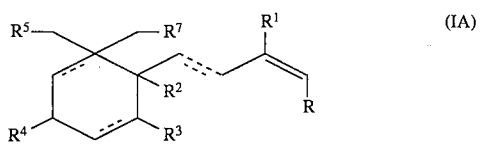

wherein

R is hydroxy, aldehyde, hydroxyloweralkyl, alkoxyloweralkyl, carboxyl or loweralkoxyl;

$R^1$ is loweralkyl;

$R^2$ is hydroxy;

$R^3$ is loweralkyl or loweralkylhalide;

$R^4$ is oxo;

$R^5$ and $R^7$ are hydrogen; the dotted line is optionally a single bond and the double dotted line is a double bond or a triple bond; and $R^7$ is absent when the dotted line adjacent to $R^5$ is a single bond.

Of particular interest for use in the composition of the present invention are the following compounds:

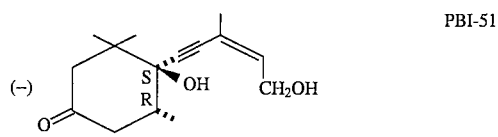

One may refer to the following publications that describe the synthesis of some of these and other compounds for which either racemic mixtures or a given isomer may be used: Agr. Biol. Chem. 46(3), 817–818, 1982, Agr Biol. Chem. Vol. 33, No. 2, p. 296–298 (1969), J. Chem. Soc. Pekin Trans. 1, 1984, 2147–2157, Planta 121: 263–272 (1974), Helv. Chim. Acta 59, 1424, (1976) and U.S. Pat. No. 4,153,615. The compounds can also be prepared by alkylation of an appropriate cyclohexanone derivative with an appropriate acetylide derivative. This method is well-known to those skilled in the art. The compounds represented in formula I shown above may therefore be combined with suitable agricultural carriers to provide compositions to be used for the treatment of plant seeds or plant parts used in propagation.

Some of the compounds used in the context of the present invention have chemical structures containing asymmetric carbon atoms, and therefore can be obtained as optical isomers. The present invention therefore intends to cover racemic mixtures as well as isolated optical isomers of the compounds of formulae I and IA, obtained through resolution techniques well-known to those skilled in the art. These isomers may also be obtained through appropriate chemical synthesis, some examples of which are set forth in the present application. Generally speaking, the compounds of formulae I and IA have been used as racemic mixtures unless otherwise indicated.

It will also be understood by those skilled in the art that the compounds having the general formula described above can be found as geometric isomers having cis or trans configuration with respect to the double bond in the carbon chain. Furthermore, although the stereoisomeric configurations have not been indicated in the formulae exemplified above, it is to be understood that all geometric isomers and stereoisomers of the compounds falling within the scope of formula I do fall within the scope of the present invention.

Application of the composition of the present invention to seeds and plant parts The composition of the present invention can be applied to seeds or plant parts using various vehicles to insure that the chemicals are active. The rate of application should be such that a sufficient amount of the composition containing the active ingredient is applied to the targeted plant part to obtain the desired plant response and increase in plant yield.

The rate of application depends on a number of factors, such as environmental conditions, type of crop and the like. It has also been found that timing and rate of application bear a relationship to one another and to the crop to which they are applied, such that the rate of application and the timing thereof bear a relationship to the yield increase. Also, it has been discovered that the activity of some of these compounds on plants is concentration dependent since the compounds seem to be interfering with the action of some of the plant's normal hormones. Furthermore, the tests performed in the field tend to demonstrate that the effects of the compositions of the present invention vary from one species to another depending on the nature and the concentration of the compound used. In other words, a given compound may possess germination enhancement properties in canola while another compounds may be active in wheat but not in canola. Hence, some of the compositions of the present invention are highly specific to certain plant species while others are highly specific to different plant species.

The compositions of the present invention can be applied in a steep process, as a spray or as a coating. They can also be applied in a paste mixture or through a coating process.

In the case of a spray mixture, the composition is usually applied at a rate of from about 0.000005 g to 1.5 kg per acre, in a total applied volume of from about 5 l to 100 l per acre.

In the case of a steep process, seeds are steeped in a solution having a concentration of the active compound ranging from 0.00000025 g/l to 0.50 g/l for a period of time that can vary from 0.1 to 24 hours. This period of time can exceed depending on species, cultivar and temperature. The steeping temperature usually falls between 10° and 30° C. The seeds are then dried down to about their original moisture content and planted under normal conditions. It is to be mentioned that steeping may be carried out in water or another solvent. The seedlings usually appear 12 to 96 hours earlier than in the case of normal conditions and the time required to achieve 50% germination can be reduced by 10 to 90% when compared to untreated controls for seeds that germinate within, for example, two weeks of planting. For seeds that germinate slowly such as dormant seeds, the composition of the present invention initiates germination. Also, increased total germination is observed. Preferably, seeds of carrots, celery, canola, wheat, corn, flax, barley, cress and various grasses may be imbibed for 0.1 to 24 hours at a temperature ranging from 10° to 25° C., then air dried to approximately 12% moisture content and sown in the field.

Hence, the use of the compositions of the present invention promotes the obtention of a shorter plant growth cycle. For example, plants grown from seeds imbibed with the composition of the present invention mature faster than plants grown from untreated seeds.

Thus, the compounds of the present invention are useful as seed treatment for agronomic, forestry and horticultural crops. As well, these compounds are useful in the malting and distilling industry, where high alpha-amylase activity in germinating barley is required.

The present invention will be more readily illustrated by referring to the following examples which are introduced only to illustrate rather than limit the scope of the present disclosure.

EXAMPLE 1

Preparation of
(3E)-4-(5-acetoxy-3-methyl-1,3-pentadien-1-ylidene)-3,5,5-trimethyl-2-cyclohexen-1-one
(PBI-27)

A solution of (2E)-5-(4-oxo-1-hydroxy-2,2,6-trimethylcyclohexyl)- 3-methylpent-2-en-4-yn-1-ol (570 mg, 2.3 mmol) and potassium hydrogen sulfate (approx. 20 mg) in acetic acid (3.0 ml) and acetic anhydride (2.0 ml) was heated under argon for 2.5 h at 100° C. The solution was cooled to room temperature, water was added, and the product was extracted three times with ether. The combined ethereal phases were washed first with saturated sodium bicarbonate solution, then with sodium chloride solution and dried over anhydrous sodium sulfate. Evaporation of the solvent afforded an oil (483 mg) which was chromatographed over silica gel eluting with 30% ether/70% hexane, yielding (3E)-4-(5-acetoxy-3-methyl-1,3-pentadien-1-ylidene)- 3,5,5-trimethyl-2-cyclohexen-1-one (148 mg, 23%). The product gave a single spot on tlc (silica gel, 50% ether/50% hexane, $R_f$ 0.3); $^1$H NMR (360 MHz, CDCl$_3$): 6.31 (br s, H-2, 1H), 5.89 (t, J=1.2Hz, H- 2, 1H) 5.61 (br t,J=7.0 Hz, H-4', 1H). 4.68 (d, J=7.0 Hz, H-5', 2H), 2.38 (br s,H-6,2H_, 1.94 (d,J=1.2 Hz, C-3 methyl, 3H), 1.74 (br s, C-3' methyl, 3H), 1.17 (s, C-5 methyl, 3H), and 1.15 (s, C-5 methyl, 3H); IR (film)$_{max}$ 910,1730,1650 and 1590 cm$^{-1}$;GC/MS m/z 274(5), 232(7), 214(100) and 199(49); UV (hexane) 267 nm (24,400).

EXAMPLE 2

Alternative preparation of
(3E)-4-(5-acetoxy-3-methyl-1,3-pentadien-1-ylidene)3,5,5-trimethyl-2-cyclohexen-1-one (PBI-27)

To a solution of (3E)-4-(5-hydroxy-3-methyl- 1,3-pentadien-1-ylidene)-3,5,5-trimethyl-2-cyclohexen-1-one (1.2 g, 5.2 mmol) in acetic anydride (5.0 mL) and triethylamine (5.0 mL) cooled to 0° C., was added 4,4-dimethylaminopyridine (25 ng). After 15 min. water was added to the reaction mixture, and the product was extracted three times with ether. The combined ethereal extracts were washed with sodium chloride solution, and dried over anhydrous sodium sulfate. Evaporation of the solvent and chromatography over silica gel in the manner described in Example 1 above gave the desired product (680 mg, 48%).

EXAMPLE 3

Preparation of
(4E)-5-(2,6,6-trimethylcyclohex-1-enyl)-3-hydroxy-3-methylpentenoic acid (PBI-03)

The corresponding methyl ester of (4E)-5-(2,6,6-trimethylcyclohex-1-enyl)- 3-hydroxy-3-methyl- pentenoic acid (10 g, 36 mmol) in ethanol (30 mL) was treated with sodium hydroxice solution (3N, 250 mL) and the solution refluxed for 0.5 h. After cooling, the ethanol was removed at reduced pressure. The basic aqueous phase was extracted three times with ether to remove neutral components. The aqueous phase was then made acidic with hydrochloric acid and the product extracted three times with dichloromethane. The pooled organic extracts were washed with sodium chloride solution and then dried over anhydrous sodium sulfate. Evaporation of the solvent afforded 8.5 g of an oil. Treatment of an analytical sample with diazomethane afforded the starting ester. The acid was employed without further purification. $^1$H NMR (360 MHz, CDCl$_3$): 6.08 (d, J=16.1 Hz, H-5, 1H), 5.45 (d, J=16.1 Hz, H-4, 1H), 2.65 (s, H-2, 2H), 1.93 (m, H-3', 2H), 1.35–1.55 (m, H-4', H-5', 4H), 0.93, 0.92 (s, H-8, H- 9, 6H).

EXAMPLE 4

Preparation of PBI-26 (III)

A solution of (2E)-5-(4-oxo-1-hydroxy-2,2,6-trimethylcyclohexyl)- 3-methylpent-2-en-4-yn-1-ol (570 mg, 2.3 mmol) and potassium hydrogen sulfate (approx. 20 mg) in acetic acid (3.0 ml) and acetic anhydride (2.0 ml) was heated under argon for 2.5 h at 100° C. The solution was cooled to room temperature, water was added, and the product was extracted three times with ether. The combined ethereal phases were washed first with saturated sodium bicarbonate solution, then with sodium chloride solution and dried over anhydrous sodium sulfate. Evaporation of the solvent afforded and oil (483 mg) which was chromatographed over silica gel eluting with 50% ether/50% hexane yielding compound III (48 mg, 9%).

EXAMPLE 5

Z-5-(5-hydroxy-3-methyl-pent-3-en-1-ynyl)-3,5,5-trimethyl- 2-cyclohexen-1-one (1) (PBI-05)

A solution of Z-3-methylpent-2-en-4-yn-1-ol (Fluka, 7.9 g, 80 mmol) in dry THF (200 mL) under an argon atmosphere was cooled to about –60° C. in a dry ice-acetone bath. n-Butyllithium (Aldrich, 1.6M in hexane, 103 mL, 164 mmol) was added dropwise with stirring, followed after 0.5 h by a solution of oxoisophorone (Fluka, 6.1 g, 40 mmol) in dry THF (80 mL). A heavy precipitate was obtained at the end of the addition. The reaction mixture was stirred for 45 min. before it was poured into water and extracted three times with ether. The combined organic extracts were washed twice with saturated NaCl and dried over anhydrous Na2SO4. Evaporation of solvent gave a yellow oil (18 g) as the crude product. Purification of the product by flash column chromatography, with 50% ether +50% hexane followed by 100% ether as eluents, gave the alkylation product (6.9 g, 70% yield) as a yellow oil, ir: 3620 (sharp, medium, OH), 3420 (broad, medium, OH), 2220 (weak, acetylene), 1660 (strong, C=O) cm-1; 1H nmr d: 5.83 (tq, J=6.6, 1.5 Hz, 1H, =CH), 5.76 (q, J=1.3 Hz, 1H, =CH), 4.17 (d, J=6.6 Hz, 2H, CH2OH), 3.3 (1H, OH), 2.37 (m, 2H, CH2), 2.05 (d, J=1.3 Hz, 3H, vinyl CH3), 1.79 (m, 3H, vinyl CH3), 1.12 and 1.03 (2s, 6H, 2CH3); 13C nmr d: 198.76 (s, C=O), 160.89 (s, =C), 136.74 (d, =CH), 125.75 (d, =CH), 120.02 (=C), 92.80 and 85.19 (2s, 2 acetylenic C), 74.59 (s, C—OH), 65.74 and 60.93 (2t, 2CH2), 41.79 (s, C), 25.11, 22.81, 19.74 and 15.12 (4q, 4CH3); ms m/z: 248 (M+, approx. 0.05), 230 (7), 192 (18), and 174 (100).

EXAMPLE 6

9-Z-9-(5-hydroxy-3-methyl-pent-3-en-1-ynyl)-3,3,8,8,10-pentamethyl-1,5-dioxaspiro[5,5]undecan-9-ol (2)

A mixture of 2,2,6-trimethyl-1,4-cyclohexanedione (1.07 g, 6.9 mmol), 2,2-dimethyl-1,3-propanediol (0.95 g, 9.1 mmol), p-toluenesulfonic acid (59 mg), and benzene (15 mL) was heated to reflux under a Dean-Stark water separator for 2 h. The reaction mixture was allowed to cool to room temperature before it was neutralized with saturated NaHCO3, washed with H2O, and dried over anhydrous Na2SO4. Evaporation of solvent gave a colorless oil (1.76 g) as the crude product, which was distilled using the Kugelrohr apparatus (about 150° C., 0.5 mm Hg) to give pure ketal as a colorless oil (1.60 g, 96%), ir: 1710 (Strong, C=O) cm-1; 1H nmr d: 3.61 and 3.53 (2d, J=11.4 Hz, 2 axial H of CH2O), 3.48 and 3.41 (2dd, J=11.4, 1.6 Hz, 2 equatorial H of CH2O), 2.85 (m, 1H, CH), 2.47 (dd, J=14.2, 3.7 Hz, 1H, equatorial H of CH2), 2.38 (ddd, J=13.5, 5.3, 3.8 Hz, 1H, equatorial H of CH2), 1.58 (d, J=14.2 Hz, axial H of CH2), 1.56 (dd, J=13.5, 13.5 Hz, axial H of CH2), 1.16 (s, 3H, CH3), 0.97 (s, 6H, 2CH3), 0.91 (d, J=6.6 Hz, 3H, CHCH3), 0.85 (s, 3H, CH3); ms m/e: 240 (M+, 0.58), 141 (27), 155 (98), 83 (27), 69 (100). Ketal 1.31 g, 5.5 mmol) was reacted with Z-3-methylpent-2-en-4-yn-1-ol (0.65 g, 6.7 mmol) and n-butyllithium (1.6M in hexane, 8 mL, 12.8 mmol) in dry THF by the procedure described for the preparation of Z-5-(5-hydroxy-3-methyl-pent-3-en-1-ynyl)-3,5,5-trimethyl- 2-cyclohexen-1-one. The crude product (yellow oil, 2.6 g) obtained was purified by flash column chromatography using 75% ether+25% hexane as eluent and subsequent distillation using the Kugel-rohr apparatus (about 250° C., 0.06 mm Hg) to give ketal (2) (1.40 g, 77%), ir: 3610 (strong, sharp, OH), 3440 (broad, medium, OH), 1110 and 1090 (strong, C—O) cm-1; 1H nmr d: 5.50 (ddq, J=6.7, 6.7, 1.5 Hz, 1H, =CH), 4.29 (broad s, 2H, CH2OH), 3.55 (d, J=11.3 Hz, 2H, 2 axial H of CH2O), 3.38 and 3.36 (2dd, J=11.3, 1.9 Hz, 2 equatorial H of CH2O), 2.51 (dd. J=14.3, 3.2 Hz, 1H, equatorial H of CH2), 2.18 (m, 1H, CH), 1.98 (ddd, J=13.8, 3.4, 3.4 Hz, 1H, equatorial H of CH2), 1.84 (m, 3H, vinyl CH3), 1.53–1.61 (m, 2H, 2 axial H of CH2), 1.11, 1.09, 1.06, 1.05, 1.04 and 0.83 (15H, 5CH3); ms (trimethylsilyl ether) m/z: 408 (M+ of trimethylsilyl ether), 155 (100); high resolution ms (trimethylsilyl ether): calc. for C23H4004Si 408.2696, found 408.2718.

EXAMPLE 7

Z-4-(5-acetoxy-3-methyl-pent-4-en-1-ynyl)-3,5,5-trimethylcyclohex- 3-en-1-one (3)

A mixture of (Z)-4-hydroxy-4-(5-hydroxy-3-methylpent-3-en- 1-ynyl)-3,5,5-trimethylcyclohexanone 795 mg, 3.1 mmol), glacial acetic acid (5 mL), acetic anhydride (5 mL), and KHSO4 (440 mg, 3.2 mmol) was heated to 70° C. under argon for 5 h. Then the mixture was cooled to room temperature and slowly added to a chilled (ice bath) and stirred mixture of hexane and saturated NaHCO3. More saturated NaHCO3 was added until the pH of the aqueous phase was about 6–7. The organic and aqueous layers were then separated, and the aqueous layer was extracted with hexane. The combined hexane layers were washed with saturated NaHCO3, H2O, and dried over anhydrous Na2SO4. Removal of solvent gave a yellow oil (737 mg) which on purification by flash column chromatography using 75% ether+25% hexane as solvent gave compound (3) (600 mg, 70%) as a yellow oil, ir: 1730 (strong, broad) cm-1; 1H nmr d: 5.77 (ddq, J=7.0, 7.0, 1.5 Hz, 1H, =CH), 4.76 (dd, J=7.0, 1.0 Hz, 2H CH2O), 2.90 (broad s, 2H, CH2), 2.39 (s, 2H, CH2), 2.03 (s, 3H, CH3COO), 1.94 and 1.93 (2m, 6H, 2 vinyl CH3), 1.16 (s, 6H, 2CH3); ms m/z: 274 (M+, 30), 214 (100).

EXAMPLE 8

Z-4-(5-acetoxy-3-methyl-pent-3-en-1-ynyl)
-3,4-epoxy- 3,5,5-trimethylcyclohexan-1-ol (4)

To a solution of Z-4-(5-acetoxy-3-methyl-pent-3-en-1ynyl)- 3,5,5-trimethylcyclohex-3-en-1-ol (42 mg, 0.15 mmol) in toluene (6 mL) was added t-butyl hydroperoxide (3M solution in 2,2,4-trimethylpentane, 0.07 mL, 0.21 mmol) and vanadyl acetylacetonate (3 mg, 0.01 mmol). The reaction mixture, which was reddish orange in color, was stirred under argon at room temperature for 20 min. and then was heated to 70° C. for 30 min. The color of the mixture changed to yellow. After cooling to room temperature, saturated NaHSO3 was added with stirring until there was no peroxide as indicated by peroxide test tapes. The organic and aqueous layers were separated. The aqueous layer was extracted three times with ether. The combined organic layers were washed with H2O, saturated NaHCO3, H2O and dried over anhydrous Na2SO4. Evaporation of solvent gave yellow oil (46 mg) which was purified using the Chromatotron™ sold by Harrison Scientific and with 75% ether+ 25% hexane as solvent to give compound (4) as a colorless oil (17 mg, 38%), ir: 3620 (weak, sharp, OH), 3500 (weak, broad, OH), 1740 (strong, sharp, C=O) cm-1; 1H nmr d: 5.80 (ddq, J=6.9, 6.9, 1.6 Hz, 1H, =CH), 4.71 (dd, 6.9, 1.0 Hz, 2H, CH2O), 3.83 (m, 1H, CHOH), 2.19 (ddd, J=14.7, 6.8, 1.5 Hz, 1H, CH2), 2.03 (s, 3H, CH3COO), 1.89 (m, 3H, vinyl CH3), 1.81 (dd, J=14.7, 8.9 Hz, 1H, CH2), 1.47 (s, CH3), 1.37 (ddd, J=12.7, 4.0, 1.5 Hz, 1H, CH2), 1.18 (s, 6H, 2CH3); ms (isobutane CI) m/z: 293 (M+1), 331 (M+39); (NH4Cl CI): 310 (M+18), 275 (M−17), 233 (M−59).

Alternatively, molybdenum hexacarbonyl could be used in the above procedure instead of vanadyl acetylacetonate but longer reaction time was required.

EXAMPLE 9

Z-4-(5-hydroxy-3-methyl-pent-3-en-1ynyl)
-3,4-epoxy- 3,5,5-trimethylcyclohexan-1-ol (5)

A mixture of Z-4-(5-acetoxy-3-methyl-pent-3-en- 1ynyl)-3,4-epoxy-3,5,5-trimethylcyclohexan-1-ol (36 mg, 0.12 mmol), K2CO3 (26 mg, 0.18 mmol), methanol (1 mL) and H2O (1 mL) was stirred at room temperature for 1 h. It was then concentrated by evaporation and the residue was diluted with H2O and extracted with CHCl3. The organic extract was dried over anhydrous Na2SO4. Evaporation of solvent gave compound (5) as a colorless oil (21 mg, 69%), ir: 3620 (sharp, medium, OH) and 3450 (broad, weak, OH) cm-1; 1H nmr d: 5.87 (ddq, J=6.7, 6.7, 1.4 Hz, 1H, =CH), 4.27 (dd, J=6.7, 1.0 Hz, 2H, CH2O), 3.82 (m, 1H, CHOH), 2.18 (ddd, J=14.8, 6.8, 1.4 Hz, 1H, CH2), 1.86 (m, 3H, vinyl CH3), 1.79 (dd, J=14.8, 9.0 Hz, 1H, CH2), 1.46 (s, CH3), 1.36 (ddd, J=12.7, 4.1, 1.5 Hz, 1H, CH2), 1.16 and 1.17 (2s, 6H, 2CH3); 13C nmr d: 136.63 (d, =CH), 119.95 (s, =C), 90.95 and 83.99 (2s, 2 acetylenic C), 65.08 and 64.52 (2s, C—O—C), 63.29 (d, CHOH), 61.15, 41.84 and 38.16 (3t, 3 CH2), 34.83 (s, C), 27.03, 25.60, 22.98 and 22.92 (4q, 4CH3); ms (NH4Cl CI) m/z: 268 (M+18), 251 (M+1), 233 (M−17).

EXAMPLE 10

Trans (−)-(4R,6R)-4-t-Butyldimethylsilyloxy-2,2,6-trimethylcyclohexanone

A mixture of trans (4R,6R)-4-hydroxy-2,2,6-trimethylcyclohexanone (115 mg, 0.73 mmol), t-butyldimethylsilyl chloride (Aldrich, 202 mg, 1.27 mmol), imidazole (100 mg, 1.47 mmol) and dry DMF (3 mL) was stirred at room temperature under an argon atmosphere for 1.5 h. Then water was added and the mixture was extracted three times with ether. The ether extract was washed with saturated NaCl and dried over anhydrous Na2SO4. Evaporation of solvent gave a colorless oil (325 g) which was distilled using the Kugel-rohr apparatus. After some forerun which was discarded, the desired silyl ether was collected as a colorless oil at 150°–180° C., 9–10 mm Hg (156 mg, 80%). The product solidified on storage at −10° C. to form colorless crystals, mp 29.5°–31.5° C.; [a]D −65.1° C. (c 1.06, CH3OH); ir: 1710 cm-1; 1H nmr d: 0.06 and 0.07 (2s, 6H, CH3SiCH3), 0.89 (s, 9H, 3CH3), 0.98 (s, 3H, CH3), 0.98 (d, J=6.4 Hz, 3H, CHCH3), 1.32 (s, 3H, CH3), 1.57 (ddd, J=13.4, 13.2, 2.7 Hz, H-5ax), 1.65 (dd, J=14.2, 3.4 Hz, 1H, H-3ax), 1.88 (ddd, J=14.2, 3.3, 3.2 Hz, 1H, H-3eq), 1.99 (dddd, J=13.0, 5.3, 3.3, 3.2 Hz, 1H, H-5eq), 3.16 (ddq, J=13.2, 5.3, 6.4 Hz, 1H, H-6ax), 4.08 (q, J=3.2 Hz, 1H, H-4eq); eims m/z: 255 (M+−15, 1), 213 (60), 171 (78), 121 (43), 75 (100); hrms: calc. for C15H30O2Si 270.2015, found 270.2015.

EXAMPLE 11

(−)-1(Z)-(1S, 4R, 6R)- and (−)-1(Z)-(1R, 4R, 6R)-1-( 5-Acetoxy-3-methylpent-3-en-1-ynyl)-2,2,6-trimethylcyclohexan- 1,4-diol (6 and 7)

A solution of Z-3-methylpent-2-en-4-yn-1-ol (Fluka, 1.60 g, 16.7 mmol) in dry THF (20 mL) under an argon atmosphere was cooled to about −60° C. in a dry ice-acetone bath. n-Butyllithium (Aldrich, 1.6M in hexane, 19 mL, 30.4 mmol) was added dropwise with stirring. After all the n-butyllithium had been added the reaction mixture, which was orange in color, was allowed to warm up to −5° C. over 30 min. Then it was again cooled to −60° C. and a solution of trans (−)-(4R,6R)-4-t-Butyldimethylsilyloxy- 2,2,6-trimethylcyclohexanone (2.7 g, 10 mmol) in dry THF (20 mL) was added dropwise. After the addition had been completed the reaction mixture was allowed to warm up to 0° C. over 90 min. before it was poured into water and extracted three times with ether. The combined organic extracts were washed twice with saturated NaCl and dried over anhydrous Na2SO4. Evaporation of solvent gave a yellow oil (4.5 g) as the crude product. Purification of the product by flash column chromatography (75% ether+25% hexane as eluent) followed by distillation (Kugel-rohr, 180°–200° C., 0.03 mmHg) gave a mixture of compounds as a yellow oil (2.82 g, 76% yield), gc retention times (DB1701™ column, 70°–240° C. at 10° C. min-1) 20.05 min. and 19.77 min., ratio of peak areas about 8:1, respectively.

The mixture (2.82 g, 7.6 mmol) was dissolved in pyridine (15 mL). A mixture of acetic anhydride (2.35 g, 23.0 mmol) and pyridine (5 mL) was added, followed by 4-dimethylaminopyridine (Aldrich, 32 mg, 0.26 mmol). The reaction mixture was stirred at room temperature for 1 h before it was worked up by pouring into water and extracting three times with hexane. The combined organic extract was washed with saturated NaCl and dried over anhydrous Na2SO4. Removal of solvent gave a mixture of acetates as a pale yellow oil (3.72g) which was desilated to give two hydroxyacetates by the procedure below without purification. GC analysis of the crude acetate mixture (DB1701™ column, 70°–240° C. at 10° C. min-1) showed two components in the ratio of 8:1 (retention times 20.26 min and 20.12 min, respectively).

The crude acetates obtained in the above procedure was stirred with glacial acetic acid (30 mL) and H2O (10 mL), and the mixture was heated to 70° C. under argon for 20 h. After cooling to room temperature, the reaction mixture was diluted with water and extracted three times with CHCl3. The organic extract was washed with H2O, saturated NaHCO3 and dried over anhydrous Na2SO4. Evaporation of solvent gave a yellow oil (2.98 g) as the crude product. Separation by flash column chromatography (75% ether+ 25% hexane) followed by preparative tlc (same eluent) gave the cis diol (1.26 g, 56% overall yield) and trans diol (0.15 g, 7% overall yield). (−)-1(Z)-(1S, 4R,6R) -1-(5-acetoxy-3-methylpent3-en- 1-ynyl)-2,2,6-trimethylcyclohexan-1,4-diol, colorless oil; gc (DB5 column, 70°–240° C. at 10° C. min-1) retention time 18.37 min.; tlc (90% ether+10% hexane) Rf about 0.30; [a]D −18.4° C. (c 1.02, CH3OH); ir: 3610, 3400, 1735 cm-1; 1Hnmr d: 1.05 (d, J=6.6 Hz, CHCH3), 1.08 and 1.22 (2s, 6H, 2CH3), 1.55–1.75 (m, 4H, 2CH2), 1.89 (m, 3H, vinyl CH3), 2.03 (s, 3H, CH3COO), 2.34 (m, 1H, CHCH3), 4.02 (m, 1H, CHOH), 4.71 (dd, J=7.0, 1.0 Hz, 2H, CH2O), 5.77 (ddq, J=7.0, 7.0, 1.5 Hz, 1H, =C); 13C nmr d: 16.05, 20.88, 23.08, 23.28 and 27.39 (5 CH3), 38.77 (C2), 31.92, 40.12 and 44.47 (CH2 and CH), 62.80 and 67.55 (CH2O and CHOH), 79.01 (COH), 84.89 and 95.33 (2 acetylenic C), 123.52 (=C), 130.03 (=CH), 170.83 (C=O); eims m/z: 234 (M+−60, 6), 178 (28), 148 (100).

(−)-1(Z)-(1R, 4R, 6R)-1-(5-acetoxy-3-methylpent- 3-en-1-ynyl)-2,2,6-trimethylcyclohexan-1,4-diol, colorless oil; gc (DB5 column, 70°–240° C. at 10° C. min-1) retention time 18.50 min.; tlc (90% ether+10% hexane) Rf about 0.35; [a]D −28.3° C. (c 0.92, CH3OH); ir: 3630, 3500, 1735 cm-1; 1H nmr d: 1.05 (s, 3H, CH3), 1.06 (d, J=5.2 Hz, 3H, CHCH3), 1.27, (s, 3H, CH3), 1.43 (ddd, J=14.6, 2.5, 2.5 Hz, 1H, H-3eq), 1.52 (dddd, J=14.3, 3.9, 2.5, 2.5 Hz, 1H, H-5eq), 1.68 (ddd, J=14.3, 12.6, 3.3 Hz, 1H, H-5ax), 1.76 (dd, J=14.6, 3.5 Hz, 1H, H-3ax), 1.89 (m, 3H, vinyl CH3), 2.03 (s, 3H, CH3COO), 2.33 (m, 1H, CHCH3), 4.07 (m, 1H, CHOH), 4.72 (dd, J=7.0, 1.0 Hz, 2H, CH2O), 5.76 (ddq, J=7.0, 7.0, 1.5 Hz, 1H, =CH); 13C nmr d: 16.81, 20.91, 23.21, 26.78 and 27.13 (5 CH3), 38.17 (C2), 30.77, 35.75 and 40.29 (2 CH2 and CH), 62.79 and 67.04 (CH2O and CHOH), 76.53 (COH), 83.52 and 97.37 (2 acetylenic C), 123.62 (=C), 129.99 (=CH), 170.86 (C=O); eims m/z: 234 (M+−60, 3), 178 (10), 148 (100).

EXAMPLE 12

(−)-4(Z)-(4R, 5R)-4-Hydroxy-4-(5-hydroxy-3-methylpent-3-en-1-ynyl)- 3,3,5-trimethylcyclohexanone (8)

(Z)-(1R, 4R, 6R)-1-(5-Acetoxy-3-methylpent-3-en-1-ynyl)-2,2,6-trimethylcyclohexan-1,4-diol (140 mg, 0.47 mmol) was oxidized with pyridinium dichromate (850 mg, 2.26 mmol) in CH2Cl2 (15 mL) to give a keto-acetate as a colorless oil (90 mg, 70%), [a]D −26.0° C. (c 0.78, CH3OH); ir: 3630, 1730 cm-1; 1H nmr d: 1.03 (s, 3H, CH3), 1.17 (d, J=6.3 Hz, 3H, CHCH3), 1.19 (s, 3H, CH3), 1.89 (m, 3H, vinyl CH3), 1.95 (dd, J=13.8, 2.3 Hz, 1H, H-2eq), 2.04 (s, 3H, CH3COO), 2.16 (ddd, J=13.2, 3.8, 2.3 Hz, 1H, H-6eq), 2.31 (ddq, J=12.4, 6.3, 3.8 Hz, 1H, CHCH3), 2.39 (dd, J=13.2, 12.4 Hz, 1H, H-6ax), 2.73 (broad d, J=13.8 Hz, 1H, H-2ax), 4.73 (dd, J=7.0, 0.9 Hz, 2H, CH2O), 5.81 (ddq, J=7.0, 7.0, 1.5 Hz, 1H, =CH); ms m/e: 232 (M+−60, 24), 176 (47), 148 (41), 120 (23), 106 (100); hrms (M+−60 peak): calc. for C15H20O2 232.1463, found 232.1485.

The keto-acetate (90 mg, 0.3 mmol) was hydrolyzed by treating with 5M KOH (5 drops) and methanol (10 mL) to give −)-4(Z)-(4R,5R)-4-Hydroxy-4-(5-hydroxy-3-methylpent- 3-en-1-ynyl)-3,3,5-trimethylcyclo-hexanone as a colorless oil (69 mg, 92%) {(the racemate crystallized on storage at −10° C. to give colorless crystals, mp 72.5°–79.5° C.}, ir: 3630, 1710 cm-1; 1H nmr d: 1.03 (s, 3H, CH3), 1.17 (d, J=6.4 Hz, 3H, CHCH3), 1.19 (s, 3H, CH3), 1.88 (m, 3H, vinyl CH3), 1.96 (dd, J=13.8, 2.3 Hz, 1H, H-2eq), 2.16 (ddd, J=13.3, 3.4, 2.3 Hz, 1H, H-6eq), 2.32 (m, 1H, CHCH3), 2.39 (ddd, J=13.3, 12.8, 0.8 Hz, 1H, H-6ax), 2.72 (ddd, J=13.8, 0.8, 0.8 Hz, 1H, H-2ax), 4.29 (dd, J=6.8, 1.0 Hz, 2H, CH2OH), 5.88 (ddq, J=6.8, 6.8, 1.5 Hz, 1H, =CH); 13C nmr d: 16.76, 23.13, 24.98 and 25.41 (4q, 4CH3), 37.64 (d, CH), 43.06 (s, C3), 44.25, 49.48 and 61.27 (3t, 3CH2), 75.25 (s, COH), 84.47 and 94.85 (2s, 2 acetylenic C), 120.26 (s, =C), 136.08 (d, =CH), 210.86 (s, C=O); ms m/e: 250 (M+, very weak), 232 (5), 179 (23), 165 (66), 106 (100); hrms: calc. for C15H22O3 250.1569, found 250.1570.

EXAMPLE 13

(−)-(9Z)-(9S,10R)-9-(5-Hydroxy-3-methylpent-3-en-1-ynyl)- 3,3,8,8,10-pentamethyl-1,5-dioxaspiro[5,5]undecan-9-ol (9)

A mixture of (−)-4(Z)-(4S,5R)-4-hydroxy-4-(5-hydroxy-3-methylpent- 3-en-1-ynyl)-3,3,5-trimethylcyclohexanone (620 mg, 2.49 mmol), 2,2-dimethyl-1,3-propanediol (Aldrich, 460 mg, 4.4 mmol), pyridinium p-tosylate (Aldrich, 19 mg, 0.07 mmol) and benzene (18 mL) was heated to reflux under a Dean-Stark separator for 4 hrs. The reaction mixture was then allowed to cool to room temperature, washed with saturated Na2CO3, saturated NaCl and water. After drying over anhydrous Na2SO4 and evaporation of solvent a yellow oil was obtained as the crude product (1 g). Purification by flash column chromatography (75% ether+25% hexane) gave the desired ketal as a pale yellow oil (750 mg, 90%), [a]D −29.4° C. (c 1.02, CH3OH); ir: 3610, 3440, 1110 and 1090 cm-1; 1H nmr d: 0.83, 1.04, 1.05, 1.06, 1.09, and 1.11 (15H, 5 CH3), 1.53–1.61 (m, 2H, 2 axial H at C7 and C11), 1.84 (m, 3H, vinyl CH3), 1.98 (ddd, J=13.8, 3.4, 3.4 Hz, 1H, H-11eq), 2.18 (m, 1H, CH), 2.51 (dd. J=14.3, 3.2 Hz, 1H, H-7eq), 3.36 and 3.38 (2dd, J=11.3, 1.9 Hz, 2H, 2 equatorial H at C2 and C4), 3.55 (d, J=11.3 Hz, 2H, 2 axial H at C2 and C4), 4.29 (broad s, 2H, CH2OH), 5.50 (ddq, J=6.7, 6.7, 1.5 Hz, 1H, =CH); eims (trimethylsilyl ether) m/z: 408 (M+ of trimethylsilyl ether), 155 (100); hrms (trimethylsilyl ether): calc. for C23H40O4Si 408.2696, found 408.2718.

EXAMPLE 14

(−)-9(1E,3Z)-(9R,10R)-9-(5-Hydroxy-3-methyl-1, 3-pentadienyl)- 3,3,8,8,10-pentamethyl-1,5-dioxaspiro[5,5]-undecan-9-ol (10)

A solution of (−)-(9Z)-(9S,10R)-9-(5-hydroxy-3-methylpent- 3-en-1-ynyl)-3,3,8,8,10-pentamethyl-1,5-dioxaspiro[ 5,5]undecan-9-ol (730 mg, 2.2 mmol) in dry THF (50 mL) was stirred under an argon atmosphere and cooled with an ice-water bath. Sodium is (2-methoxyethoxy)aluminium hydride (RedalR, Aldrich, 3.4M in toluene, 1.3 mL, 4.4 mmol) was added dropwise. Some frothing occurred as the RedalR was added. The reaction mixture was stirred at 0° C. until the frothing subsided. Then another portion of RedalR (0.7 mL, 2.2 mmol) was added. After 1.5 h of stirring at 0°

C. followed by 1 h at room temperature, the reaction was worked up by pouring into H2O and extracting three times with ether. The combined organic extracts were washed with saturated NaCl and dried over anhydrous Na2SO4. Evaporation of solvent gave a colorless oil (about 1 g) as the crude product which was usually hydrolyzed by the procedure described in Example 15. A small amount of the crude product was purified on the Chromatotron™ (75% ether+ 25% hexane) to give the desired ketal as a colorless oil, [a]D −64.4° C. (c 1.02, CH3OH); ir: 3600, 1600, 1100, 975, 910 cm-1; 1H nmr d: 0.76, 0.78, 0.85, 1.05 and 1.12 (15H, 5 CH3), 1.34–1.42 (m, 2H, 2 axial H at C7 and C11), 1.85 (d, J=0.9 Hz, 3H, vinyl CH3), 1.97 (ddd, J=14.0, 3.5, 3.5 Hz, 1H, H-11eq), 2.16 (m, 1H, CH), 2.29 (dd, J=14.6, 3.2 Hz, 1H, H-7eq), 3.40 (m, 2H, 2 equatorial H at C2 and C4), 3.57 and 3.58 (2d, J=11.2, 11.4 Hz, respectively, 2H, 2 axial H at C2 and C4), 4.31 (d, J=6.9 Hz, 2H, CH2OH), 5.54 (t, J=7 Hz, 1H, =CH), 5.94 (d, J=15.6 Hz, 1H, =CH), 6.68 (d, J=15.6 Hz, 1H, =CH).

EXAMPLE 15

(−)-4(1E,3Z)-(4R,5R)-4-Hydroxy-4-(5-hydroxy-3-methyl-1,3-pentadienyl)-3,3,5-trimethylcyclohexanone (11)

The crude ketal obtained in the procedure described in Example 14 was hydrolyzed by stirring with 1M HCl (5 drops) and acetone (50 mL) at room temperature for 2 h. After concentration of the acetone solution, saturated NaHCO3 was added and the mixture was extracted with ether. The organic layer was dried with anhydrous Na2SO4 and concentrated to give a yellow oil as the crude product. Flash column chromatography using 90% ether+10% hexane as eluent gave the desired compound as a colorless oil (338 mg, 60%) {The racemate crystallized on standing at room temperature and could be recrystallized from ether-hexane to give colorless crystals, mp 128° C.}, [a]D −41.6° C. (c 0.98, CH3OH); ir: 3610 , 3450, 1710, 1610, 975 cm-1; 1H nmr d: 0.84 (d, J=6.3 Hz, CHCH3), 0.89 and 1.01 (2s, 6H, CH3), 1.88 (d, J=0.8 Hz, 3H, vinyl CH3), 2.1–2.3 (m, 4H, H-2eq, CH2 at C6 and CHCH3), 2.46 (d, J=15.8 Hz, 1H, H-2ax), 4.31 (d, J=7.0 Hz, 2H, CH2OH), 5.59 (t, J=7.0 Hz, 1H, =CH), 6.07 (d, J=15.6 Hz, 1H, =CH), 6.81 (dd, J=15.6, 0.4 Hz, 1H, =CH); 13C nmr d: 15.91, 20.78, 22.78 and 25.18 (4q, 4 CH3), 37.39 (d, CH), 41.64 (s, C3), 47.08, 52.88 and 58.34 (3t, 3CH2), 78.12 (s, COH), 128.36, 128.64 and 128.96 (3d, 3 =CH), 134.40 (s, =C), 209.55 (s, C=O); eims (trimethylsilyl ether) m/e: 324 (M+ of trimethylsilyl ether, 3), 73 (100); hrms (trimethylsilyl ether): calc. for C18H32O3Si 324.2121, found 324.2109.

EXAMPLE 16

(−)-4(1E,3Z)-(4R,5R)-4-Hydroxy-4-(5-oxo-3-methyl-1,3-pentadienyl)-3,3,5-trimethylcyclohexanone (12)

To a solution of ketoalcohol as described in Example 15 (300 mg, 1.2 mmol) in acetone (30 mL) was added manganese oxide (2.08 g, 24 mmol). The mixture was stirred at room temperature under a drying tube for 1 h before the manganese oxide was removed by filtration. The solid residue was rinsed with acetone and the rinsing was combined with the filtrate. Evaporation of acetone gave the crude aldehyde which was usually oxidized to ester without purification as described in Example 17.

A small amount of aldehyde was purified by preparative tlc (90% ether+10% hexane) followed by recrystallization from ether-hexane to give colorless crystals, mp 106.0°–108.5° C.; [a]D −64.5 (c 0.38, CH3OH); ir: 3550, 1715 and 1665 cm-1; 1H nmr d: 0.89 (d, J=6.4 Hz, 3H, CHCH3), 0.93 and 1.04 (2s, 6H, 2CH3), 2.11 (d, J=1.1 Hz, 3H, vinyl CH3), 2.15–2.42 (m, CH2 at C6 and CHCH3), 2.17 (dd, J=14.9, 2.5 Hz, H-2eq), 2.48 (d, J=14.9 Hz, 1H, H-2ax), 5.90 (d, J=7.7 Hz, 1H, =CH), 6.49 and 7.50 (2d, J=15.4 Hz, 2H, 2 =CH), 10.21 (d, J=8.0 Hz, 1H, HC=O); high resolution ms: calc. for C15H22O3 250.1569, found 250.1575.

EXAMPLE 17

(−)-(4R, 5R)-Methyl 2',3'-dihydroabscisate (13)

Crude aldehyde as described in Example 16 (about 1.2 mmol) obtained from the procedure described in Example 16 was dissolved in methanol (30 mL). Manganese oxide (1.79 g, 20 mmol), sodium cyanide (87 mg, 1.7 mmol) and glacial acetic acid (0.10 g, 1.6 mmol) were added. The mixture was stirred at room temperature for 5 h before it was filtered through CeliteR. The manganese oxide residue and Celite were rinsed with methanol and the rinsing was combined with the filtrate. The combined rinsing and filtrate was then concentrated, and the residue was partitioned between ether and H2O. The ether layer was separated, dried over anhydrous Na2SO4, and concentrated to give a yellow oil (283 mg) as crude product. Purification on the Chromatotron™ (4 mm silica gel plate, 90% ether+10% hexane) gave (−)-(4R, 5R)-methyl dihydroabscisate as colorless crystals (199 mg, 70% overall yield). Part of the product was recrystallized from ether-hexane to give colorless needles, mp 117.0°–119.5° C.; [a]D −62.7° C. (c 0.90, CH3OH); hplc {Chiracel OD column (18, 19), 10% isopropanol+90% hexane at 1.0 mL min-1} retention time 10.7 min.; ir: 3600, 1710 cm-1; 1H nmr d: 0.88 (d, J=6.3 Hz, 3H, CHCH3), 0.92 and 1.04 (2s, 6H, 2 CH3), 2.03 (d, J=1.2 Hz, 3H, vinyl CH3), 2.15 (dd, J=16.0, 15.0 Hz, H-6ax), 2.15 (dd, J=15.0, 2.5 Hz, H-2eq), 2.30–2.40 (m, 2H, CHCH3 and H-6eq), 2.46 (d, J=14.9 Hz, 1H, H-2ax), 3.69 (s, 3H, OCH3), 5.74 (s, 1H, =CH), 6.46 (d, J=16.0 Hz, 1H, =CH), 7.91 (dd, J=16.0, 0.6 Hz, 1H, =CH); 13C nmr d: 16.00, 21.28, 22.87 and 25.25 (4q, 4 CH3), 37.40 (d, CH), 41.71 (s, C3), 47.10 (t, CH2), 51.10 (q, CH3O), 52.92 (t, CH2), 78.14 (s, COH), 117.62, 129.41 and 135.15 (3d, 3 =CH), 149.41 (s, =C), 166.51 (s, OC=O), 209.12 (s, C=O); eims m/e: 280 (M+, 2), 192 (35), 164 (23), 123 (100); hrms: calc. for C16H24O4 280.1675, found 280.1664. Anal. calc. for C16H24O4: C 68.53%, H 8.63%; found: C 68.67%, H 8.74%.

EXAMPLE 18

(−)-(4R, 5R)-2',3'-dihydroabscisic acid (14)

A mixture of (−)-(4R, 5R)-methyl 2',3'-dihydroabscisate (166 mg, 0.6 mmol), 2M KOH (6 mL) and methanol (3 mL) was stirred at room temperature for 4 h. Most of the methanol was then evaporated. The residue was diluted with H2O, extracted with ether, and the ether extract was discarded. The aqueous layer was acidified with 1M HCl and then extracted with CHCl3. The CHCl3 layer gave, after drying over anhydrous Na2SO4 and evaporation of solvent, (−)-(4R, 5R)-dihydroabscisic acid as white crystals (118 mg, 78%). Part of the product was recrystallized from CHCl3-hexane to give white crystals, mp 177°–184° C. {lit. mp of racemate 193.5° C.}; [a]D −65.2° C. (c 0.66, CH3OH); ir:

2800–3200, 1715, 1690 cm-1; 1H nmr d: 0.89 (d, J=6.4 Hz, CHCH3), 0.93 and 1.06 (2s, 6H, 2 CH3), 2.08 (s, 3H, vinyl CH3), 2.14–2.43 (m, 4H, CHCH3, CH2 at C6 and H-2eq), 2.47 (d, J=14.9 Hz, 1H, H-2ax), 5.77 (broad s, 1H, =CH), 6.50 and 7.88 (2d, J=16.0 Hz, 2H, 2 =CH); eims (trimethylsilyl ether) m/z: 338 (M+, 2), 192 (30), 73 (100); hrms (trimethylsilyl ether): calc. for C18H30O4Si 338.1913, found 338.1921. Anal. calc. for C15H22O4: C 67.63%, H 8.33%; found C 67.21%, H 8.30%.

EXAMPLE 19

(−)-(9Z)-(9R, 10R)-9-(5-Hydroxy-3-methylpent-3-en-1-ynyl)-3,3,8,8,10-pentamethyl-1,5-dioxaspiro[5,5]undecan-9-ol (15)

(−)-4(Z)-(4R,5R)-4-Hydroxy-4-(5-hydroxy-3-methylpent- 3-en-1-ynyl )-3,3,5-trimethylcyclohexanone (130 mg, 0.52 mmol) was treated with a mixture of 2,2-dimethyl-1,3-propanediol (160 mg, 1.53 mmol), pyridinium p-tosylate (9 mg, 0.04 mmol) and benzene (4 mL) according to the procedure described in Example 13. The desired ketal was obtained as a pale yellow oil (149 mg, 89%), [a]D −27.8° C. (c 1.2, CH3OH); ir: 3610, 3440, 1110 and 1090 cm-1; 1H nmr d: 0.84 (s), 1.04 (s), 1.08 (s), 1.09 (d, J=6.8 Hz), and 1.16 (s) (15H, 5 CH3), 1.52 (d, J=14.1 Hz, 1H, H-7ax), 1.58 (dd, J=13.4, 13.2 Hz, 1H, H-11ax), 1.83 (ddd, J=13.4, 3.7, 2.9 Hz, 1H, H-11eq), 1.87 (m, J=1Hz, 3H, vinyl CH3), 2.11 (dd. J=14.1, 2.8 Hz, 1H, H-7eq), 2.13–2.22 (m, 1H, CHCH3), 3.35–3.41 (m, 2 equatorial H at C2 and C4), 3.58 and 3.54 (2d, J=11.9 and 12.6 Hz, respectively, 2H, 2 axial H at C2 and C4), 4.29 (d, J=6.2 Hz, 2H, CH2OH), 5.84 (ddq, J=6.7, 6.7, 1.5 Hz, 1H, =CH); hrms (M+−18 peak): calc. for C20H30O3 318.2195, found 318.2188.

EXAMPLE 20

(−)-9(1E, 3Z)-(9S,10R)-9-(5-Hydroxy-3-methyl-1,3pentadienyl)-3,3,8,8,10-pentamethyl-1,5-dioxaspiro[5,5]-undecan-9-ol (16)

(−)-(9Z)-(9R, 10R)-9-(5-Hydroxy-3-methylpent-3-en-1-ynyl)- 3,3,8,8,10-pentamethyl-1,5-dioxaspiro[5,5]-undecan-9-ol (149 mg, 0.44 mmol) was reduced with sodium bis(2-methoxyethoxy)aluminium hydride (RedalR, Aldrich, 3.4M in toluene, 0.8 mL, 2.48 mmol) by the procedure described in Example 14. The crude product obtained was usually hydrolyzed to give the ketodiol without purification. A small amount of the crude product was purified on the Chromatotron™ (75% ether+25% hexane) to give the desired ketal as a colorless oil, ir: 3600, 1600, 1100, 975, 910 cm-1; 1H nmr d: 0.76 (d, J=6.9 Hz), 0.83 (s), 0.84 (s), 1.02 (s) and 1.06 (s) (15H, 5 CH3), 1.57 (d, J=14.1 Hz, 1H, H-7ax), 1.59 (dd, J=13.0, 12.7 Hz, 1H, H-11ax), 1.84 (ddd, J=12.7, 3.6, 2.7 Hz, 1H, H-11eq), 1.85 (d, J=0.9 Hz, 3H, vinyl CH3), 2.08 (dd, J=14.1, 2.7 Hz, 1H, H-7eq), 2.16 (ddq, J=13.0, 3.6, 6.8 Hz, 1H, CHCH3), 3.30–3.50 (m, 2H, 2 equatorial H at C2 and C4), 3.56 and 3.60 (2d, J=11.7, 11.5 Hz, respectively, 2H, 2 axial H at C2 and C4), 4.30 (d, J=7.0 Hz, 2H, CH2OH), 5.54 (dd, J=7.0, 6.8 Hz, 1H, =CH), 5.70 (d, J=15.8 Hz, 1H, =CH), 6.60 (d, J=15.8 Hz, 1H, =CH).

EXAMPLE 21

(−)-4(1E, 3Z)-(4S, 5R)-4-Hydroxy-4-(5-hydroxy-3-methyl-1,3-pentadienyl)-3,3,5-trimethylcyclohexanone (17)

The crude ketal obtained in the procedure described in Example 20 was hydrolyzed by stirring with 1M HCl (4 drops ) and acetone (5 mL) at room temperature for 1 h. Working up in the usual manner followed by purification on the Chromatotron™ (4 mm silica gel plate, 90% ether+10% hexane) gave the desired compound as a colorless oil (33 mg, 30% overall), [a]D −18.3° C. (c 1.1, CH3OH); ir: 3620, 1700 cm-1; 1H nmr d: 0.86 (d, J=6.5 Hz, CHCH3), 0.88 and 0.93 (2s, 6H, CH3), 1.86 (d, J=1.1 Hz, 3H, vinyl CH3), 1.90 (dd, J=13.6, 2.2 Hz, 1H, H-2eq), 2.18 (ddd, J=13.5, 4.3, 2.2 Hz, 1H, H-6eq), 2.23–2.33 (m, 1H, CHCH3), 2.41 (t, J=13.5 Hz, 1H, H-6ax), 2.82 (d, J=13.6 Hz, H-2ax), 4.31 (m, 2H, CH2OH), 5.59 (dd, J=7.0, 6.3 Hz, 1H, =CH), 5.73 (d, J=15.7 Hz, 1H, =CH), 6.69 (d, J=15.7 Hz, 1H, =CH); 13C nmr d: 16.03, 20.72, 24.51 and 24.59 (4q, 4 CH3), 36.83 (d, CH), 42.85 (s, C3), 45.11, 51.46 and 58.34 (3t, 3 CH2), 77.78 (s, COH), 126.70, 128.28 and 134.02 (3d, 3 =CH), 134.51 (s, =C), 211.45 (s, C=O); hrms: calc. for C15H24O3 252.1725, found 252.1708.

EXAMPLE 22

(−)-4(1E, 3Z)-(4S, 5R)-4-Hydroxy-4-(5-oxo-3-methyl-1,3pentadienyl)-3,3,5-trimethylcyclohexanone (18)

The ketodiol 17 (30 mg, 0.11 mmol) was oxidized with manganese oxide (420 mg, 4.8 mmol) to give the corresponding aldehyde by the procedure described in Example 17. The crude aldehyde was usually oxidized to ester as described in Example 23 without purification.

A small amount of the aldehyde 18 was purified by preparative tlc (90% ether+10% hexane) to give a colorless oil, [a]D −39.5 (c 0.77, CH3OH); ir: 3610, 3450, 1700 and 1665 cm-1; 1H nmr d: 0.89 (d, J=6.4 Hz, 3H, CHCH3), 0.96 (s, 6H, 2CH3), 1.93 (dd, J=13.6, 2.2 Hz, H-2eq), 2.08 (d, J=1.1 Hz, 3H, vinyl CH3), 2.20–2.46 (m, CH2 at C6 and CHCH3), 2.84 (d, J=13.6 Hz, 1H, H-2ax), 5.90 (d, J=7.8 Hz, 1H, =CH), 6.16 (dd, J=15.47, 0.4 Hz, 1H, =CH), 7.40 (d, J=15.7 Hz, 1H, =CH), 10.20 (d, J=7.8 Hz, 1H, HC=O).

EXAMPLE 23

(−)-(4S, 5R)-2′,3′-Methyl dihydroabscisate (19)

Crude (−)-4(1E, 3Z)-(4S, 5R)-4-Hydroxy-4-(5-oxo-3-methyl-1,3-pentadienyl)-3,3,5-trimethylcyclohexanone (about 0.11 mmol) obtained from the procedure described in Example 22 was reacted with a mixture of methanol (5 mL), manganese oxide (310 mg, 3.56 mmol), sodium cyanide (35 mg, 0.71 mmol) and glacial acetic acid (35 mg, 0.58 mmol). The desired product (−)-(4S, 5R)-methyl dihydroabscisate was obtained as colorless crystals (21 mg, 70% overall yield). Part of the product was recrystallized from ether-hexane at 0° C. to give colorless plates, mp 105°–108° C.; [a]D −40.6° C. (c 1.03, CH3OH); ir: 1700 cm-1; 1H nmr d: 0.87 (d, J=6.5 Hz, 3H, CHCH3), 0.94 and 0.96 (2s, 6H, 2 CH3), 1.91 (dd, J=13.6, 2.2 Hz, 1H, H-2eq), 2.01 (d, J=1.2 Hz, 3H, vinyl CH3), 2.20 (ddd, J=13.6, 4.2, 2.2 Hz, H-6eq), 2.33 (m, 1H, CHCH3), 2.44 (dd, J=13.6, 13.0 Hz, 1H, H-6ax), 2.86 (d, J=13.6 Hz, 1H, H-2ax), 3.70 (s, 3H, OCH3), 5.72 (s, 1H, =CH), 6.09 (d, J=15.9 Hz, 1H, =CH), 7.81 (d, J=15.9 Hz, 1H, =CH); eims m/z: 280 (M+, 4), 192 (43), 164 (24), 123 (100); hrms: calc. for C16H24O4 280.1675, found 280.1649.

EXAMPLE 24

(−)-(4S, 5R)-2',3'-dihydroabscisic acid (20)

(−)-(4S, 5R)-Methyl dihydroabscisate (15 mg, 0.05 mmol) was hydrolysed with 2M KOH (3 mL) and methanol (3 mL) to give (−)-(4S,5R)-dihydro-abscisic acid as a colorless oil (13 mg, 90%), [a]D −34.5° C. (c 0.89, CH3OH); ir: 2800–3500, 1680 cm-1; 1H nmr d: 0.88 (d, J=6.4 Hz, CHCH3), 0.95 and 0.96 (2s, 6H, 2 CH3), 1.91 (dd, J=13.6, 2.1 Hz, 1H, H-2eq), 2.04 (d, J=1.2 Hz, 3H, vinyl CH3), 2.21 (ddd, J=13.4, 4.1, 2.1 Hz, H-6eq), 2.35 (m, 1H, CHCH3), 2.44 (dd, J=13.4, 12.7 Hz, 1H, H-6ax), 2.86 (d, J=13.6 Hz, 1H, H-2ax), 5.75 (s, 1H, =CH), 6.14 and 7.79 (2d, J=16.1 Hz, 2H, 2 =CH); 13C nmr: 16.05, 21.48, 24.58 and 24.63 (4 CH3), 43.00 (C3), 36.67, 45.03 and 51.42 (CH and 2 CH2), 78.00 (COH), 151.77, 140.60, 127.72 and 116.99 (4 =C), 170.63 (COOH), 211.26 (C=O); eims m/z: 266 (M+, about 2), 248 (5), 192 (29), 164 (67), 123 (100); hrms: calc. for C15H22O4 266.1518, found 266.1519.

EXAMPLE 25

(+)-(4R, 6S)-4-Hydroxy-2,2,6-trimethylcyclohexanone (21)

A mixture of (−)-(4R,6R)-4-hydroxy-2,2,6-trimethylcyclohexanone (300 mg, 0.19 mmol), 5M NaOH (1 mL) and ethanol (10 mL) was heated to 85° C. for 24 hrs under an argon atmosphere. Then most of the ethanol was removed by evaporation. The residue was dissolved in ether, and the solution was washed with water. After drying over anhydrous Na2SO4 and evaporation of the solvent, a pale yellow oil (255 mg) was obtained. Purification by flash chromatography (75% ether+25% hexane) gave unreacted trans ketol (46 mg), [a]D −102.3° C. (c 0.92, CH3OH), followed by the desired cis ketol as a colorless oil (195 mg, 73% based on starting material consumed). The product solidified on storage at −10° C. and was recrystallized from ether-hexane to give colorless needles, mp 48.0°–50.0 ° C. {lit. (13) mp 52°–53° C.}; [a]D +95.0° C. (c 0.88, CH3OH) {lit. (13) [a]D +107.4° C. (c 0.8, CH3OH) }; 1H nmr d: 0.96 (d, J=6.5 Hz, 3H, CHCH3), 1.00 and 1.14 (2s, 3H each, 2 CH3), 1.35 (ddd, J=12.4, 12.4, 11.3 Hz, 1H, H-5ax), 1.53 (dd, J=12.2, 11.5 Hz, 1H, H-3ax), 2.00 (ddd, J=12.2, 4.2, 3.5 Hz, H-3eq), 2.22 (m, 1H, H-5eq), 2.67 (m. 1H, H-6ax), 4.25 (tt, J=11.3, 4.3 Hz, 1H, H-4ax); eims m/z: 156 (M+, 10), 138 (8), 83 (66), 74 (50), 69 (60), 57 (100).

EXAMPLE 26

(+)-(4R, 6S)-4-t-Butyldimethylsilyloxy-2,2,6-trimethylcyclohexanone (22)

The cis ketol obtained in Example 25 (66 mg, 0.42 mmol) was treated with a mixture of t-butyldimethylsilyl chloride (130 mg, 0.86 mmol), imidazole (73 mg, 1.07 mmol) and dry DMF (2 mL). After working up and purification by distillation (kugel-rohr, 150°–180° C., 8–10 mm Hg), the desired silyl ether was obtained as a colorless oil (111 mg, 99%); [a]D +58.0° C. (c 0.98, CH3OH); ir: 1710 cm-1; 1H nmr d: 0.07 (s, 6H, CH3SiCH3), 0.87 (s, 9H, 3 CH3), 0.98 (d, J=6.5 Hz, 3H, CHCH3), 1.03 and 1.17 (2s, 3H each, 2 CH3), 1.43 (ddd, J=13.6, 12.8, 11.0 Hz, 1H, H-5ax), 1.58 (dd, J=13.1, 11.1 Hz, 1H, H-3ax), 1.89 (ddd, J=13.1, 4.3, 3.5 Hz, 1H, H-3eq), 2.11 (m, 1H, H-5eq), 2.68 (ddq, J=12.8, 6.5, 6.5 Hz, 1H, H-6ax), 4.24 (tt, J=11.0, 4.4 Hz, 1H, H-4ax); cims (isobutane) m/e: 271 (M++1); hrms: calc. for C15H30O2Si 270.2015, found 270.2004.

EXAMPLE 27

(+)-1(Z)-(1R, 4R,6S)-4-t-Butyldimethylsilyloxy-1-(5-hydroxy-3-methylpent-3-en-1-ynyl)-2,2,6-trimethylcyclohexanol (23)

The ketosilyl ether from Example 26 (5.7 g, 21 mmol) was treated with Z-3-methylpent-2-en-4-yn-1-ol (3.0 g, 32 mmol) and n-butyllithium (1.6M in hexane, 40 mL, 63 mmol). The desired product was obtained as a colorless oil (4.9 g, 64%) which solidified on storage at 0° C. to give colorless crystals, gc (DB1701 column, 70°–240° C. at 10° C. min-1) retention time 19.11 min.; mp 89°–94° C.; [a]D +19.1° C. (c 0.82, CH3OH); ir: 3620 cm-1; 1H nmr d: 0.03 (s, 6H, CH3SiCH3), 0.86 (s, 9H, 3 CH3), 1.01 (s, 3H, CH3), 1.05 (d, J=6.5 Hz, 3H, CHCH3), 1.11 (s, 3H, CH3), 1.40, 1.55 and 1.73 (3m, 2 CH2), 1.89 (d, J=1.0 Hz, 3H, vinyl CH3), 1.92–2.00 (m, 1H, CHCH3), 3.83 (tt, J=10.8, 5.2 Hz, 1H, CHOSi), 4.32 (m, 2H, CH2OH), 5.86 (ddd, J=6.7, 6.7, 1.5 Hz, 1H, =CH); cims (isobutane) m/e: 367 (M++1), 349.

EXAMPLE 28

(+)-1(Z)-(1R, 4R,6S)-1-(5-Acetoxy-3-methylpent-3-en-1-ynyl)-2,2,6-trimethylcyclohexan-1,4-diol (24)

The dihydroxysilyl ether described in Example 27 (2.5 g, 6.9 mmol) was reacted with acetic anhydride (2.5 g, 18.6 mmol), pyridine (25 mL) and 4-dimethylaminopyridine (32 mg, 0.2 mmol) by the procedure previously described. A small amount of the crude acetate obtained was purified on the Chromatotron™ (1 mm silica gel plate, 50% ether+50% hexane) to give a colorless oil, gc (DB1701 column, 70°–240° C. at 10° C. min-1) retention time 19.37 min.; [a]D +17.6° C. (c 1.07, CH3OH); ir: 3610, 3500, 1735 cm-1; 1H nmr d: 0.03 (s, 6H, CH3SiCH3), 0.86 (s, 9H, 3 CH3), 1.01 (s, 3H, CH3), 1.05 (d, J=6.5 Hz, 3H, CHCH3), 1.11 (s, 3H, CH3), 1.37, 1.56 and 1.73 (3 m, 2 CH2), 1.90 (d, J=1.3 Hz, 3H, vinyl CH3), 1.96 (m, 1H, CHCH3), 2.03 (s, 3H, CH3C=O), 3.84 (tt, J=11.0, 5.0 Hz, 1H, CHOSi), 4.74 (dd, J=7.1, 0.9 Hz, CH2O), 5.79 (dd, J=7.1, 7.1, 1.5 Hz, 1H, =CH); eims m/e: 348 (M+−60); cims (isobutane) m/e: 409 (M++1), 349.

The crude acetate was desilated by heating (80° C.) with glacial acetic acid (30 mL) and water (10 mL) to give, after work up and purification, the desired product as a colorless oil (1.46 g, 73% overall yield), [a]D +23.8° C. (c 0.4, CH3OH); ir: 3610, 1735 cm-1; 1H nmr d: 1.03 (s, 3H, CH3), 1.06 (d, J=6.5 Hz, 3H, CHCH3), 1.12 (s, 3H, CH3), 1.37 and 1.57 (2 m, H-3ax and CH2 at C5), 1.70 (ddd, J=12.7, 4.6, 2.3 Hz, 1H, H-3eq), 1.91 (d, J=1.3 Hz, vinyl CH3), 2.00 (m, 1H, CHCH3), 2.04 (s, 3H, CH3C=O), 3.84 (m, 1H, CHOH), 4.77 (d, J=7.3 Hz, CH2O), 5.70 (ddd, J=7.1, 7.1, 1.5 Hz, 1H, =CH); 13C nmr: 16.43, 20.73, 20.95, 23.17 and 26.96 (5 CH3), 39.92 (C2), 35.86, 41.76 and 46.38 (CH and 2 CH2), 62.89 and 66.10 (CHOH and CH2O), 78.31 (COH), 85.43 and 95.17 (2 acetylenic C), 123.68 (=C), 129.96 (=CH), 171.04 (C=O); eims m/e: 294 (M+, very weak), 234 (10), 148 (100).

EXAMPLE 29

(+)-4(Z)-(4R, 5S)-4-Hydroxy-4-(5-hydroxy-3-methylpent-3-en-1-ynyl)-3,3,5-trimethylcyclohexanone (25)

The dihydroxy acetate obtained in Example 28 (1.44 g, 4.9 mmol) was oxidized with pyridinium dichromate (6.07 g, 16.1 mmol) in CH2Cl2 (30 mL). A keto-acetate was obtained as colorless needles (0.94 g, 70%), mp 118.0°–120.0° C.; [a]D +20.5° C. (c 0.58, CH3OH); ir, 1H and 13C nmr identical with those of the (–)-enantiomer.

The keto-acetate (0.94 g, 3.2 mmol) was hydrolysed by stirring with 5M NaOH (1 mL) and methanol (25 mL) at room temperature for 1 h. After working up and purification, the desired product (+)-4(Z)-(4R,5S)-4-hydroxy- 4-(5-hydroxy-3-methylpent-3-en-1-ynyl)-3,3,5trimethylcyclohexanone was obtained as colorless crystals (0.80 g, 100%), mp 96.5°–98.0° C.; [a]D +22.3° C. (c 0.53, CH3OH); ir, 1H and 13C nmr identical with those of the (–)-(4S, 5R) enantiomer.

EXAMPLE 30

(+)-(9Z)-(9R, 10S)-9-(5-Hydroxy-3-methylpent-3-en-1-ynyl)-3,3,8,8,10-pentamethyl-1,5-dioxaspiro [5,5] undecan-9-ol (26)

(+)-4(Z)-(4R,5S )-4-Hydroxy-4-(5-hydroxy-3-methyl-pent-3-en- 1-ynyl)-3,3,5-trimethylcyclohexanone was treated with 2,2-dimethylpropane-1,3-diol in benzene with a catalytic amount of p-toluenesulfonic acid to afford the ketal, [a]D +27.1° C. (c 0.90, CH3OH).

EXAMPLE 31

(+)-9(1E, 3Z)-(9S,10S)-9-(5-Hydroxy-3-methyl-1,3-pentadienyl)-3,3,8,8,10-pentamethyl-1,5-dioxaspiro[5,5]-undecan-9-ol and (+)-4(1E,3Z)-(4S,5S)-4-Hydroxy-4-(5-hydroxy-3-methyl-1,3-pentadienyl)-3,3,5-trimethylcyclohexanone (27)

Reduction of (+)-(9Z)-(9R,10S)-9-(5-Hydroxy-3-methyl-pent- 3-en-1-ynyl)-3,3,8,8,10-pentamethyl-1,5-dioxaspiro [5,5]undecan-9-ol with RedalR as described in Example 14 afforded the dienoic system and the product was hydrolyzed with 1M HCl and acetone as previously described to give the desired product ketone, [a]D +42.6° C. (c 1.03, CH3OH).

EXAMPLE 32

(+)-4-(1E,3Z)-(4S,5S)-4-Hydroxy-4-(5-oxo-3-methyl-1,3-pentadienyl)-3,3,5-trimethylcyclohexanone (29)

The aldehyde was prepared by the oxidation of (+)-4(1E, 3Z)-(4S,5S)-4-Hydroxy-4-(5-hydroxy-3-methyl-1,3-pentadienyl)- 3,3,5-trimethylcyclohexanone with manganese oxide and was further oxidized to (+)-(4S, 5S)-methyl 2',3'-dihydroabscisate without purification

EXAMPLE 33

(+)-(4S, 5S)-2',3'-Methyl dihydroabscisate (30)

The aldehyde obtained in Example 32 was reacted with MnO2, NaCN, methanol and glacial acetic acid according to the procedure previously described to give (+)-(4S, 5S)-methyl dihydroabscisate as colorless needles, mp 117.5°–118.5° C.; [a]D +65.7° C. (c 0.9, CH3OH); hplc (Chiracel OD column, 10% isopropanol+90% hexane at 1.0 mL min-1) retention time 8.7 min.

EXAMPLE 34

(+)-(4S, 5S)-2',3'-Dihydroabscisic acid (31)

(+)-(4S, 5S)-methyl dihydroabscisate was hydrolyzed with 2M KOH and methanol to give (+)-(4S, 5S)-dihydroabscisic acid as colorless crystals, 173°–180° C.; [a]D +63.5° C. (c 1.17, CH3OH).

EXAMPLE 35

(–)-(10R)-3,3,8,8,10-Pentamethyl-1,5-dioxaspiro [5,5]-undecan-9-one (32)

A mixture of (–)-(6R)-2,2,6-trimethyl-1,4-cyclohexandione (924 mg, 6.0 mmol), 2,2-dimethyl-1,3-propandiol (791 mg, 7.6 mmol), pyridinium p-tosylate (34 mg, 0.13 mmol), and benzene (15 mL) was heated to reflux under a Dean-Stark water separator for 4 h. The reaction mixture was allowed to cool to room temperature before it was washed with H2O, and dried over anhydrous Na2SO4. Evaporation of solvent gave a pale yellow oil (1.43 g) as the crude product, which was distilled using the Kugel-rohr apparatus (80°–100° C., 0.03 mm Hg) to give pure ketal as a colorless oil (1.31 g, 91%), [a]D –87.7° C. (c 1.10, CH3OH); ir: 1710 cm-1; 1H nmr d: 0.85 (s, 3H, CH3), 0.91 (d, J=6.6 Hz, 3H, CHCH3), 0.97 (s, 6H, 2CH3), 1.16 (s, 3H, CH3), 1.56 (dd, J=13.5, 13.5 Hz, H-11ax), 1.58 (d, J=14.2 Hz, H-7ax), 2.38 (ddd, J=13.5, 5.3, 3.8 Hz, 1H, H-11eq), 2.47 (dd, J=14.2, 3.8 Hz, 1H, H-7eq), 2.85 (m, 1H, CHCH3), 3.41 and 3.48 (2dd, J=11.4, 1.6 Hz, 2H, 2 equatorial H at C2 and C4), 3.53 and 3.61 (2d, J=11.4 Hz, 2H, 2 axial H at C2 and C4); ms m/e: 240 (M+, 0.58), 141 (27), 155 (98), 83 (27), 69 (100).

EXAMPLE 36

(–)-(9Z)-(9S,10R)-9-(5-Hydroxy-3-methylpent-3-en-1-ynyl)-3,3,8,8,10-pentamethyl-1,5-dioxaspiro[5,5]undecan-9-ol (33)

(–)-(10R)-3,3,8,8,10-Pentamethyl-1,5-dioxaspiro[ 5,5] undecan-9-one (1.31 g, 5.5 mmol) was reacted with Z-3-methylpent-2-en-4-yn-1-ol (0.65 g, 6.7 mmol) and n-butyl-lithium (1.6M in hexane, 8 mL, 12.8 mmol) in dry THF. The crude product obtained (yellow oil, 2.6 g) was purified by flash column chromatography (75% ether+25% hexane) followed by distillation using the Kugel-rohr apparatus (about 250° C., 0.06 mm Hg) to give the product as a colorless oil (1.40 g, 77%), [a]D –30.0° C. (c 1.05, CH3OH); ir and 1H nmr identical to those reported above for its antipode.

EXAMPLE 37

(±)-Z-4-hydroxy-4-(5-oxo-3-methylpent-3-en-1-ynyl)-3,3,5-trimethylcyclohexanone (34) (PBI-18)

To pyridinium dichromate (1.14 g, 3.75 mmol) in dry DMF (6 mL), at 5°–10° C. was slowly added (±)-Z-4-hydroxy-4-( 5-hydroxy-3-methylpent-3-en-1-ynyl)-3,3,5-trimethylcyclohexanone (750 mg, 3.0 mol) in DMF (5 mL). The reaction was maintained at 5° C. for 2.5 h, and then water was added and the product extracted three times with ether. The combined ethereal phases were washed with water, then with saturated NaCl solution, then dried over Na2SO4 and the solvent evaporated to afford 570 mg of crude product which was crystallized from ether to give 410 mg (54%) aldehyde that gave m.p. 126°–127° C.; ir (CHCl3) 3600 strong, 2200 weak, 1710, 1670, 1600, 1100, 1060, and 1020 cm-1; 1H nmr –‖: 1.01 and 1.22 (s, gem CH3, 6H), 1.16 (d, J=5.8 Hz, CHCH3, 3H), 2.16 (d, J=1.5 Hz, =CCH3, 3H), 2.1–2.4 (m, 4H), 2.61 (d, J=14.4 Hz, H-2ax, 1H), 6.22 (dq, J=8.1, 1.5 Hz, =CH, 1H), and 10.03 (d, J=8.1 Hz, CHO, 1H ).

EXAMPLE 38

(±)-E-4-hydroxy-4-(5-oxo-3-methylpent-3-en-1-ynyl)-3,3,5-trimethylcyclohexanone (35) (PBI-19)

A mixture of (±)-E-4-hydroxy-4-(5-hydroxy-3-methylpent- 3-en-1-ynyl)-3,3,5-trimethylcyclohexanone (2.0 g, 8.0 mol), manganese dioxide (14 g, 160 mmol), and acetone (50 mL) were combined and strred for 1.5 h. The mixture was filtered, the solvent removed by evaporation, and the residue chromatographed over silica eluting with 75% ether and 25% hexane to afford 1.17 g (±)-E-4-hydroxy- 4-(5-oxo-3-methylpent-3-en-1-ynyl)-3,3,5-trimethylcyclohexanone (58%), as an oil, that gave ir: 3600 (strong), 220 (weak), 1710, 1660, 900 cm-1; gc/eims: 248 (M+, 15%) 233 (9), 219 (19), 205 (16), 192 (42), 163 (95) and 121 (100); 1H nmr –‖: 0.99 and 1.20 (s, gem CH3, 6H), 1.14 (d, J=5.9 Hz, HCCH3, 3H), 2.11 (dd, J=14.3, 2.3 Hz, H-2 eq, 1H), 2.18 (m, H-6eq, 1H), 2.3 (m, 2H), 2.32 (d, J=1.5 Hz, =CCH3, 3H), 2.60 (d, J=14.3 Hz, H-2ax, 1H), 6.22 (dq, J=7.7, 1.5 Hz, =CH, 1H), and 10.03 (d, J=7.7 Hz, CHO, 1H).

EXAMPLE 39

Methyl 2-Z 5-(4-oxo-2,2,6-trimethylcyclohexan-1-ol)-3-methylpenten- 4-ynoate (36) (PBI-41)

Z-4-hydroxy-4-(5-oxo-3-methylpent-3-en-1-ynyl)- 3,3,5-trimethylcyclohexanone (34) (350 mg, 1.4 mmol) was treated with manganese dioxide (1.9 g, 22 mmol), sodium cyanide (165 mg, 3.4 mmol), acetic acid (80 uL, 1.4 mL) in methanol (15 mL). After 2 h the mixture was filtered, the solid washed with ether. The combined organic phases were washed twice with water, then saturated NaCl solution, dried over anhydrous Na2SO4, and the solvent removed at reduced pressure. The product 36 was obtained pure by chromatography over silica (Chromatotron, elution with 50% ether 50% hexane, as an oil that gave: ir (CHCl3) 3600 (weak), 1710 (strong) cm-1; 1H nmr –‖: 0.99 and 1.23 (s, gem CH3, 6H), 1.16 (d, J=6.3 Hz, HCCH3, 3H), 2.06 (d, J=1.5 Hz, =CCH3, 3H), 2.1–2.6 (m, 4H), 2.86 (d, J=14.3 Hz, H-3ax, 1H), 3.67 (s, OCH3, 3H), and 6.02 (q, J=1.5 Hz, =CH, 1H); gc/eims m/z 278 (m+, 4), 247 (6), 219 (46) and 137 (100).

EXAMPLE 40

2-Z 5-(4-oxo-2,2,6-trimethylcyclohexan-1-ol)-3-methyl-pen-ten- 4-ynoic acid (37) (PBI-40)

The ester 36 was saponified as for compound 30 to afford the enynoic acid 37 in 83% yield. The product gave ir (CHCl3) 3600 (weak), 3300 (br,strong) and 1690 (strong) cm-1; 1H nmr d: 0.99 and 1.21 (s, gem CH3, 6H), 1.14 (d, J=6.2 Hz, HCCH3, 3H), 2.25–2.35 (m, 4H), 2.47 (d, J=14.1 Hz, H-3eq, 1H), 2.82 (d, J=14.1 Hz, H-3ax, 1H), and 6.03 (q, J=1.4 Hz, =CH, 1H).

EXAMPLE 41

Preparation of 4(Z)-(4R)-4-Hydroxy-4-(5-hydroxy-3-methylpent-3-en-1-ynyl)-3,5,5-trimethylcyclohex-2-enone (PBI-53)

This compound was prepared using the procedure described by Lamb and Abrams in 1990 Can. J. Chem. 68:1151–1162, hereby incorporated by reference, with the exception that oxo-isophorone was used as a starting material. Spectroscopic data is as follows: $^1$H NMR: δ6.01 (d, 1H-3', J=1Hz), 5.83 (d, 1H-2, J=0.5 Hz), 3.67 (s, 3H-1), 3.34 (br s, 1H, OH), 2.58 (d, 1H-5', J=16 Hz), 2.38 (d, 1H-5', J=16 Hz), 2.12 (d, 3H-7', J=1 Hz), 2.00 (d, 3H-6, J=1 Hz), 1.21 (s, 3H-8'/9'), 1.09 (s, 3H-8'/9').

EXAMPLE 42

Preparation of 4(Z)-(4R)-4-Hydroxy-4-(5-carboxy-3-methylbut-3-en-1-ynyl )-3, 5, 5-trimethylcyclohex-2-enone (BPI-54)

This compound was prepared using the procedure described by Lamb and Abrams in 1990 Can. J. Chem. 68:1157–1162, hereby incorporated by reference, with the exception that oxo-isophorone was used as a starting material. Spectroscopic data is as follows: $^1$H NMR: δ6.03 (d, 1H-3', J=1Hz), 5.86 (s, 1H-2), 2.63 (d, 1H-5', J=16 Hz), 2.38 (d, 1H-5', J=16 Hz), 2.10 (d, 3H-7', J=1 Hz), 2.04 (d, 3H-6, J=1 Hz), 1.21 (s, 3H-8'/9'), 1.09 (s, 3H-8'/9').

EXAMPLE 43

Preparation of compounds PBI-209–211.

These compounds were prepared using the methods described by Lamb and Abrams in 1990 Can. J. Chem. 68:1151–1162, hereby incorporated by reference. The starting materials used were chosen from (8S*, 10S*)-8-Cyano-3,3,8,10-tetramethyl-1,5-dioxaspiro-[5, 5]-undecan-9-one or from (2S*, 6S*)-2-Cyano-2,6-Dimethyl--4,4-(2',2'-dimethylpropanedioxy)-cyc lohexanone which has the following spectroscopic data:

$^1$H NMR: δ3.738 (d, 1H, J=11.7 Hz, OCH$_2$), 3.574 (dd, 1H, J=11.7, 1.7 Hz, OCH$_2$), 3.513 (d, 1H, J=11.4 Hz, OCH$_2$), 3.416 (dd, 1H, J=11.4, 1.7 Hz, OCH$_2$), 3.266 (m, 1H, H-2), 3.082 (dd, 1H, J=14.3, 4.2 Hz, H-5e), 2.436 (ddd, 1H, J=13.4, 5.3, 4.4 Hz, H-3e), 1.552 (d, 1H, J=13.4 Hz, H-3a), 1.520 (d, 1H, J=14.3 Hz, H-5a), 1.420 (s, 3H, C-9, Me), 1.068 (s, 3H, Me), 1.090 (s, 3H, J=6.5 Hz, C-7, Me), 0.881 (s, 3H, Me). HRMS: calcd for C$_{14}$H$_{21}$O$_3$N (M$^+$) 251.1550, found 251.1521.

Spectroscopic data for the resulting compounds is as follows:

(1'S*, 2'S*)-(2E, 4Z)-Methyl-5-(6'-cyano-2',6'-dimethyl-1'-hydroxy-cyclohexan-4'-onyl)-3-methylpent-2,4-dienate (PBI-209).

$^1$H NMR: δ8.064 (s, 1H, J=15.8 Hz, H-4), 6.095 (d, 1H, J=15.8 Hz, H-5), 5.802 (s, 1H, H-2), 3.708 (s, 3H, OMe), 2.711 (dd, 1H, J=15.9, 2.3 Hz, H-5'e), 2.675-2.510 (overlap 2H, H-2', H-3'e), 2.475 (d, 1H, J=15.9 Hz, H-5'a), 2.418 (br s, 1H, OH), 2.226 (dd, 1H, J=16.0, 13.5 Hz, H-3'a), 2.019 (d, 3H, J=1.0 Hz, C-6, Me), 1.382 (s, 3H, C-9', Me), 0.977 (d, 3H, J=6.5 Hz, C-7', Me). HRMS: calcd for $C_{16}H_{21}O_4N$ ($M^+$) 291.1498, found 291.1471.

(1'S*, 2'S*)-(2E, 4Z)-5-(6'-cyano-2',6'-dimethy-1'-hydroxy-cyclohexan- 4'-onyl )-3-methylpent-2,4-dienoic acid (PBI-210).

$^1$H NMR: δ7.818 (d, 1H, J=15.9 Hz, H-4), 6.288 (d, 1H, J=15.9 Hz, H-5), 5.718 (s, 1H, H-2), 2.123 (d, 1H, J=11.3 Hz, H-5'), 2.053 (d, 3H, J=1.1 Hz, C-6, Me), 1.990–1.910 (overlap 2H, H-2', H-3'), 1.813 (dd, 1H, J=11.3, 3.0 Hz, H5'), 1.718 (t, 1H, J=14.2 Hz, H-3'), 1.062 (br s, 1H, OH), 1.047 (s, 3H, C-9, Me), 0.903 (d, 3H, J=6.4 Hz, C-7', Me).

(1'S*, 2'S*)-(2E, 4Z)-5-(6'-cyano-2',6'-dimethy-1'-hydroxy-cyclohexan- 4'-onyl )-3-methylpent-2,4-dien-1-al (PBI-211).

$^1$H NMR: δ10.050 (d, 1H, J=7.7 Hz, CHO), 6.811 (d, 1H, J=15.5 Hz, H-4), 6.221 (d, 1H, J=15.5 Hz, H-5), 6.077 (d, 1H, J=7.7 Hz, H-2), 2.748 (dd, 1H, J=16.0, 2.3 Hz, H-5'), 2.650–2.100 (overlap 4H, H-2', H-3', H-5'), 2.286 (d, 3H, J=1.0 Hz, C-6, Me), 1.568 (s, 1H, OH), 1.373 (s, 3H, C-9', Me), 0.978 (d, 3H, J=6.5 Hz, C-7', Me).

EXAMPLE 44

Preparation of compounds PBI-250–253, PBI-258–260.

These compounds were prepared using the method described by Lamb and Abrams in 1990 Can. J. Chem. 68:1151–1162, hereby incorporated by reference. The starting material used was the following: 2,6-Dimethy--4,4-ethylenedioxy-cyclohexa-2,5-dienone IR $n_{max}$ cm$^{-1}$: 1715 (C=O), 1630 (C=C); $^1$H NMR: δ6.39 (s, 2H, H-3, H-4), 4.18 (s, 4H, OCH2CH2O), 1.86 (s, 6H, Me). $^{13}$C NMR: δ186.4, 138.3 (2C), 135.5 (2C), 98.8, 65.3 (2C), 15.4 (2C). HRMS: calcd for C10H12O3 ($M^+$) 180.0786, found 180.0786.

Spectroscopic data for the resulting compounds is as follows:

(2E, 4Z)-5-(2',6'-dimethy-1'-hydroxy-cyclohexa-2',5'-dien- 4'-onyl)-3-methylpent-2,4-dien-1-ol (PBI-250).

$^1$H NMR: δ6.882 (d, 1H, J=15.6 Hz, H-4), 5.997 (s, 2H, H-3', H-5'), 5.607 (t, 1H, J=6.9 Hz, H-2), 5.309 (d, 1H, J=15.6 Hz, H-5), 4.310 (d, 2H, J=6.9 Hz, OCH$_2$), 2.053 (S, 1H, OH), 2.018 (s, 1H, OH), 1.946 (s, 6H, C-7', C-8', Me), 1.798 (s, 3H, C-6, Me).

(2E, 4Z)-5-(2',6'-dimethy-1'-hydroxy-cyclohexa-2',5'-dien- 4'-onyl)-3-methylpent-2,4-dien-1-al (PBI-251).

$^1$H NMR: δ9.973 (d, 1H, J=8.3 Hz, CHO), 7.421 (d, 1H, J=15.5 Hz, H-4), 6.016 (s, 2H, H-3', H-5'), 5.821 (d, 1H, J=8.3 Hz, H-2), 5.723 (d, 1H, J=15.5 Hz, H-5), 2.703 (s, 1H, OH), 2.172 (s, 6H, C-7', C-8', Me), 1.986 (d, 3H, J=1.0 Hz, C-6, Me).

(2E, 4Z)-Methyl-5-(2',6'-dimethy-1'-hydroxy-cyclohexa-2',5'-dien-4'-onyl)-3-methylpent-2,4-dienate (PBI-252).

$^1$H NMR: δ7.984 (d, 1H, J=15.9 Hz, H-4), 5.996 (s, 2H, H- 3', H-5'), 5.708 (s, 1H, H-2), 5.619 (d, 1H, J=15.9 Hz, H-5), 3.664 (s, 3H, OCH$_3$), 2.004 (br s, 1H, OH), 1.955 (s, 6H, C-7', C-8', Me), 1.929 (d, 3H, J=0.7 Hz, C-6, Me).

(2E, 4Z)-5-(2',6'-dimethy-1'-hydroxy-cyclohexa-2',5'-dien- 4'-onyl)-3-methylpent-2,4-dienoic acid (PBI-253).

$^1$H NMR: δ7.957 (d, 1H, J=15.5 Hz, H-4), 6.031(s, 2H, H-3', H-5'), 5.763 (d, 1H, J=15.5 Hz, H-5), 5.741 (s, 1H, H-2), 1.991 (s, 6H, C-7', C-8', Me) 1.965 (d, 3H, J=0.94 Hz, C-6, Me). HRMS: calcd for $C_{14}H_{14}O_3$ ($M^+$-$H_2O$) 230.0925, found 230.0943.

(2E)-5-(2',6'-dimethy-1'-hydroxy-cyclohexa-2',5'-dien-4'-onyl)- 3-methylpent-2-en-4-yn-1-ol (PBI-258).

$^1$H NMR: δ6.016 (s, 2H, H-3', H-5'), 5.945 (tm, 1H, J=6.6 Hz, H-2), 4.259 (d, 2H, J=6.6 Hz, OCH$_2$), 2.733 (s, 1H, OH), 2.204 (s, 6H, C-7', C-8', Me), 1.864 (d, 3H, J=1.1 Hz, C-6, Me). HRMS: calcd for $C_{14}H_{16}O_3$ ($M^+$) 232.1099, found 232.1093.

(2E)-5-(2',6'-dimethy-1'-hydroxy-cyclohexa-2',5'-dien-4'-onyl)- 3-methylpent-2-en-4-yn-1-al (PBI-259).

$^1$H NMR: δ9.861 (d, 1H, J=8.1 Hz, CHO), 6.187 (dm, 1H, J=8.1 Hz, H-2), 6.012 (s, 2H, H-3', H-5'), 4.187 (br s, 1H, OH), 2.205 (s, 6H, C-7', C-8', Me), 2.093 (d, 3H, J=1.4 Hz, C-6, Me).

(2E)-Methyl-5-(2',6'-dimethy-1'-hydroxy-cyclohexa-2',5-dien-4'-onyl)- 3-methylpent-2-en-4-ynate (PBI-260).

$^1$H NMR: δ6.022 (m, 1H, H-2), 5.99 (s, 2H, H-3', H-5'), 4.38 (br s, 1H, OH), 3.660 (s, 3H, OMe), 2.217 (s, 6H, C-7', C-8', Me), 1.981 (d, 3H, J=1.5 Hz, C-6, Me). HRMS: calcd for $C_{15}H_{16}O_4$ ($M^+$) 260.1049, found 260.1075.

EXAMPLE 45

Preparation of compounds PBI-91, PBI-150, PBI-264, PBI-268, PBI-270, PBI-276, PBI-277

The compounds were prepared using the method described by Lamb and Abrams in 1990 Can. J. Chem. 68:1151–1162, hereby incorporated by reference.

Spectroscopic data for these compounds is as follows:

(–)-(1'R, 2'R)-5', 6'-Dihydroabscisic alcohol (PBI-276).

$^1$H NMR: δ6.815 (d, 1H, J=15.5 Hz, H-4), 6.096 (d, 1H, J=15.5 Hz, H-5), 5.618 (t, 1H, J=6.9 Hz, H-2), 4.339 (dd, 2H, J=6.9, 0.6 Hz, OCH$_2$), 2.479 (d, 1H, J=14.8 Hz, H-5'), 2.378-2.113 (m, 4H, H-2', H-3', H-5'), 1.901 (d, 3H, J=0.76 Hz, C-6, Me), 1.594 (brs, 2H, OH), 1.033 (s, 3H, C-8', Me), 0.909 (s, 3H, C-9', Me) 0.867 (s, 3H, C-7', Me). $[\alpha]_D$–38.6_ (MeOH).

(–)-(1'R, 2'R)-(2E, 4Z)-5-(1'-hydroxy-2',6',6'-trimethy-cyclohexa- 4'-onyl)-3-methylpent-2,4-dien-1-ol (PBI-277).

$^1$H NMR: δ6.457 (d, 1H, J=15.7 Hz, H-4), 6.013 (d, 1H, J=15.7 Hz, H-5), 5.736 (t, 1H, J=6.8 Hz, H-2), 4.301 (d, 2H, J=6.8 Hz, OCH$_2$), 2.477 (d, 1H, J=14.9 Hz, H-5'), 2.368-2.263 (m, 4H, H-2', H-3', H-5'), 1.825 (s, 3H, C-6, Me), 1.561(br s, 2H, OH), 1.024 (s, 3H, C-9', Me), 0.899 (s, 3H, C-8', Me) 0.857 (d, 3H, J=6.2 Hz, C-7', Me). $[\alpha]_D$–51.0_ (MeOH).

(+)-(1'R, 2'R)-5',6'-Dihydroabscisic alcohol (PBI-91).

$^1$H NMR: δ6.811 (d, 1H, J=15.5 Hz, H-4), 6.088(d, 1H, J=15.5 Hz, H-5), 5.618 (t, 1H, J=7.1 Hz, H-2), 4.329 (d, 2H, J=7.1, OCH$_2$), 2.479 (d, 1H, J=14.8 Hz, H-5'), 2.378-2.113 (overlap 3H, H-2', H-3', H-5'), 2.1279 (dd, 1H, J=14.8, 2.0 Hz, H-5'a), 1.892 (s, 3H, C-6, Me), 1.594 (br s, 1H, OH), 1.024 (s, 3H, C-8', Me) 0.901 (s, 3H, C-9', Me), 0.860 (s, 3H, C-7', Me) HRMS: calcd for $C_{15}R_{24}O_3$ ($M^+$) 252.1744, found 252.1725 $[\alpha]_D$+42.6_ (c 1.03, MeOH).

(–)-(1'R, 2'R)-(2E)-5-(1'-hydroxy-2',6',6'-trimethy-cyclohexa- 4'-onyl)-3-methylpent-2-en-4-yn-1-ol (PBI-150).

IR $n_{max}$ cm$^{-1}$ (CHCl$_3$): 3600 (OH), 1710 (C=O). $^1$H NMR: δ6.01 (ddq, 1H, J=6.7, 6.7, 1.5 Hz, H-2), 4.23(dd, 2H, J=5.8, 5.8 Hz, OCH$_2$), 2.65 (d, 1H, J=14.3 Hz, H-5'e), 2.29 (m, 3H, H-2', H-3'), 2.07 (dd, 1H, J=14.3, 2.0 Hz, H-5'a), 1.84 (m, 3H, C-6, Me), 1.47 (dd, 1H, J=5.8, 5.8 Hz, OH), 1.18 (s, 3H, C-9', Me) 1.12 (m, 3H, C-7', Me), 0.96 (s, 3H, C-8', Me). HRMS: calcd for $C_{13}H_{18}O_3$ ($M^+$–28) 222.1256, found 222.1227. $[\alpha]_D$ –22.5 (c 0.98, MeOH).

(–)-(1'R, 2'R)-(2E)-5-(1'-hydroxy-2',6',6'-trimethy-cyclohexa- 4'-onyl )-3-methylpent-2-en-4-yn-1-al (PBI-264).

IR $n_{max}$ cm$^{-1}$ (CHCl$_3$): 3610 (OH), 1720 (C=O),1670 (CHO), 1605 (C=C). $^1$H NMR: δ10.030 (d, 1H, J=7.8 Hz, CHO), 6.229 (dq, 1H, J=7.8, 1.4 Hz, H-2), 2.607 (d, 1H, J=14.4 Hz, H-5'e), 2.38-2.15 (overlap 3H, H-2', H-3'), 2.325 (d, 3H, J=1.5 Hz, C-6, Me), 2.125 (dd, 1H, J=14.4, 2.3 Hz, H-5'a), 2.090 (br s, 1H, OH), 1.204 (s, 3H, C-9', Me), 1.145 (d, 3H, J=5.7 Hz, C-7', Me), 0.996 (s, 3H, C-8', Me). HRMS: calcd for $C_{15}H_{20}O_3$ ($M^+$–28) 248.1403, found 248.1412. $[\alpha]_D$–27.9 (c 1.01, MeOH).

(+)-(1'S, 2'S)-(2E)-5-(1'-hydroxy-2',6',6'-trimethy-cyclohexa- 4'-onyl )-3-methylpent-2-en-4-yn-1-ol (PBI-267).

IR $n_{max}$ cm$^{-1}$ (neat): 3400 (OH), 1700 (C=O). $^1$H NMR: δ6.025 (tq, 1H, J=6.8, 1.5 Hz, H-2), 4.242 (d, 2H, J=6.8 Hz, H-2), 2.658 (d, 1H, J=14.3 Hz, H-5'e), 2.34-2.23 (overlap 3H, H-2', H-3'), 2.077 (dd, 1H J=14.3, 1.8 Hz, H-5'a), 1.999 (br s, 1H, OH), 1.849 (d, 3H, J=0.6 Hz, C-6, Me), 1.194 (s, 3H, C-9', Me) 1.132 (d, 3H, J=5.8 Hz, C-7', Me), 0.997 (s, 3H, C-8', Me). HRMS: calcd for $C_{15}H_{22}O_3$ ($M^+$) 250.1575, found 250.1569. $[\alpha]_D$ +22.7 (c 1.0, MeOH).

(+)-(1'S, 2'S)-(2E)-5-(1'-hydroxy-2',6',6'-trimethy-cyclohexa- 4'-onyl)-3-methylpent-2-en-4-yn-1-al (PBI-268).

IR $n_{max}$ cm$^{-1}$ (CHCl$_3$): 3610 (OH), 1720 (C=O), 1670 (CHO), 1605 (C=C). $^1$H NMR: δ10.030 (d, 1H, J=7.6 Hz, CHO), 6.229 (dq, 1H, J=7.6, 1.4 Hz, H-2), 2.608 (d, 1H, J=14.4 Hz, H-5'e), 2.38-2.15 (overlap 3H, H-2', H-3'), 2.325 (d, 3H, J=1.5 Hz, C-6, Me), 2.126 (dd, 1H, J=14.4, 2.3 Hz, H-5'a), 2.079 (br s, 1H, OH), 1.205 (s, 3H, C-9', Me), 1.146 (d, 3H, J=5.8 Hz, C-7', Me) 0.997 (s, 3H, C-8', Me). HRMS: calcd for $C_{15}H_{20}O_3$ ($M^+$) 248.1403, found 248.1412. $[\alpha]_D$ +24.1 (c 1.48, MeOH).

(–)-(1'S, 2'S)-(2E, 4Z)-5-(1'-hydroxy-2',6',6'-trimethy-cyclohexa- 4'-onyl )-3-methylpent-2,4-dien-1-ol (PBI-270).

IR $n_{max}$ cm$^{-1}$ (neat): 3400 (OH), 1700 (C=O), 1625 (C=C). $^1$H NMR: δ6.463 (d, 1H, J=15.7 Hz, H-4), 6.046 (d, 1H, J=15.7 Hz, H-5), 5.765 (t, 1H, J=6.8 Hz, H-2), 4.312 (d, 2H, J=6.8 Hz, OCH$_2$), 2.484 (d, 1H, J=14.9 Hz, H-5'), 2.36-2.18 (overlap 3H, H-2', H-3'), 2.135 (dd, 1H J=14.9, 2.5 Hz, H-5'), 1.836 (s, 3H, C-6, Me), 1.483 (br s, 1H, OH), 1.033 (s, 3H, C-9', Me), 0.908 (s, 3H, C-8', Me), 0.867 (d, 3H, J=6.2 Hz, C-7', Me) HRMS: calcd for $C_{15}H_{24}O_3$ ($M^+$) 252.1728, found 252.1725. $[\alpha]_D$+49,9 (c 2.89, MeOH).

EXAMPLE 46

Preparation of compounds PBI-135, PBI-168–171, PBI-173–175, PBI-281

These compounds were prepared using the method described by Lamb and Abrams in 1990 Can. J. Chem. 68:1151–1162, hereby incorporated by reference, except that the starting ring compound was (±)-(8R*, 10S*)-8-acetoxymethyl- 3,3,8,10-tetramethyl-1,5-dioxaspiro[5,5]undecan-9-one.

Spectroscopic data for the resulting compounds is as follows:

(±)-9-(1E, 3Z)-(8R*, 9S*, 10S*)-8-acetoxymethyl-9-(5-hydroxy- 3-methyl-1,3-pentadienyl)-3,3,8,10-tetramethyl-1, 5-dioxaspiro[ 5,5]undecan-9-ol (PBI-135).

$^1$H NMR δ (ABA numbering): 6.71 (d, J=15.5 Hz, 1H, H-5), 5.90 (d, J=15.5 Hz, 1H, H-4), 5.56 (t, J=7.1 Hz, 1H, H-2), 4.40 and 4.33 (2d, J=11.1 Hz, H$_2$C-8') overlaps with 4.33 (d, J=7.1 Hz, H$_2$C-1) (4H), 3.45 (m, 4H, 2CH$_2$O—), 2.43 (dd, J=14.8, 3.0 Hz, 1H, H-5'eq), 2.18 (m, H-2'ax), 2.06 (s, CH$_3$COO), 1.86 (s, 3H, H$_3$C-6), 1.33 (d, J=14.9 Hz, H-5'ax) overlaps with 1.29–1.41 (m, H-3'eq, ax) (3H), 0.97, 0.88, 0.84 (3s, 3CH$_3$) and 0.78 (d, J=6.6 Hz, H$_3$C-7')(12H); $^{13}$C NMR δ:170.9 (COO), 134.5, 129.6, 128.2 and 127.5 (4 olefinic C), 96.8 (O—C—O), 79.4, 70.5, 70.0, 68.6, 58.4, 41.7, 40.0, 37.7, 33.9, 30.0, 22.5, 22.4, 21.3, 21.1, 20.9, 15.3; CIMS (ammonia): m/z 414 [M+18]$^+$ (100), 397 [M+1]$^+$ (22). Anal. found: C, 66.70; H, 9.26. $C_{22}H_{36}O_6$ requires: C, 66.62; H, 9.16.

(±)-9-(1E, 3Z)-(8R*, 9S*, 10S*)-8-Acetoxymethyl-9-(4-carbomethoxy- 3-methyl-1,3-butadienyl)-3,3,8,10-tetramethyl- 1,5-dioxaspiro[5, 5]undecan-9-ol (PBI-281)

$^1$H NMR δ (ABA numbering): 7.80 (d, J=6.0 Hz, 1H, H-4), 6.28 (d, J=6.0 Hz, 1H, H-5), 5.69 (s, 1H, H-2), 4.42 and 4.30 (2d, J=11.2 Hz, 2H, H$_2$C-8'), 3.68 (s, 3H, CH$_3$O), 3.45 (m, 4H, 2CH$_2$O), 2.46 (dd, J=14.8, 3.0 Hz, 1H, H-5eq), 2.06 (s, CH$_3$COO) and 2.00 (s, H$_3$C-6) (6H), 0.98, 0.88, 0.85 (3s, 3CH$_3$) and 0.80 (d, J=6.6 Hz, H$_3$C-7') (12H); $_3$C NMR δ: 170.8 and 166.6 (2COO), 149.9, 135.9, 128.7 and 117.1 (4 olefinic C), 96.8 (O—C—O), 79.4, 70.5, 70.0, 68.5, 51.0, 41.7, 40.0, 37.9, 34.0, 30.1, 22.5, 22.4, 21.3, 21.2, 15.3; EIMS: m/z 424 [M]$^+$ (10), 393 [M-31]$^+$ (2), 364 [M-60]$^+$ (10), 309 (95), 229 (60), 155 (100); CIMS (ammonia): m/z 442 [M+18]$^+$ (100), 407 [M-17]$^+$ (28); HRMS: [M]$^+$ at m/z 424.2524 ($C_{23}H_{36}O_7$ requires 424.2587). Anal. found: C, 65.27; H, 8.48. $C_{23}H_{36}O_7$ requires: C, 65.06; H, 8.55.

(±)-4-(1E, 3Z)-(3R*, 4S*, 5S*)-4-(4-carbomethoxy-3-methyl- 1,3-butadienyl)-4-hydroxy-3-hydroxymethyl-3,5-dimethylcyclohexan-1-one [PBI-168, or 8'-acetoxy-2',3'-dihydroabscisic acid, methyl ester] PBI-168 was obtained by recrystallization from CHCl$_3$-hexane, m.p. 184°–186° C. Anal. found: C, 63.68; H, 7.87. $C_{18}H_{26}O_6$ requires: C, 63.87; H, 7.75%. PBI-171 was reacted with ethereal diazomethane to give methyl ester PBI-169, m.p. 138°–148° C., which had the following spectral properties: IR $n_{max}$ cm$^{-1}$: 3600, 3450, 1700; EIMS: m/z 278 [M–18]$^+$ (7), 248 (5), 219 (14), 191 (100); CIMS (ammonia ): m/z 314 [M+18]$^+$ (100), 297 [M+1]$^+$ (4), 296 [M]$^+$ (8), 279 [M–18+1]$^+$ (30); CIMS (isobutane): m/z 297 [M+1]$^+$ (6), 279 [M–18+1]$^+$ (62), 249 (100); trimethylsilyl ether derivative CIMS (ammonia): m/z 386 [M+18]$^+$ (27), 369 [M+1]$^+$ (9), 368 [M]$^+$ ( 12), 351 [M–18+1]$^+$ (45). Anal. found: C, 64.57; H, 8.43. $C_{16}H_{24}O_5$ requires: C, 64.83; H 8.17%.

(±)-4-(1E, 3Z)-(3R*, 4S*, 5S*)-4-(4-carboxy-3-methyl-1,3-butadienyl)- 4-hydroxy-3-hydroxymethyl-3,5-dimethyl-cyclohexan-1-one [(PBI-171, or 8'-hydroxy-2',3'-dihydroabscisic acid] and methyl ester PBI-170

Compound PBI-170 was characterized as the methyl ester PB-170, m.p. 138°–148° C., which had the following spectral properties: IR $n_{max}$ cm$^{-1}$: 3600, 3450, 1700; EIMS: m/z 278 [M–18]$^+$(7), 248 (5), 219 (14), 191 (100); CIMS (ammonia): m/z 314 [M+18]$^+$ (100), 297 [M+1]$^+$(4), 296 [M]$^+$ (8), 279 [M–18+1]$^+$ ( 30); CIMS (isobutane): m/z 297 [M+1]$^+$ (6), 279 [M–18+1]$^+$ (62), 249 (100); trimethylsilyl ether derivative CIMS (ammonia): m/z 386 [M+18]$^+$ (27), 369 [M+1]$^+$ (9), 368 [M]$^+$ (12), 351 [M–18+1]$^+$ (45). Anal. found: C, 64.57; H, 8.43. $C_{16}H_{24}O_5$ requires: C, 64.83; H 8.17%.

(+)-1-(1E, 3Z)-(1S, 4R, 6S)-1-(4-carboxy-3-methyl-1,3-butadienyl)- 2,2,6-trimethylcyclohexan-1,4-diol (PBI-175)

$^1$H NMR δ: 7.71 (d, J=16.0 Hz, 1H, H-4), 6.43 (d, J=16.0 Hz, 1H, H-5), 5.70 (s, 1H, H-2), 4.02 (dddd, J=11.4, 11.4, 4.9

4.9 Hz, 1H, H-4'ax), 2.03 (d, J=0.9 Hz, H$_3$C-6) and 2.04 (m, H-2'ax) (4H), 1.88 (dddd, J=12.2, 4.9, 3.2, 3.2 Hz, 1H, H-3'eq), 1.71 (ddd, J=12.2, 4.7, 2.3 Hz, 1H, H-5'eq), 1.48 (dd, J=12.2, 11.5 Hz, 1H, H-5'ax), 1.24 (m, 1H, H-3'ax), 1.08 and 0.81 (2s, 3H each, H$_3$C-8',9'), 0.79 (d J=6.9 Hz, 3H, H$_3$C-7'); HRMS: [M$^+$] at m/z 268.1687 (C$_{15}$H$_{24}$O$_4$ requires 268.1675).

PBI-174 gave identical NMR and MS data and m.p. 98°–103° C. [α]$_D$=+58.1° (c=0.78).

PBI-173 gave identical NMR and MS data and m.p. 151°–156° C.; [α]$_D$=–63.2° (c=0.62).

EXAMPLE 47

Preparation of compounds PBI-197–205

These compounds were prepared using the method described by Lam and Abrams in 1992 Phytochemistry 31:1105–1110, hereby incorporated by reference. Spectroscopic data for these compounds is as follows: (2E)-5-(2-Difluoromethyl-4,4-ethylenedioxy-6,6-dimethylcyclohex-2-enyl )-3-methylpent-2-en-4-yn-1-ol (PBI 197).

$^1$H NMR: δ6.40 (t, 1H, J=55.4 Hz, H-7'), 5.96 (s, 1H, H-3'), 5.88 (m, 1H, H-2), 4.24 (d, 2H, J=7 Hz, H-1), 3.95 (s, 4H, OCH$_2$), 2.68 (bs, 1H, OH), 2.00 (d, 1H, J=14.3 Hz, H-5'), 1.92 (d, 1H, J=14.3 Hz, H-5'), 1.85 (s, 3H, C-6, CH$_3$), 1.13 (s, 3H, C-8', CH$_3$), 1.10 (s, 3H, C-9', CH$_3$).

(2Z,4E)-5-(2-Difluoromethyl-4,4-ethylenedioxy-6,6-dimethylcyclo-hex- 2-enyl)-3-methylpenta-2,4-dien-1-ol (PBI198).

$^1$H NMR: δ6.63 (d, 1H, J=15.8 Hz, H-5), 6.06 (t, 1H, J=55.1 Hz, H-7', overlapping s, 1H, H-3'), 5.70 (d, 1H, J=15.8 Hz, H-4), 5.59 (t, 1H, J=7 Hz, H-2), 4.25–4.32 (m, 2H, H-1), 3.92–4.03 (m, 4H, OCH$_2$), 1.97 (d, 1H, J=14.3 Hz, H-5'), 1.83 (s, 3H, C-6, CH$_3$), 1.77 (d, 1H, J=14.3 Hz, H-5'), 1.06 (s, 3H, C-8', CH$_3$), 0.91 (s, 3H, C-9', CH$_3$).

(2Z,4E)-5-(2-Difluoromethyl-4,4-ethylenedioxy-6,6-dimethylcyclo-hex- 2-enyl)-3-methylpenta-2,4-dien-1-al (PBI 199).

$^1$H NMR: δ10.17 (d, 1H, J=8 Hz, H-1), 7.32 (d, 1H, J=15.6 Hz, H-5), 6.11 (d, 1H, J=15.6 Hz, H-4), 6.10 (t, 1H, J=55 Hz, H-7'), 6.08 (s, 1H, H-3'), 5.88(d, 1H, J=8 Hz, H-2), 3.94–4.04 (m, 4H, OCH$_2$), 2.06 (s, 3H, C-6, CH$_3$), 1.93 (d, 1H, J=15 Hz, H-5'), 1.83 (d, 1H, J=15 Hz, H-5'), 1.09 (s, 3H, C-8', CH$_3$), 0.94 (s, 3H, C-9', (CH$_3$).

Methyl (2Z,4E)-5-(2-difluoromethyl-4,4-ethylenedioxy-6,6-dimethyl-cyclohex- 2-enyl )-3-methylpenta-2,4-dienoate (PBI 200).

$^1$H NMR: δ7.77 (d, 1H, J=16.1 Hz, H-5), 6.11 (t, 1H, J=55 Hz, H-7'), 6.06 (d, 1H, J=16.1 Hz, H-4, overlapping s, 1H, H-3'), 5.70 (s, 1H, H-2), 3.93–4.04 (m, 4H, OCH$_2$), 3.69 (s, 3H, CO$_2$CH$_3$), 1.97 (s, 3H, C-6, CH$_3$), 1.93 (d, 1H, J=14.5 Hz, H-5'), 1.82 (dd, 1H, J=16.1, J'=1 Hz, H-5'), 1.08 (s, 3H, C-8', CH$_3$), 0.92 (s, 3H, C-9', CH$_3$).

Methyl 7',7'-difluoroabscisate (PBI 201 (racemic), 202 (+) and 203 (–)).

$^1$H NMR: δ7.84 (d, 1H, J=16.1 Hz, H-5), 6.31 (t, 1H, J=54.3 Hz, H-7'), 6.34 (s, 1H, H-3'), 6.11 (d, 1H, J=16.1 Hz, H-4), 5.75 (s, 1H, H-2), 3.66 (s, 3H, CO$_2$CH$_3$), 2.54 (s, 1H, OH), 2.47 (d, 1H, J=7.1 Hz, H-5'), 2.38 (d, 1H, J=7.1 Hz, H-5'), 1.98(d, 3H, J=1 Hz, C-6, CH$_3$), 1.10 (s, 3H, C-8', CH$_3$), 1.02 (s, 3H, C-9', CH$_3$).

(+)-Methyl 7',7'-difluoroabscisate showed the following properties: [α]=(+) 286.3; mp=91–93. (–)-Methyl 7',7'-difluoroabscisate showed the following properties: [α]=(–) 306.76; mp=90–91.

(+) and (–)-7',7'-Difluoroabscisate (PBI 204 (+) and 205 (–)).

$^1$H NMR: δ7.79 (d, 1H, J=16.2 Hz, H-5), 6.32 (t, 1H, J=55.6 Hz, H-7'), 6.37 (s, 1H, H-3'), 6.14 (d, 1H, J=16.3 Hz, H-4), 5.79 (s, 1H, H-2), 2.53 (d, 1H, J=17.2 Hz, H-5'), 2.41 (d, 1H, J=17.2 Hz, H-5'), 2.06 (d, 1H, J=1 Hz, C-6, CH$_3$), 1.14 (s, 3H, C-8', CH$_3$), 1.06 (s, 3H, C-9', CH$_3$).

(+)-7',7'-Difluoroabscisic acid showed the following properties: mp 155–156, (hexane/Et$_2$O); [α]=(+)–283.25. (–)-7',7'-Difluoroabscisic acid showed the following properties: [α]=(–)–296.19; mp 156–158.

EXAMPLE 48

Preparation of compounds PBI-193–196, PBI-207, PBI-208, PBI-216–221.

These compounds were prepared using the method described by Rose et al. in 1992 Tetrahedron: Asymmetry 3, pp. 443–450, hereby incorporated by reference.

Spectroscopic data for these compounds is as follows:

(–)-4(Z)-(4R)-4-Hydroxy-4-(5-hydroxy-3-methylpent-3-en-1-ynyl)- 3, 5, 5-trimethylcyclohex-2-enone, (PBI 207) and (+) form, (PBI 216).

$^1$H NMR: δ5.90 (m, 1H-3'), 5.82 (s , 1H-2), 4.24 (d, 2H-1, J=7 Hz), 2.47 (d, 1H-5', J=16 Hz), 2.38 (d, 1H-5', J=16 Hz), 2.10 (s, 3H-7'), 1.85 (s , 3H-6), 1.18 (s, 3H-8'/9'), 1.08 (s, 3H-8'/9'); $^{13}$C NMR: d 198.4 (C=O), 160.3 (C=), 136.8 (C=)m 126.0 (C=), 120.0 (C=), 92.8, 85.3, 74.7, 61.1, 49.2, 41.8, 25.2, 22.9, 21.9, 19.7. PBI 216 has the following rotation: [α]=(+)–255.2 [MeOH, c 1.25]. PBI 207 showed the following rotation: [α]=(–)–264.6 [MeOH, c 1.05].

(–)-4(Z)-(4R)-4-Hydroxy-4-(5-oxo-3-methylpent-3-en-1-ynyl)- 3,5,5-trimethylcyclohex-2-enone, (PBI 208) and (+) form, (PBI 217).

$^1$H NMR: δ9.93 (d, 1H-1, J=1, 8 Hz), 6.21 (dd, 1H-2, J=1.5, 8 Hz), 5.87 (brd, 1H-3', J=2 Hz), 2.94 (s, 1H, OH), 2.45 (d, 1H-5', J=2 Hz), 2.11 (s, 6H-6,7'), 1.21 (s, 3H-8'/9'), 1.11 (s, 3H-8'/9'); $^{13}$C NMR: d 197.5 (C=O), 191.7 (C=O), 154.6 (C=), 140.7 (C=), 136.1 (C=), 126.6 (C=), 98.9, 83.6, 75.0, 49.1, 42.0, 25.2, 24.7, 21.9, 19.7. PBI 208 showed the following rotation: [α]=(–)–294.4 [MeOH, c 1.21]. PBI 217 showed the following rotation: [α]=(+)–308.2 [MeOH, c 1.03].

(+)-4 (Z)-(4R)-4-Hydroxy-4-(5-carboxymethyl-3-methylbut- 3-en-1-ynyl)-3,5,5-trimethylcyclohex-2-enone (PBI 194) and (–) form, (PBI 193).

$^1$H NMR: δ6.01 (d, 1H-3', J=1 Hz), 5.83 (d, 1H-2, J=0.5 Hz), 3.67 (s, 3H-1), 3 34 (br s, 1H, OH), 2.58 (d, 1H-5', J=16 Hz), 2.38 (d, 1H-5', J=16 Hz), 2.12 (d, 3H-7', J=1 Hz), 2.00 (d, 3H-6, J=1 Hz), 1.21 (s, 3H-8'/9'), 1.09 (s, 3H-8'/9'). PBI 194 showed the following rotation: [α]=(+)–238.3 [MeOH, c 1.26]. PBI 193 showed the following rotation: [α]=(–)–225.0 [MeOH, c 1.33]

(+)-4(Z)-(4R)-4-Hydroxy-4-(5-carboxy-3-methylbut-3-en-1-ynyl)- 3,5,5-trimethylcyclohex-2-enone, (PBI 196) and (–) form, (PBI 195).

$^1$H NMR: δ6.03 (d, 1H-3', J=1 Hz), 5.86 (s , 1H-2), 2.63 (d, 1H-5', J=16 Hz), 2.38 (d, 1H-5', J=16 Hz), 2.10 (d, 3H-7', J=1 Hz), 2.04 (d, 3H-6, J=1 Hz), 1.21 (s, 3H-8'/ 9'), 1.09 (s, 3H-8'/9'). PBI 196 showed the following rotation: [α]=(+)–283.5 [MeOH, c 0.45]. PBI 195 showed the following rotation: [α]=(–)–278.8 [MeOH, c 1.67].

(+)-Abscisyl alcohol, (PBI 218), and (−) form (PBI 220). [α]=(+)−372.5 [MeOH, c 1.25]; HREIMS: [M$^+$] at m/z 250.1575 ($C_{15}H_{22}O_3$ requires 250.1569); IR $u_{max}$ cm$^{-1}$: 3600 (w, O—H), 1660 (C=O); $^1H$ NMR: δ 6.72 (d, 1H-5, J=16 Hz), 5.89 (s, 1H-3'), 5.78 (d, 1H-4, J=16 Hz), 5.60 (m, 1H-2), 4.27 (d, 2H-1, J=5.5 Hz), 2.43 (d, 1H-5', J=17 Hz), 2.24 (d, 1H-5', J=17 Hz), 1.87 (s, 3H-7'), 1.84 (s, 3H-6), 1.67 (bs, 1H, OH), 1.07 (s, 3H-8'/9'), 0.98 (s, 3H-8'/9'); $^{13}C$ NMR: δ198.0 (C=O), 162.9 (C=), 134.1 (C=), 130.7 (C=), 129.5 (C=), 127.0 (C=), 126.8 (C=), 79.6, 59.2, 58.3, 49.8, 41.4, 24.2, 23.0, 20.6, 18.9, 12.8. PBI 220 has the following rotation: [α]=(−)−362.0 [MeOH, c 1.04]

(+)-Abscisyl aldehyde, (PBI 219), and (−) form (PBI 221). [α]=(+)−451.7 [MeOH, c 1.38]; HREIMS: [M$^+$] at m/z 248.1399 ($C_{15}H_{20}O_3$ requires 248.1412); IR $u_{max}$ cm$^{-1}$: 3600 (w, O—H), 1665 (C=O); $^1$H NMR: δ10.16 (d, 1H-1, J=8 Hz), 7.46 (d, 1H-5, J=15.5 Hz), 6.18 (d, 1H-4, J=15.5 Hz), 5.90 (m, 2H-2',3), 2.45 (d, 1H-5', J=17 Hz), 2.31 (d, 1H-5', J=17 Hz), 2.06 (d, 3H-6, J=1 Hz), 1.89 (d, 3H-7', J=1 Hz), 1.09 (s, 3H-8'/9'), 1.01 (s, 3H-8'/9'); $^{13}C$ NMR: δ197.3 (C=O), 190.1 (C=O), 161.7 (C=), 153.0 (C=), 137.6 (C=), 129.3 (C=), 127.2 (C=), 126.0 (C=), 79.6, 49.7, 41.5, 24.3, 23.0, 21.5, 18.8. PBI 221 has the following rotation: [α]=(−)−451.5 [MeOH, c 1.04].

EXAMPLE 49

Preparation of compounds PBI-262, PBI-263, PBI-274 and PBI-275.

These compounds were prepared by stirring the appropriate starting material with trimethylsilyl chloride and 1,8-diazobicyclo [5.4.0]undecane.

Spectroscopic data for the resulting compounds is as follows:

(+)-4Z -4(R)-4-Trimethylsiloxy-4-(5-carboxymethyl-3-methyl- 2,4-butadienyl)-3,5,5-trimethylcyclohex-2-enone. (PBI 262) and the (−) form, (PBI 263).

$^1$H NMR: δ7.56 (d, 1H, J=16 Hz, HC=CH), 6.17 (d, 1H, J=16 Hz, CH=CH), 6.01 (s, 1H, =CH), 5.71 (s, 1H, =CH), 3.64 (s, 3H, COOCH$_3$), 2.22 (bs, 2H, CH$_2$), 2.00 (s, 3H, =CCH$_3$), 1.91 (s, 3H, =CCH$_3$), 1.01 (s, 3H, C(CH$_3$)$_2$), 0.99 (s, 3H, C(CH$_3$)$_2$), 0.18 (s, 9H, Si(CH$_3$)$_3$).

(+)-4Z-4(R)-4-Trimethylsiloxy-4-(5-carboxy-3-methyl-2, 4-buta dienyl)-3,5,5-trimethylcyclohex-2-enone. (PBI 274) and the (−) form (PBI 275).

$^1$H NMR: δ7.62 (d, 1H, J=16 Hz, CH=CH), 6.21 (d, 1H, J=16 Hz, CH=CH), 6.01 (d, 1H, J=1 Hz, =CH), 5.75 (s, 1H, =CH), 2.24 (bs, 2H, CH$_2$), 2.04 (d, 3H, J=1 Hz, =CCH$_3$), 1.91 (d, 3H, J=1 Hz, =CCH$_3$), 1.01 (s, 3H, C(CH$_3$)$_2$), 1.00 (s, 3H, C(CH$_3$)$_2$), 0.18 (s, 9H, Si(CH$_3$)$_3$).

EXAMPLE 50

Preparation of compounds PBI-222, PBI-224 and PBI-225

These compounds were prepared through the reaction of abscisic acid with the appropriate diol and dicyclohexylcarbodiimide.

Spectroscopic data is as follows:

6-Hydroxyhexyl abscisate, (PBI 222) (racemic), (PBI 224) (+), and (PBI 225) (−).

$^1$H NMR: δ7.80 (d, 1H, J=16 Hz, CH=CH), 6.12 (d, 1H, J=16 Hz, CH=CH), 5.90 (d, 1H, J=1 Hz, =CH), 5.72 (s, 1H, =CH), 4.09 (t, 2H, J=7 Hz, CH$_2$OH), 3.62 (t, 2H, J=6.5 Hz, CH$_2$OH), 2.44 (d, 1H, J=17 Hz, CHH), 2.26 (d, 1H, J=17 Hz, CHH), 1.98 (d, 3H, J=1 Hz, =CCH$_3$), 1.89 (d, 3H, J=1Hz, =CCH$_3$), 1.34–1.65 (m, 8H, (CH$_2$)$_4$), 1.07 (s, 3H, C(CH$_3$)$_2$), 0.98 (s, 3H, C(CH$_3$)$_2$).

EXAMPLE 51

Effect of compositions containing compound PBI-11 on the synchrony of germination and emergence of canola at 10° C.

Methods 7.3 g of 'Tobin' canola seeds were soaked for 8 hours at 25° C., in each of the following solutions: water; and one of 10, 1, or 0.1 μM PBI-11 in glass beakers. Beakers were sealed with aluminum foil to prevent evaporation and to exclude light. After incubation, solutions were removed and seeds were blotted dry with paper towels. Seeds were sandwiched between 4 layers of paper towels, which were daily changed and seeds were separated, and dried at 25° C., until their dried weight was close to their pre-soaking weight. About 100 seeds/treatment were sown, 2.5 cm deep in flats of 1:1:1 soil mix of peat, soil, and 'Vermiculite' in 4 rows 2.5 cm apart, and incubated at 10° C. in darkness. Flats were watered with cold tap water to saturation point, before incubation, and as needed. Flats were examined at daily intervals, until plants began emerging, and at 12 and 8 h. intervals as emergence progressed. The number of plants which had emerged in each interval were recorded. Results are shown in FIG. 1 wherein PBI11-5, PBI11-6 and PBI11-7 respectively correspond to concentrations of 10 μM, 1 μM and 0.1 μM of PBI-11 in solution.

EXAMPLE 52

Effect of compositions containing compounds PBI-267, PBI-268, PBI-58, PBI-91 and PBI-277 on the synchrony of germination and emergence of *Brassica napus* c.v. H0337 at 10° C.

Figure 2:
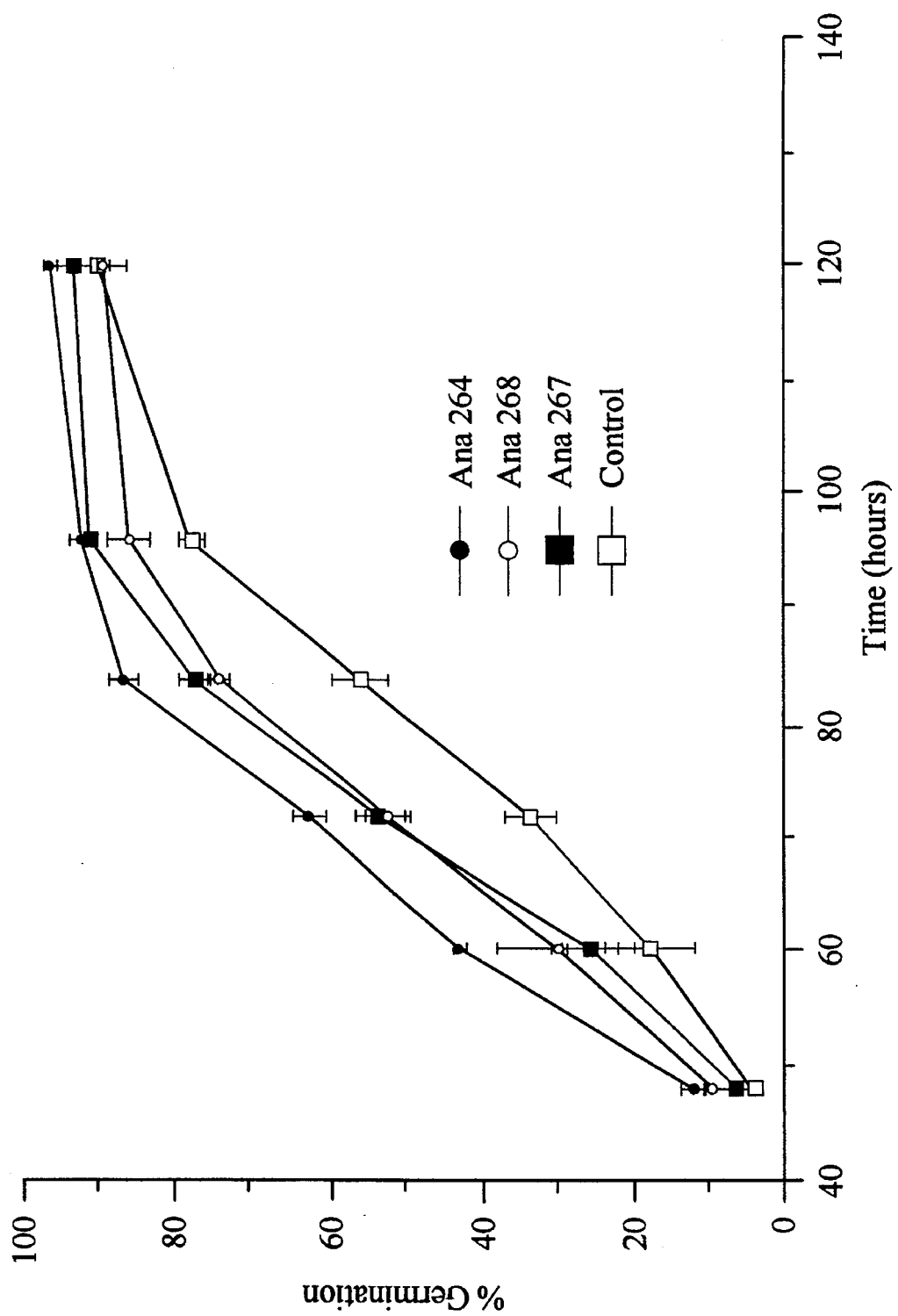
FIG. 2 represents the influence of compounds PBI-264, PBI-267 and PBI-268 on the synchrony of germination of *Brassica napus*.
Figure 3:
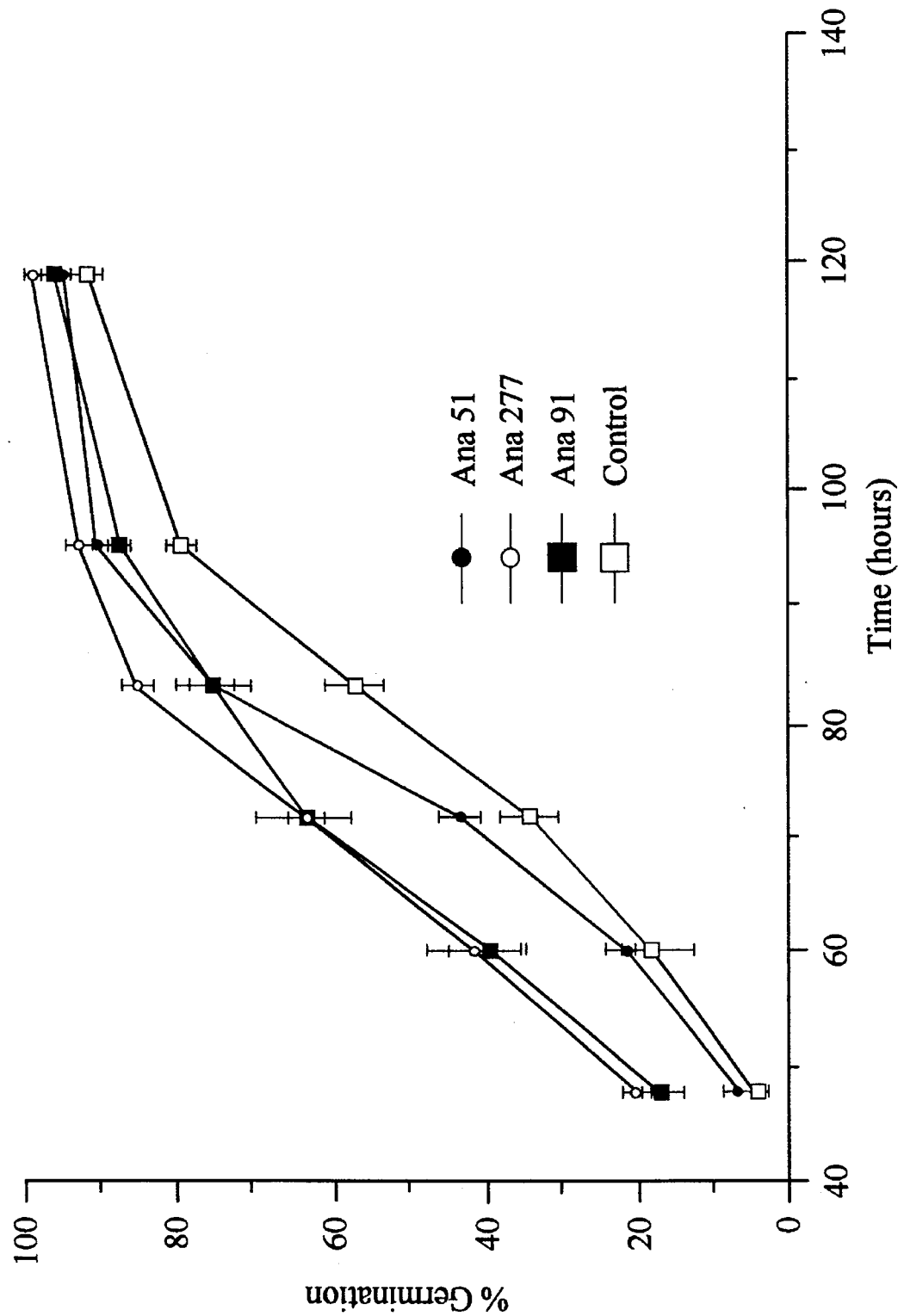
FIG. 3 represents the influence of compounds PBI-51, PBI-91 and PBI-277 on the synchrony of germination of *Brassica napus*.

Methods 7.3 g of *Brassica napus* c.v. H0337 seeds were soaked for 8 hours at 25° C., in each of the following solutions: water and one of 1 μM PBI-264, 0.1 μM PBI-267, 0.01 μM PBI-268, 1 μM PBI-51, 1 μM PBI-91 and 1 μM PBI-277 in glass beakers. Beakers were sealed with aluminum foil to prevent evaporation and to exclude light. After incubation, solutions were removed and seeds were blotted dry with paper towels. Seeds were sandwiched between 4 layers of paper towels, which were daily changed and seeds were separated, and dried at 25° C., until their dried weight was close to their pre-soaking weight. About 100 seeds/treatment were sown, 2.5 cm deep in flats of 1:1:1 soil mix of peat, soil, and 'Vermiculite' in 4 rows 2.5 cm apart, and incubated at 10° C. in darkness. Flats were watered with cold tap water to saturation point, before incubation, and as needed. Flats were examined at daily intervals, until plants began emerging, and at 12 and 8 h. intervals as emergence progressed. The number of plants which had emerged in each interval were recorded. Results are shown in FIGS. 2 and 3.

EXAMPLE 53

Effect of compositions containing compound PBI-11 on the synchrony of germination and emergence of golden beauty corn at 10° C.

Figure 4:
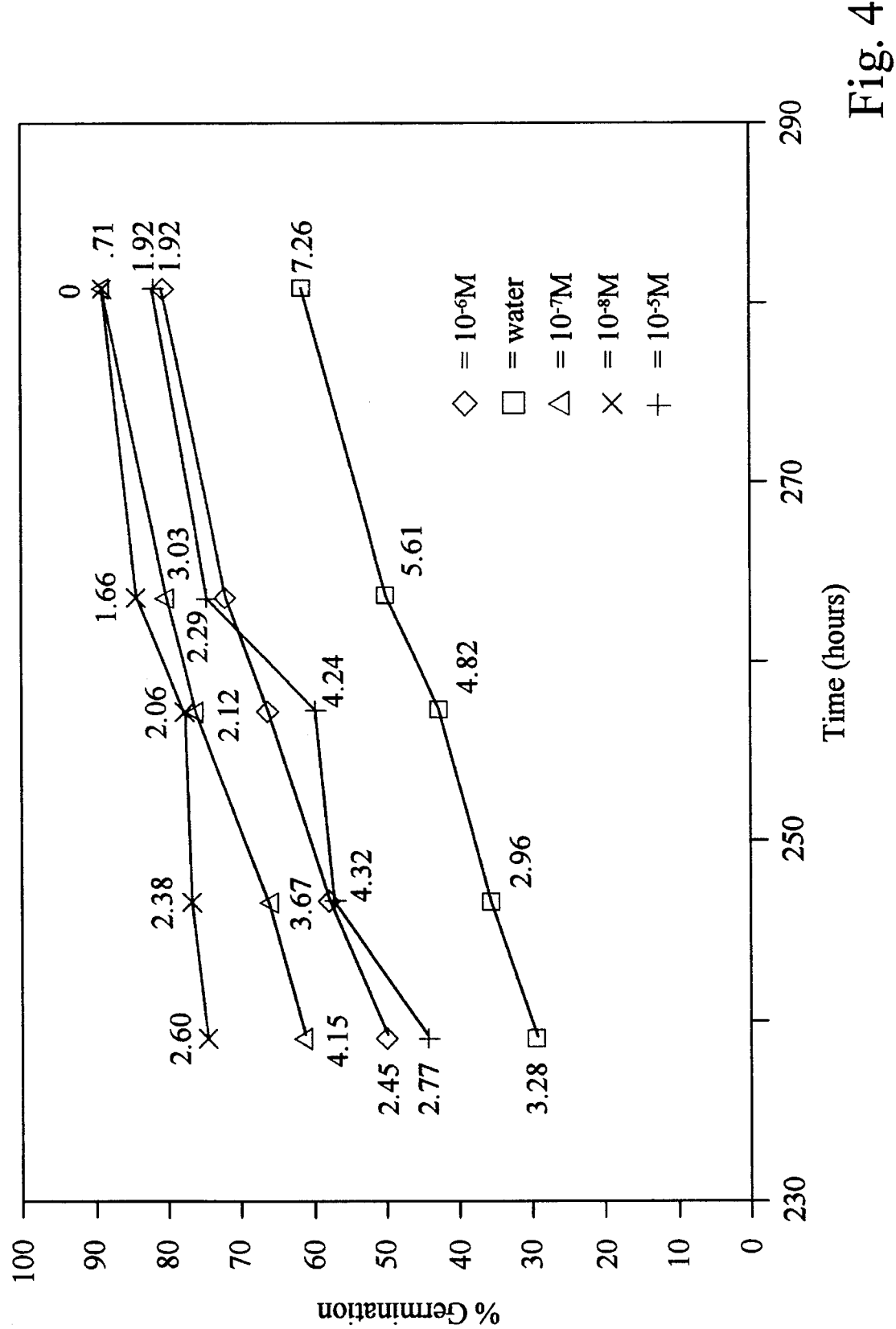
FIG. 4 represents the influence of various concentrations of compound PBI-11 on the synchrony of germination of golden beauty corn.

Methods 7.3 g of golden beauty corn seeds were soaked for 8 hours at 25° C., in each of the following solutions: water, and one of 10, 1, 0.1 or 0.01 μM PBI-11 in glass beakers. Beakers were sealed with aluminum foil to prevent evaporation and to exclude light. After incubation, solutions were removed and seeds were blotted dry with paper towels. Seeds were sandwiched between 4 layers of paper towels, which were daily changed and seeds were separated, and dried at 25° C., until their dry weight was close to their pre-soaking weight. About 100 seeds/treatment were sown, 2.5 cm deep in flats of 1:1:1 soil mix of peat, soil, and 'Vermiculite' in 4 rows 2.5 cm apart, and incubated at 10° C. in darkness. Flats were watered with cold tap water to saturation point, before incubation, and as needed. Flats were examined at daily intervals, until plants began emerging, and at 12 and 8 h. intervals as emergence progressed. The number of plants which had emerged in each interval were recorded. Results are shown in FIG. 4. As it can be seen from FIG. 4, after 240 hours, less than 30% of the non-treated seed germinated in contrast to 75% of the seed treated with PBI-11 at $10^{-8}$M.

EXAMPLE 54

Effect of compositions containing compound PBI-11 on the synchrony of germination and emergence of canola at 10° C.

Figure 5:
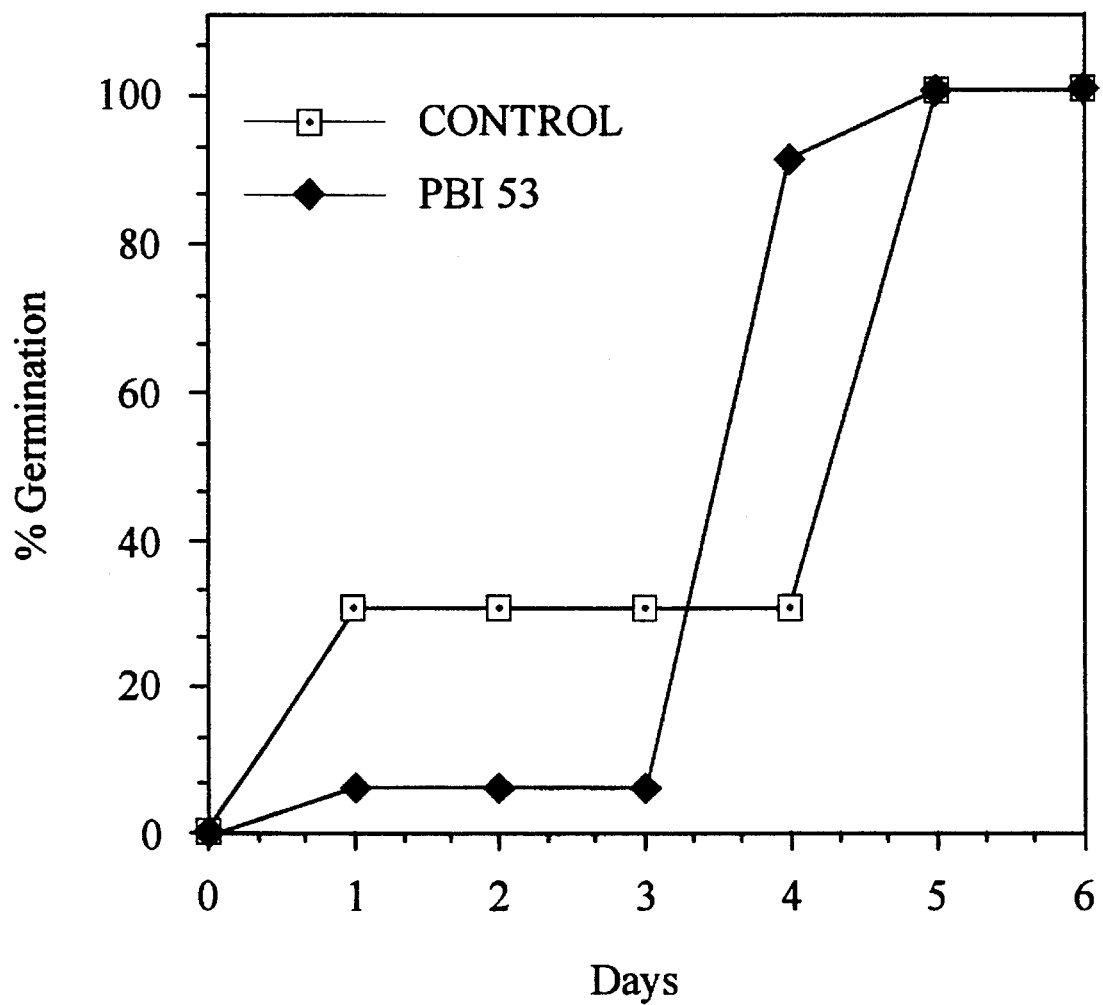
FIG. 5 represents the influence of compound PBI-53 on the synchrony of germination of carrot.

Methods 7.3 g of carrot seeds were soaked for 8 hours at 25° C., in each of the following solutions: hexane-methanol and PBI-53 in glass beakers. Beakers were sealed with aluminum foil to prevent evaporation and to exclude light. After incubation, solutions were removed and seeds were blotted dry with paper towels. Seeds were sandwiched between 4 layers of paper towels, which were daily changed and seeds were separated, and dried at 25° C., until their dry weight was close to their pre-soaking weight. About 100 seeds/treatment were sown, 2.5 cm deep in flats of 1:1:1 soil mix of peat, soil, and 'Vermiculite' in 4 rows 2.5 cm apart, and incubated at 10° C. in darkness. Flats were watered with cold tap water to saturation point, before incubation, and as needed. Flats were examined at daily intervals, until plants began emerging, and at 12 and 8 h. intervals as emergence progressed. The number of plants which had emerged in each interval were recorded. Results are shown in FIG. 5. As it can be seen from this figure, the non-treated seeds initiated germination over a few days period with approximately 30% of the seeds germinated after one day. In contrast, less than 10% of the treated seeds germinated within the first three days, but over 90% of the seeds germinated between day 3 and day 4.

We claim:

1. A method for promoting synchrony of germination and emergence in plants, said method comprising treating plant seeds or plant parts used in propagation with an effective amount of a compound having the following formula (I):

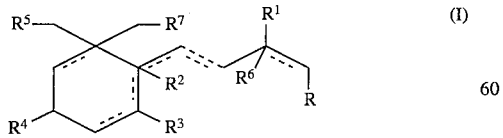

wherein

R is carboxyl, aldehyde, hydroxy, hydroxyloweralkyl, alkoxyloweralkyl, loweralkoxycarbonyl, loweracyloxyloweralkyl, acetylloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, thio, phosphate, sulfoxide, sulfone, deuterium or cycloalkyl or cycloalkoxy having from 4 to 6 carbon atoms which is optionally substituted by loweralkyl, halogen, oxygen, hydroxy or loweralkoxy;

$R^1$ is loweralkyl, hydrogen, oxo, hydroxyloweralkyl, loweralkoxy, halogen, thio, sulfoxide, sulfone, phosphate or deuterium;

$R^2$ is hydrogen, oxo, hydroxy, halogen, thio, phosphate, sulfoxide, sulfone or deuterium;

$R^3$ is oxo, thio, carboxyl, aldehyde, loweralkyl, hydroxyloweralkyl, alkoxyloweralkyl, loweralkoxycarbonyl, loweracyloxy- loweralkyl, acetylloweralkyl, loweralkanoyl, loweralkylamino, diloweralkylamino, loweralkoxy, loweracyloxy, loweralkylthio, loweralkylhalide, loweralkyldeuterium, loweralkyl sulphonyl, loweralkyl sulphinyl, or carbonyl;

when $R^2$ is oxo or thio, $R^2$ may be linked to both $C^1$ and $C^2$ carbon atoms to form an epoxy or a thioepoxy ring;

and when $R^3$ is oxo or thio, $R^3$ may be linked to the carbon atom adjacent to $R^5$ to form an epoxy or thioepoxy ring;

$R^4$ is hydrogen, oxo, halogen, thio, phosphate, sulfoxide, sulfone, deuterium, hydroxy, loweralkylsiloxane, carboxyl, aldehyde, hydroxyloweralkyl, alkoxyloweralkyl, loweralkoxycarbonyl, loweracyloxyloweralkyl, acetylloweralkyl, loweralkanoyl, loweralkyl amino, diloweralkylamino, loweralkoxy, loweracyloxy, loweralkylthio, loweralkyl sulphonyl, loweralkyl sulphinyl, amino, carbonyl, cycloalkyl or cycloalkoxy having from 4 to 6 carbon atoms which is optionally substituted by loweralkyl, halogen, oxygen, hydroxy or loweralkoxy;

and when $R^4$ is oxo or thio, $R^4$ may be linked to the carbon atom adjacent to $R^5$ to form an epoxy or thioepoxy ring;

$R^5$ is carboxyl, hydroxy, aldehyde, hydroxyloweralkyl, alkoxyloweralkyl, loweralkoxycarbonyl, loweracyloxyloweralkyl, acetylloweralkyl, acetoxyloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, hydrogen, oxo, thio, phosphate, sulfoxide, sulfone or deuterium, and when $R^5$ is oxo, it may be linked to the carbon atom bearing $R^3$;

$R^6$ is loweralkyl, hydrogen, oxo, hydroxyloweralkyl, loweralkoxy, halogen, thio, sulfoxide, sulfone, phosphate or deuterium;

$R^7$ is carboxyl, hydroxy, aldehyde, hydroxyloweralkyl, alkoxyloweralkyl, loweralkoxycarbonyl, loweracyloxyloweralkyl, acetylloweralkyl, acetoxyloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, hydrogen, oxo, thio, phosphate, sulfoxide, sulfone or deuterium, and when $R^7$ is oxo, it may be linked to the carbon atom bearing $R^3$; and wherein the dotted lines may each represent a single bond and the double dotted line represents either a double bond or a triple bond, $R^1$ or $R^6$ is absent if the dotted line adjacent to $R^1$ and $R^6$ is a single bond, $R^2$ is absent if either of the dotted lines adjacent to $R^2$ is a single bond, the alkyl group bearing $R^7$ is absent if the dotted line adjacent to the alkyl group bearing R⁷ is a single bond, and isomers and functional derivatives thereof, in admixture with an acceptable agricultural carrier comprising an agriculturally acceptable carrier cation when R, R¹, R², R⁴, R⁵, R⁶ or R⁷ are phosphate, sulfoxide or sulfone, for the purpose of enhancing synchrony of germination and emergence in plants.

2. A method according to claim 1, wherein said compound of formula I is applied to said plant seeds.

3. A method according to claim 2, wherein said compound of formula I is applied to said seeds by soaking said seeds in an agricultural composition comprising an effective concentration of said compound of formula I for the period of time required by said seeds to absorb said compound of formula I in sufficient amounts to enhance synchrony of germination and emergence of the plants resulting from said seeds.

4. A method according to claim 1, wherein the concentration of said compound of formula I ranges between 0.000005 g and 1.5 kg per acre.

5. A method according to claim 2, wherein said plant seeds are selected from canola, corn, brassica, celery and carrot seeds.

6. A method according to claim 1, wherein in said compound of formula I:

R is carboxyl, aldehyde, hydroxy, hydroxyloweralkyl, alkoxyloweralkyl, loweralkoxycarbonyl, loweracyloxyloweralkyl, acetylloweralkyl, loweralkanoyl, cycloalkoxy having from 4 to 6 carbon atoms, amino, carbonyl, halogen or thio;

R¹ is loweralkyl, hydrogen, oxo, hydroxyloweralkyl, loweralkoxy, halogen, thio, sulfoxide, sulfone, phosphate or deuterium;

R² is hydrogen, hydroxy, halogen or thio;

R³ is carboxyl, aldehyde, loweralkyl, hydroxyloweralkyl, alkoxyloweralkyl, loweralkoxycarbonyl, loweracyloxyloweralkyl, acetylloweralkyl, loweralkanoyl, loweralkylamino, diloweralkylamino, loweralkoxy, loweralkylhalide, loweracyloxy, loweralkylthio, loweralkyl sulphonyl, loweralkyl sulphinyl or carbonyl;

and when R² is thio, R² may be linked to both C₁ and C₂ carbon atoms to form a thioepoxy ring;

R⁴ is hydrogen, oxo, halogen, thio or amino;

R⁵ is hydrogen, oxo or nitrogen;

R⁶ is hydrogen;

R⁷ is hydrogen, oxo or nitrogen.

7. A method according to claim 6, wherein said compound of formula I is applied to plant seeds.

8. A method according to claim 7, wherein said compound of formula I is applied to said seeds by soaking said seeds in an agricultural composition comprising an effective concentration of said compound of formula I for the period of time required by said seeds to absorb said compound of formula I in sufficient amounts to enhance synchrony of germination and emergence of the plants resulting from said seeds.

9. A method according to claim 7, wherein said plant seeds are selected from canola, corn, brassica, celery and carrot seeds.

10. A method according to claim 7, wherein the concentration of said compound of formula I ranges between 0.00000025 g/l and 0.50 g/l.

11. A method for promoting synchrony of germination and emergence in plants, said method comprising treating plant seeds or plant parts used in propagation with an effective amount of a compound having the following formula (IA):

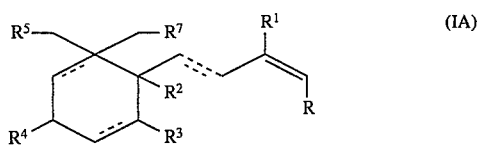

wherein

R is hydroxy, aldehyde, hydroxyloweralkyl, alkoxyloweralkyl, carboxyl or loweralkoxyl;

R¹ is loweralkyl;

R² is hydroxy;

R³ is loweralkyl or loweralkylhalide;

R⁴ is oxo;

R⁵ and R⁷ are hydrogen; the dotted line is optionally a single bond and the double dotted line is a double bond or a triple bond;

and R⁷ is absent when the dotted line adjacent to R⁵ is a single bond; for the purpose of enhancing synchrony of germination and emergence in plants.

12. A method according to claim 11, wherein said compound of formula IA, is applied to plant seeds.

13. A method according to claim 12, wherein the concentration of said compound of formula IA, ranges between 0.00000025 g/l and 0.50 g/l.

14. A method according to claim 11, wherein said compound of formula IA is selected from the group consisting of:

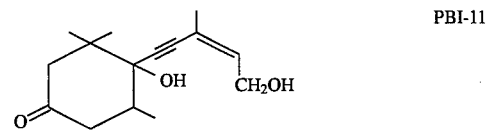

PBI-11

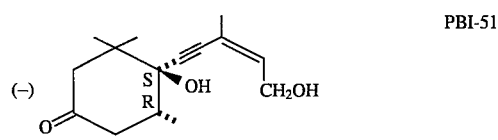

PBI-51

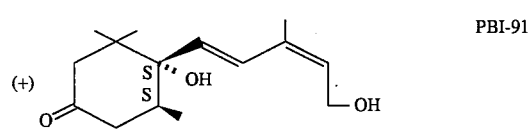

PBI-91

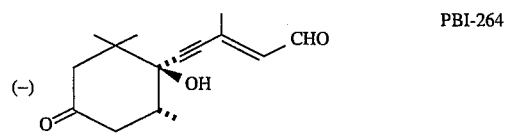

PBI-264

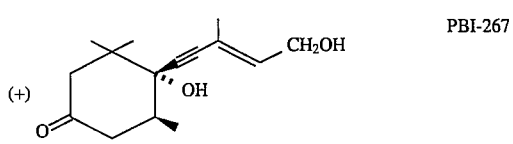

PBI-267

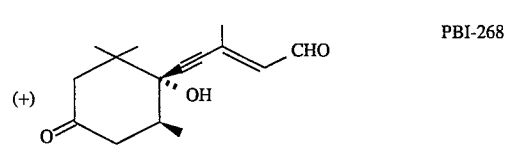

PBI-268

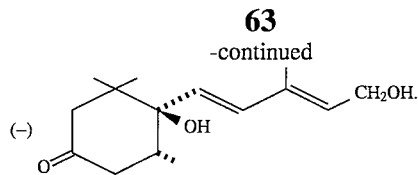

15. A method according to claim 14, wherein said compound of formula IA is applied to plant seeds.

16. A method according to claim 14, wherein the concentration of said compound of formula IA ranges between 0.00000025 g/l and 0.50 g/l.

17. A method according to claim 14, wherein said compound of formula Ia is applied to said seeds by soaking said seeds in an agricultural composition comprising an effective concentration of said compound of formula IA for the period of time required by said seeds to absorb said compound of formula IA in sufficient amounts to enhance synchrony of germination and emergence of the plants resulting from said seeds.

18. A method according to claim 14, wherein said plant seeds are selected from canola, corn, brassica, celery and carrot seeds.

19. A compound selected from the group consisting of:

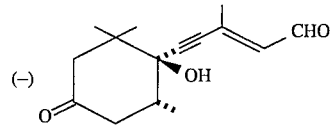

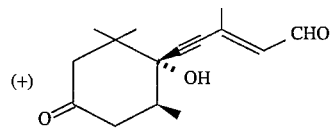

* * * * *